(12) United States Patent
Itoh

(10) Patent No.: US 7,408,037 B2
(45) Date of Patent: Aug. 5, 2008

(54) TUMOR ANTIGEN

(75) Inventor: Kyogo Itoh, Kiyama-machi (JP)

(73) Assignee: Green Peptide Co., Ltd., Fukuoka (JP)

( * ) Notice: Subject to any disclaimer, the term of this patent is extended or adjusted under 35 U.S.C. 154(b) by 0 days.

(21) Appl. No.: 11/543,066

(22) Filed: Oct. 5, 2006

(65) Prior Publication Data

US 2007/0031432 A1    Feb. 8, 2007

Related U.S. Application Data

(60) Division of application No. 10/353,929, filed on Jan. 30, 2003, now Pat. No. 7,148,326, which is a continuation-in-part of application No. PCT/JP01/06526, filed on Jul. 30, 2001.

(30) Foreign Application Priority Data

Jul. 31, 2000  (JP) .............................. 2000-231814

(51) Int. Cl.
*C07K 14/00* (2006.01)
(52) U.S. Cl. ..................... 530/350; 530/300; 424/185.1; 435/320.1; 435/325; 435/6; 435/69.3; 536/23.2
(58) Field of Classification Search ................ 530/350, 530/300; 424/185.1; 435/320.1, 325, 6, 435/69.3; 536/23.2
See application file for complete search history.

(56) References Cited

U.S. PATENT DOCUMENTS

| 5,840,839 A | 11/1998 | Wang et al. |
| 5,874,231 A | 2/1999 | Sonenberg et al. |
| 5,936,078 A | 8/1999 | Kuga et al. |

FOREIGN PATENT DOCUMENTS

| JP | 2000-189168 A | 7/2000 |
| WO | WO 97/21807 | 6/1997 |
| WO | WO 01/12660 A2 | 2/2001 |

OTHER PUBLICATIONS

Gritzapis et al. British Journal of Cancer, 2005. 92:72-79.*
Zaks and Rosenberg. Cancer Research, 1998. 58:4902-4908.*
Hida, N. et al., "A Simple Culture Protocol to Detect Peptide-Specific Cytotoxic T Lymphocyte Precursors in the Circulation," *Cancer Immunol Immunother* (2002) 51: 219-228.
Janeway, C. et al., *Immuno Biology*, 6th Edition, pp. 124, 125, 174, 175, 330-33, 346-349.
Mine, T. et al., "Humoral Responses to Peptides Correlate with Overall Survival in Advanced Cancer Patients Vaccinated with Peptides Based on Pre-existing, Peptide-Specific Cellular Responses," *Clinical Cancer Research*, vol. 10, Feb. 1, 2004, pp. 1-9.
Noguchi M. et al., "Phase I trial of patient-oriented vaccination in HLA-A2-positive patients with metastatic hormone-refractory prostate cancer," *Cancer Sci.*, Jan. 2004, vol. 95, No. 1, 77-84.
Noguchi, M., et al. "Immunological Monitoring During Combination of Patient-Oriented Peptide Vaccination and Estramustine Phosphate in Patents With Metastatic Hormone Refractory Prostate Cancer," *The Prostate*, 60:32-45(2004).
Mochizuki, K., et al. "Immunological evaluation of vaccination with Pre-Designated Peptides Frequently Selected as Vaccine Candidates in an Individualized Peptide Vaccination Regimen," *Intn 'l J. of Oncology*, 25:121-131 2004.
Rammensee et al, "MHC Ligands and Peptide Motifs: First Listing" *Immunogenetics*; 41:178-228 (1995).
Maeda et al., "Detection of peptide-specific CTL-precursors in peripheral blood lymphocytes of cancer patients," *British Journal of Cancer*, 87:7:796-804 (Sep. 23, 2002).
Dermer, G.B., "Another Anniversary for the War on Cancer," *BioTechnology*, 1994, 12:320.
Freshney, "Culture of Animal Cells," *A Manual of Basic Technique*, Alan R. Liss Inc., 1983 NY.
Riott et al., "Antigen Recognition," *Immunology*, 4th Ed., 1996, Mosby, p. 7, 9-7, 11).
Ito, Masaaki, et al. "Molecular Basis of T Cell-Mediated Recognition of Pancreatic Cancer Cells" *Cancer Research* 61, 2038-2046, Mar. 1, 2001.
Shain, Urur, et al. "Human neoplasms elicit multiple specific immune responses in the autologous host" *Pro. Natl., Acad. Sci. USA*, vol. 92, pp. 11810-11813, Dec. 1995 Immunology.
Yang, Damu, et al. "Identification of a gene coding for a protein possessing shared tumor epitopes capable of inducing HLA-A24-restricted Cytotoxic T Lymphocytes in Cancer Patients" *Cancer Research* 59, 4056-4063, Aug. 15, 1999.
Kikuchi, Megumi, et al., "Identification of Sart-1-derived peptide capable of inducing HLA-A24-restricted and tumor-specific cytotoxic T Lymphocytes" *Int'l. J. Cancer*; 81, 459-466 (1999).
Gomi, Shinya, et al. "A cyclophilin B gene encodes antigenic epitopes recognized by HLA-A24-restricted and tumor-specific CTLs" *The Journal of Immunology* pp. 4994-5004.
Shichijo, Shigeki, et al. "A Gene Encoding Antigenic peptides of Human Squamous Cell Carcinoma Recognized by Cytotoxic T Lymphocytes" *J. Exp. Med.* vol. 187, No. 3, Feb. 2, 1998 277-288.
Nakatsura, Tetsuya et al. "Gene Cloning of Immunogenic antigens Overexpressed in Pancreatic Cancer" *Biochemical and Biophysical Research Communication* 281, 936-944 (2001).
Yamada, Akira, et al. "Study of HLA class I restriction and the direction antigens of cytotoxic T lymphocytes at the tumor sites of ovarian cancer" *Cancer Immunol. Immunother* (1999) 48: 147-152.

(Continued)

*Primary Examiner*—David J. Blanchard
*Assistant Examiner*—Parithosh K. Tungaturthi
(74) *Attorney, Agent, or Firm*—Sughrue Mion, PLLC

(57) ABSTRACT

Tumor antigen inducing and/or activating HLA-A2-restricted tumor-specific cytotoxic T lymphocytes that is activated by recognizing HLA-A2 and a tumor antigen peptide, and a peptide or polypeptide derived from the tumor antigen, a polynucleotide encoding the peptide or a complementary strand polynucleotide thereof, a transformant comprising a recombinant vector which comprises the polynucleotide are provided.

3 Claims, 17 Drawing Sheets

OTHER PUBLICATIONS

Peiper, Matthias, et al. "Pancreatic Cancer Associated Ascites-Derived CTL Recognize a Nine-Amino-Acid Peptide GP2 Derived from HER2/neu" *Anticancer Research* 19: 2471-2475 (1999).

Pinol-Roma, Serafin, et al. "A novel heterogeneous nuclear RNP protein with a unique distribution on nascent transcripts" *The Journal of Cell Biology*, vol. 109 (No. 6, Pt. I) Dec. 1989 pp. 2575-2587.

Bodey, B., et al, "Failure of Cancer Vaccines: The Significant Limitations of this Approach to Immunotherapy," *Anticancer Research* 20:2665-2676, 2000.

Cox, A.L., et al., "Identification of a Peptide Recognized by Five Melanoma-Specific Human Cytotoxic T Cell Lines," *Science*, 264: 5159, 716-719, Apr. 29, 1994.

Ezzell, C., "Cancer "Vaccines": An Idea Whose Time Has Come?," *Journal of NIH Research*, 7:46-49, Jan. 1995.

Spitler, L.E., "Cancer Vaccines: The Interferon Analogy," *Cancer Biotherapy*, 10: 1-3, 1995.

Boon, T., "Toward A Genetic Analysis of Tumor Rejection Antigens," *Advances in Cancer Research*, 1992, 58: 177-210.

Arceci, R.J., "The potential for antitumor vaccination in acute myelogenous leukemia," *Journal of Molecular Medicine*, 76: 80-93, 1998.

Lee, K.H. et al. "Increased Vaccine-Specific T Cell Frequency After Peptide-Based Vaccination Correlates with Increased Susceptibility to In Vitro Stimulation But Does Not Lead to Tumor Regression," *Journal of Immunology*, 163: 6292-6300, 1999.

Zaks, T.Z.,et al, "Immunization with a Peptide Epitope (p. 369-377) from HER-2/new Leads to Peptide-specific Cytotoxic T Lymphocytes That Fail to Recognize HER-2/new+ Tumors," *Cancer Research*, 58: 4902-4908, Nov. 1, 1998.

Gao, P., et al. Tumor Vaccination That Enhances Antitumor T-Cell Responses Does Not Inhibit the Growth of Established Tumors Even in Combination With Interleukin-12 Treatment: The Importance of Inducing Intramoral T-Cell Migration,: *Journal of Immunotherapy*, 23: 643-653, 2000.

Hu, X., et al, "Enhancement of Cytolytic T Lymphocyte Precursor Frequency in Melonoma Patients following Immunization with the MAGE-1 Peptide Loaded Antigen Presenting Cell-based Vaccine," *Cancer Research*, 56: 2479-2483, Jun. 1, 1996.

Jaeger, E., et al., "Generation of Cytotoxic T-Cell Responses with Synthetic Melonoma-Associated Peptides In Vivo: Implications for Tumor Vaccines with Melanoma-Associated Antigens", *International Journal of Cancer*, 66: 162-169, 1996.

Mukherji, B., et al., "Induction of antigen-specific cytolytic T cells in situ I human melanoma by immunization with synthetic peptide-pulsed autologous antigen presenting cells," *Proceedings of the National Academy of Sciences USA*, 92: 8078-8082 (Aug. 1995).

Gura, T., "Systems for Identifying New Drugs Are Often Faulty," *Science*, 278: 1041-1042, Nov. 7, 1997.

Kanneganti G.K., et al. "The 160-kD subunit of human cleavage-polyadenylation specificity factor coordinates pre-mRNA 3'-end formation" *Genes & Development* 9: 2672-2683 1995.

Nagase, Takahiro, et al. "Prediction of the Coding Sequences of Unidentified human genes. IV> The coding sequences of 40 new genes (KIAA0121-KIAA0160) Deduced by Analysis of cDNA Clones from Human Cell LIne KG-1)" *DNA Research* 2 , 167-174, 1995.

International Search Report PCT/JP01/06526.

International Preliminary Examination Report PCT/JP01/06526.

\* cited by examiner ial role in the exclusion of cancer in vivo. Infiltration
TUMOR ANTIGEN This is a Divisional of application Ser. No. 10/353,929 filed Jan. 30, 2003 (now U.S. Patent No. 7,148,326); the entire disclosure of which is hereby incorporated by reference, and which is a alp of PCT/JP01/06526Jul. 30 2001.

FIELD OF THE INVENTION

The present invention relates to a tumor antigen, and more particularly relates to a peptide or a polypeptide recognized by tumor-specific cytotoxic T lymphocytes, a polynucleotide encoding the peptide or the polypeptide and a complementary strand polynucleotide thereto, a recombinant vector comprising the polynucleotide, a transformant comprising the recombinant vector, an antibody against the peptide or the polypeptide, a compound having any interaction with the peptide or the polypeptide or the polynucleotide, a cytotoxic T lymphocyte inducer consisting of the peptide and/or the polypeptide, and a pharmaceutical composition comprising the same, and a method for producing the polypeptide, a method for screening for a compound having any interaction with the peptide or the polypeptide or the polynucleotide, a method for inducing cytotoxic T lymphocytes using the peptide or the polypeptide, a method for measuring the peptide or the polypeptide or the polynucleotide encoding the polypeptide, and a reagent kit used for the measuring method.

BACKGROUND OF THE INVENTION

The immune system, particularly cytotoxic T lymphocytes (which, hereinafter, may be abbreviated to CTLs) play an important role in the exclusion of cancer in vivo. Infiltration of cytotoxic T lymphocytes exhibiting a cytotoxic activity against tumor cells has been detected at the tumor site of a cancer patient (Arch. Surg., 126:200-205, 1990.) A target molecule (tumor antigen) of the tumor-specific cytotoxic T lymphocytes was first discovered in a melanoma. A tumor antigen generated in a tumor cell is degraded in the cell into a peptide (tumor antigen peptide) consisting of 8 to 11 amino acids, which binds to a human leukocyte antigen (HLA) molecule that is the major histocompatibility complex antigen to be displayed on the surface of the tumor cell. The cytotoxic T lymphocytes recognize a complex consisting of HLA and the tumor antigen peptide, and damage the tumor cell. In other words, the cytotoxic T lymphocytes recognize the tumor antigen peptide in an HLA-restricted manner.

HLA is a cell membrane antigen, and is expressed on almost all eukaryotic cells. HLA is mainly classified into class I antigen and class II antigen. The HLA recognized by the cytotoxic T lymphocytes together with an antigen peptide belongs to class I antigens. HLA class I antigens are further classified into HLA-A, HLA-B, HLA-C, and so on. It was reported that HLA has genetic polymorphism. The HLA-A2 allele, which is one of polymorphisms of HLA-A subregion, is found in approximately 23% of African Blacks, approximately 53% of Chinese, approximately 40% of Japanese, approximately 49% of Northern Caucasians, and approximately 38% of Southern Caucasians.

As used herein, a tumor antigen means a protein, a polypeptide, or a peptide, which constitutes part of the tumor cell and is capable of inducing tumor-specific cytotoxic T lymphocytes. A tumor antigen peptide means a peptide that is generated as a result of degradation of the tumor antigen in a tumor cell and can induce or activate tumor-specific cytotoxic T lymphocytes upon being expressed on the cell surface by binding to an HLA molecule. In addition, the site of the amino acid sequence which is capable of inducing tumor-specific cytotoxic T lymphocytes that is present in a tumor antigen is called a tumor antigen epitope (tumor antigen determinant.)

In recent years, many genes encoding tumor antigens that can be recognized by cytotoxic T lymphocytes have been identified from cDNA of human tumor cells (Science 254: 1643-1647, 1991; J. Exp. Med. 183:1185-1192, 1996; J. Immunol. 163:4994-5004, 1999.) Some of these genes are involved in cellular proliferation and malignant transformation, including HER/neu (Proc. Natl. Acad. Sci. USA, 92:432-436, 1995) mutant cdk (Science, 269:1281-1284, 1995) mutant CASP-8 (J. Exp. Med., 186:785-793, 1997) and so on.

On the other hand, a molecule such as a tumor rejection antigen gene and a T cell antigen receptor (TCR), which are involved in specific immunity, have been identified in melanoma, esophageal cancer, and other cancers in the past 10 years, and a specific immunotherapy of advanced cancer or metastatic cancer has been studied using the peptide.

Now, in Europe and in the United States, cancer vaccine therapy has been developed in which cytotoxic T lymphocytes are activated by an administration of a tumor antigen in a cancer patient. Results from a clinical test of a melanoma specific tumor antigen have been reported. For example, administration of a melanoma antigen gp-100 peptide subcutaneously to melanoma patients along with administering interleukin-2(IL-2) intravenously gave a tumor regression in 42% of the patients (Nature Medicine, 4:321, 1998.) In this way, by utilizing a tumor antigen as a vaccine, an effective treatment against cancer can be achieved.

However, almost all of the identified tumor antigens are derived from melanomas. Tumor antigens derived from epithelial cancers and adenocarcinomas, such as pancreatic cancer, which occur at high incidence rates, have been reported for such specific immunotherapy only in a few papers. Pancreatic cancer is one of the largest causes of death by cancer in the world and causes about 27,000 deaths a year in the USA and about 50,000 deaths in Europe. The main factors causing these large numbers of deaths are lack of an effective therapeutic method, the difficulty of diagnosis, and the activity of this cancer. Only 1 to 4% of pancreatic cancer patients have overcome the disease, and the incidence substantially equals the death rate. Therefore, a new approach of therapy, for example, development of specific immunotherapy is needed.

In addition, in view of the diversity of cancer, an identical tumor antigen should not be expressed in the same degree in all cancer cells. Naturally, cancer vaccine therapy by activating the cytotoxic T lymphocytes using one kind of tumor antigen has a therapeutic effect on cancer having the tumor antigen. However, in order to induce and activate the tumor antigen-specific cytotoxic T lymphocytes and obtain a high therapeutic effect corresponding to the diversity of cancer, it is important to discover and use many novel tumor antigens in accordance with the diversity of cancer.

SUMMARY OF THE INVENTION

In one embodiment of the present invention, a peptide consisting of an amino acid sequence according to any one of those from SEQ ID NO: 1 to SEQ ID NO: 44 is provided.

In another embodiment of the present invention, a polypeptide consisting of an amino acid sequence according to any one of those from SEQ ID NO: 45 to SEQ ID NO: 53 is provided.

In still another embodiment of the present invention, a composition comprising one or more of peptides or polypeptides selected from the peptides, which consist of the amino acid sequence according to any one of those from SEQ ID NO:1 to SEQ ID NO:44, and the polypeptides, which consist of an amino acid sequence according to any one of those from SEQ ID NO:45 to SEQ ID NO:53 is provided.

In an additional embodiment of the present invention, an anti-cancer vaccine comprising one or more of peptides or polypeptides selected from the peptides, which consist of the amino acid sequence according to any one of those from SEQ ID NO:1 to SEQ ID NO: 44, and the polypeptides, which consist of an amino acid sequence according to any one of those from SEQ ID NO:45 to SEQ ID NO:53 is provided.

In yet another embodiment of the present invention, an anti-cancer vaccine comprising one or more of peptides or polypeptides selected from the peptides, which consist of the amino acid sequence according to any one of those from SEQ ID NO:1 to SEQ ID NO:44, and the polypeptides, which consists of an amino acid sequence according to any one of those from SEQ ID NO:45 to SEQ ID NO:53, for use in the treatment of pancreatic cancer, colon cancer, or stomach cancer is provided.

In another embodiment of the present invention, an inducer of cytotoxic T lymphocytes comprising one or more of peptides or polypeptides selected from the peptides, which consist of the amino acid sequence according to any one of those from SEQ ID NO:1 to SEQ ID NO: 44, and the polypeptides, which consist of an amino acid sequence according to any one of those from SEQ ID NO:45 to SEQ ID NO:53 is provided.

In still another embodiment of the present invention, a method for inducing cytotoxic T lymphocytes using one or more of peptides or polypeptides selected from the peptides, which consist of the amino acid sequence according to any one of those from SEQ ID NO:1 to SEQ ID NO:44, and the polypeptides, which consist of an amino acid sequence according to any one of those from SEQ ID NO:45 to SEQ ID NO:53 is provided.

In an additional embodiment of the present invention, a polynucleotide encoding a peptide or a polypeptide consisting of the amino acid sequence according to any one of those from SEQ ID NO: 1 to SEQ ID NO: 53, or the complementary strand thereof is provided.

In yet another embodiment of the present invention, a polynucleotide according to any one of those from SEQ ID NO:54 to SEQ ID NO:62, or the complementary strand thereof is provided.

In another embodiment of the present invention, a polynucleotide according to any one of those from SEQ ID NO:54 to SEQ ID NO:62, wherein a polypeptide encoded by the polynucleotide induces cytotoxic T lymphocytes and/or is recognized by cytotoxic T lymphocytes, or the complementary strand thereof is provided.

In still another embodiment of the present invention, a polynucleotide that hybridizes to the polynucleotide or the complementary strand thereof under stringent conditions is provided.

In an additional embodiment of the present invention, a recombinant vector comprising the polynucleotide or the complementary strand thereof or the polynucleotide that hybridizes to the polynucleotide or the complementary strand thereof under stringent conditions is provided.

In yet another embodiment of the present invention, a recombinant expression vector comprising the polynucleotide or the complementary strand thereof or the polynucleotide that hybridizes to the polynucleotide or the complementary strand thereof under stringent conditions is provided.

In another embodiment of the present invention, a transformant transformed with the recombinant vector or the recombinant expression vector, which comprises the polynucleotide or the complementary strand thereof or the polynucleotide that hybridizes to the polynucleotide or the complementary strand thereof under stringent conditions is provided.

In still another embodiment of the present invention, a method for producing the polypeptide, which comprises culturing the transformant transformed with the recombinant expression vector that comprises the polynucleotide or the complementary strand thereof or the polynucleotide that hybridizes to the polynucleotide or the complementary strand thereof under stringent conditions is provided.

In an additional embodiment of the present invention, an antibody that immunologically recognizes the peptide or the polypeptide is provided.

In yet another embodiment of the present invention, a method for screening for a compound that enhances at least recognition of the peptide or the polypeptide by HLA-A2-restricted cytotoxic T lymphocytes, by interacting with the peptide or the polypeptide and/or HLA-A2 to enhance, and/or the compound that enhances expression of the polynucleotide or the complementary strand thereof by interacting with the same, is provided wherein the method uses at least one selected from a group consisting of the peptide, the polypeptide, the polynucleotide, the complementary strand thereof, the recombinant vector, the recombinant expression vector, the transformant, and the antibody.

On another embodiment of the present invention, a compound obtained by the method for screening a compound that enhances at least recognition of the peptide or the polypeptide by HLA-A2-restricted cytotoxic T lymphocytes, by interacting with the peptide or the polypeptide and/or HLA-A2 to enhance, and/or the compound that enhances expression of the polynucleotide or the complementary strand thereof by interacting with the same, is provided wherein the method uses at least one selected from a group consisting of the peptide, the polypeptide, the polynucleotide, the complementary strand thereof, the recombinant vector, the recombinant expression vector, the transformant, and the antibody.

In still another embodiment of the present invention, a compound that enhances recognition of at least one of the peptide or the polypeptide by the HLA-A2-restricted cytotoxic T lymphocytes, or the compound that enhances the expression of the polynucleotide or the complementary strand thereof by interacting with the same is provided.

In an additional embodiment of the present invention, a pharmaceutical composition used for cancer treatment, comprising at least one selected from a group consisting of the peptide, the polypeptide, the polynucleotide, the complementary strand thereof, the recombinant vector, the recombinant expression vector, the transformant, the antibody, and the compound is provided.

In yet another embodiment of the present invention, use of the composition, the anti-cancer vaccine, the inducer of the cytotoxic T lymphocytes, or the pharmaceutical composition for cancer disease is provided.

In another embodiment of the present invention, a method for measuring quantitatively or qualitatively the peptide or the polypeptide, or the polynucleotide is provided.

In still another embodiment of the present invention, a reagent kit used in the method for measuring quantitatively or qualitatively the peptide or the polypeptide, or the polynucleotide, is provided wherein the kit comprises at least one selected from a group consisting of the peptide, the polypeptide, the polynucleotide or the strain thereof, or the antibody.

In an additional embodiment of the present invention, use of a reagent kit for a test of the cancer disease is provided, wherein the kit is used to measuring quantitatively or qualitatively the peptide or the polypeptide, or the polynucleotide, comprises at least one selected from a group consisting of the peptide, the polypeptide, the polynucleotide or the complementary strain thereof, or the antibody.

BRIEF DESCRIPTION OF THE DRAWINGS

FIGS. 4A-4F each show that OK-CTLp recognizes COS7 cells, in which each of cDNA clones 1 to 6, having high homology with UBE2V, HNRPL, WHSC2, EIF4EBP1, ppMAPkkk, and 2-5 OAS3, respectively, was coexpressed with HLA-A2, in an HLA-A2-restricted manner. The symbol —■— shows the amount of interferon-γ produced by OK-CTLp, when the HLA-A0207 gene was coexpressed with the each tumor antigen gene in target cells, —◇— shows the amount of interferon-γ produced by OK-CTLp, when the HLA-A2402 gene was coexpressed with each tumor antigen gene in the target cells.

FIGS. 11A-11F show that OK-CTLP recognizes the peptides which are derived from gene products of the tumor antigen genes 1 to 6, having high homology with UBE2V, HNRPL, WHSC2, EIF4EBP1, ppMAPkkk, and 2-5 OAS3, respectively.

FIGS. 18A-18E each show that peptides derived from gene products of the tumor antigen genes 1 to 5, having high homology with UBE2V, HNRPL, WHSC2, EIF4EBP1, and ppMAPkkk, respectively, induces CTL that recognizes the peptide in a HLA-A2-restricted manner, from peripheral blood mononuclear cells of a cancer patient. The symbol —□— shows T2 cells in which the tumor antigen peptide was made to express and —◇— shows autologous PHA blastoid T cells.

DETAILED DESCRIPTION OF THE INVENTION

Figure 1:
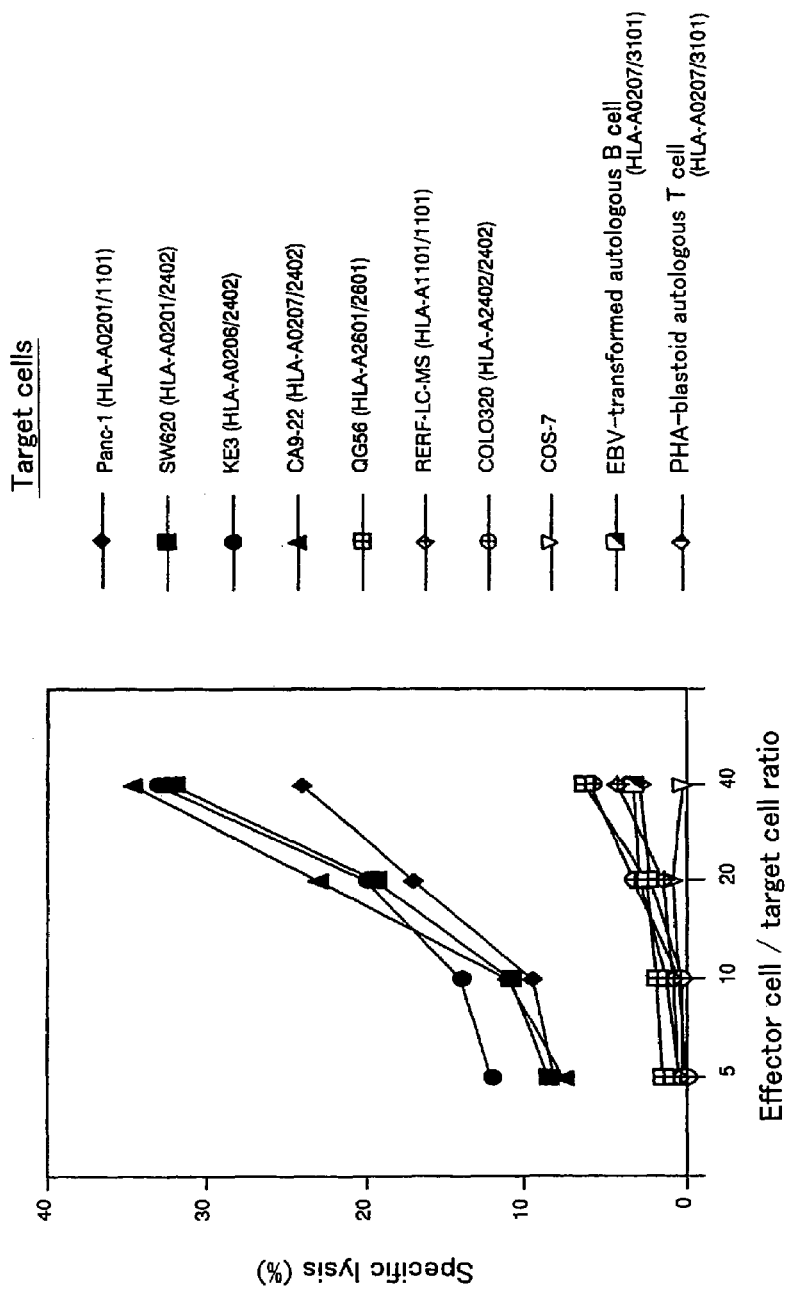
FIG. 1 illustrates that OK-CTLp (HLA-A0207/A3101) lyses tumor cells in an HLA-A2-restricted manner.

In order to identify a tumor rejection antigen gene and a tumor antigen encoded by the gene, which can be used for specific immunotherapy for pancreatic cancer, HLA-A2-restricted tumor-specific cytotoxic T lymphocytes have been established in the present invention that are activated by recognizing HLA-A2 and a tumor antigen peptide (hereafter, this cell may be called OK-CTLp) from a colon cancer patient, and genes encoding tumor antigens, which can be recognized by these tumor-specific cytotoxic T lymphocytes (CTL,) have been isolated/identified from a cDNA library of Panc-1 cell that as the human pancreatic adenocarcinoma cell line using the gene expression cloning method. In the present invention, genes have also been identified, which can be recognized by CTL in the same way as described above, from genes identified as those encoding the tumor antigen by the SEREX (Serological analysis of recombinant cDNA expression libraries) method (Proc. Natl. Acad. Sci. USA, 92:11910-11813, 1995.) In addition, based on the tumor antigen encoded by the gene obtained, a peptide having the tumor antigen epitope has been found in the present invention.

As used herein, a polypeptide means a long chain peptide of arbitrary peptides comprising two or more amino acids bound to each other by a peptide bond or by a modified peptide bond. For example, a protein is included in the definition of polypeptide herein. Moreover, a short chain peptide sometimes called an oligopeptide or an oligomer is simply called a peptide herein.

"Recognize" herein means that a subject distinguishes an object from others and cognates it, for example, binds to the object cognized. Particularly, in the present invention, CTL which recognize the tumor cells or the tumor antigen peptides means that CTL binds through a T cell receptor to the tumor antigen peptides that are presented by HLA.

"Activate" herein means to enhance or to make it work further a thing or a state, which has an activity or an action. Particularly, in the present invention, activation of CTL means that CTL recognizes an antigen being presented by HLA to produce IFN-γ or CTL shows cytotoxicity against the target cells recognized by CTL.

"Induce" herein means to generate an activity or an action from a thing or a state that are in a phase merely having the activity or the action. Particularly, in the present invention, induction of an antigen-specific CTL means to make CTL, which specifically recognizes a certain antigen differentiate and/or proliferate in vitro or in vivo. In addition, the inducer of cytotoxic T lymphocytes in the present invention means a composition which changes the state, where CD8-positive T lymphocytes specifically recognizing a certain antigen is absent or present in a very low degree, to the state, where the cytotoxic T lymphocytes recognizing the antigen is present in a very degree.

(Isolation and Identification of the Tumor Antigen Gene, Tumor Antigen, and Tumor Antigen Peptide)

In the present invention, OK-CTLp that was HLA-A2-restricted cytotoxic T lymphocyte described above was used as an effector cell and tumor antigens capable of activating this cell were isolated and identified by using the gene expression cloning method. In other words, cDNA of the human pancreatic adenocarcinoma cell line Panc-1 and cDNA of HLA-A0207 were cotransfected into COS-7 cells, and among those cells in which the transfected genes were expressed, the cells which enhance IFN-γ production from OK-CTLP were selected, and hence, the gene encoding the tumor antigen capable of activating CTL was identified. The method will be presented in more detail in examples described herein. As a result, seven cDNA clones were obtained which were recognized by OK-CTLp in an HLA-A2-restricted manner.

In addition, two genes, KM-PA-2 and KM-PA-4, encoding tumor antigens capable of activating CTL in an HLA-A2-restricted manner were found in the same manner as described above from the genes encoding the tumor antigens, were detected from a cDNA library of the human pancreatic adenocarcinoma cell line CFPAC-1 using the SEREX method and already reported (Biochim. Biophys. Res. Commun., 281:936-944, 2001,). The SEREX method is a method that can be applied to detection of a tumor antigen. However, among 1500 or more kinds of tumor antigens detected by this method, those being identified as tumor antigens capable of inducing both cell-mediated immunity and humoral immunity are only MAGE-1, tyrosinase, and NY-ESO-1. Thus, the tumor antigen identified by the SEREX method cannot always activate CTL. The present invention first revealed that the tumor antigen genes described above, KM-PA-2 and KM-PA-4, can activate CTL in an HLA-A2-restricted manner.

All seven cDNA clones described above, which were obtained from Panc-1 cell, contained a complete open reading frame (ORF). The nucleotide base sequence of these genes was determined by the Sanger method (Chain Terminator method) to estimate the amino acid sequence on the basis of the nucleotide base sequence. When a homology search was carried out for these nucleotide base sequences and deduced amino acid sequences in an existing database such as Gen-Bank, it was found that these genes were cDNAs whose nucleotide base sequences are novel, though they have high homology with genes as described below. There is no report on the known homologous genes functioning as a tumor antigen. With regard to clone 3 among the 7 cDNA clones (clones 1 to 7) obtained, the sequence of an initial clone, which was obtained by the gene expression cloning method described above, and has high homology with that of a gene of Wolf-Hirschhorn syndrome candidate 2 protein (WHSC2), was 25 bp shorter at the 5'-terminal region than that of WHSC2, so that full-length cDNA was obtained from the cDNA library of the Panc-1 cell by a standard colony hybridization method using the clone labeled with $^{32}P$ as a probe. Hereinafter, the genes of the Panc-1 cell, from which the above-described clones 1 to 7 were derived, will be called gene 1 to 7, respectively. Also, the polypeptides consisting of an amino acid sequence encoded by each gene are occasionally herein called gene product 1 to 7. Deduced amino acid sequences encoded by each of these genes are shown as SEQ ID NO: 45 to SEQ ID NO: 51, respectively, and the nucleotide base sequences thereof are shown as SEQ ID NO:54 to SEQ ID NO:60, respectively. The above described genes 1 to 6 and the gene 7 were registered at the DNA Data Bank of Japan (DDBJ) of the National Research Institute of Genetics in Jun. 12, 2000 and Aug. 2nd, 2000, respectively (Table 1).

For KM-PA-2 and KM-PA-4, the homologous genes have been reported as shown in Table 1 (Biochim. Biophys. Res. Commun., 281:936-944, 2001.) The nucleotide base sequences of KM-PA-2 and KM-PA-4 are shown as SEQ ID NO:52 and SEQ ID NO:53, respectively, and the deduced amino acid sequences are shown as SEQ ID NO: 61 and SEQ ID NO: 62, respectively.

TABLE 1

| | cDNA clone (gene) | | Polypeptide encoded by cDNA | | | |
|---|---|---|---|---|---|---|
| | Base length (bp) [DDBJ accession no.] | SEQ ID: NO | | Amino acid length | SEQ ID: NO | Homologous gene [GeneBank accession no.] |
| 1 | 1775 [AB044550] | 54 | PP 1 | 270 | 45 | ubiquitin-conjugated enzyme variant Kua (UBE2V) [AF155120] |
| 2 | 2097 [AB044547] | 55 | PP 2 | 589 | 46 | heterogeneous nuclear ribonucleoprotein L (HNRPL) [NM_001533] |
| 3 | 2243 [AB044549] | 56 | PP 3 | 549 | 47 | Wolf-Hirschhorn Syndrome candidate 2 protein (WHSC2) [AK001304] |
| 4 | 831 [AB044548] | 57 | PP 4 | 118 | 48 | eIF-4E-binding protein 1 (EIF4EBP1) [NM_004095] |
| 5 | 2404 [AB044546] | 58 | PP 5 | 779 | 49 | partial putatibe mitogen actibated protein kinase kinase kinase (ppMAPkkk) [AJ242724] |
| 6 | 6707 [AB044545] | 59 | PP 6 | 1087 | 50 | 2',5'-oligoadenylate synthetase 3 (2-5 OAS3) [NM_006187] |
| 7 | 769 [AB046744] | 60 | PP 7 | 216 | 51 | clevage and polyadenylation specificity factor (CPSF) [U37012] |
| KM-PA-2 | 2060 [AB060694] | 61 | PP-KM-PA-2 | 634 | 52 | KIAA0124 gene [D50914] human homologue of mouse block of proliferatin 1 (Bop1) [BC005160] |
| KM-PA-4 | 1841 | 62 | PP-KM-PA-4 | 142 | 53 | coactosin-like protein (CLP) [L54057] |

The nucleotide base sequence of gene 1 has high homology with that of the ubiquitin-conjugated enzyme variant Kua gene (UBE 2V) registered at GenBank (accession no. AF155120.) The length of the deduced amino acid (aa) encoded by gene 1 was slightly longer than that encoded by the UBE2V gene (3 aa in positions 109 to 111.) The function of UBE2V has not so far been reported.

The nucleotide base sequence of gene 2 has high homology with that of the heterogeneous nuclear ribonucleoprotein L (HNRPL) gene (accession no. NM_001533.) However, the deduced amino acid length was slightly longer than that of the HNRPL gene at the N-terminal positions 1 to 31. The HNRPL gene product is a heterogeneous nuclear ribonucleoprotein complex and provides a substrate for the processing events that the mRNA precursor undergoes in the cytoplasm.

The nucleotide base sequence of gene 3 has high homology with that of the Wolf-Hirschhorn syndrome candidate 2 proteins (WHSC2) gene registered at GenBank (accession no. AK001304.) The WHSC2 gene seems to have some functions in the phenotype of WHS, a multiple malformation syndrome characterized by mental and developmental defects resulting from a partial deletion of the short arm of chromosome 4.

The nucleotide base sequence of gene 4 has high homology with that of the eIF-4E-binding protein 1 gene (EIF4EBP1, accession no. NM_004095.) The product of EIF4EBP1 gene is known as a translation initiation factor that initiates insulin-dependent phosphorylation of 4E-BP1, making it available to form an active cap-binding complex.

The nucleotide base sequence of gene 5 has homology with that of the partial putativemitogen-activated protein kinase kinase kinase gene (ppMAPkkk, accession no. AJ242724) registered at GenBank. The deduced amino acid sequence encoded by gene 5 is 230 aa longer at the N-terminal and 258 aa longer at the C-terminal as compared with that of the registered ppMAPkkk gene (its function has not yet been reported.)

The nucleotide base sequence of gene 6 consists of 6707 bp and has homology with that of the 2',5'-oligoadenylate synthetase 3 gene (2-5 OAS3 gene, accession no. NM_006187) with a total of 13-aa differences at positions 18, 159, 249, 287, 288, 316, 393 to 398, and 984. 2-5 OAS3 is known as an IFN-induced protein that plays an important role in immune-protection against microorganism infection.

The nucleotide base sequence of gene 7 has homology with positions 3701 to 4463 of the Human cleavage and polyadenylation specificity factor (CPSF, accession no. U37012) gene and the amino acid sequence is approximately 1226 aa shorter.

The nucleotide base sequence of gene KM-PA-2 has high homology with that of the KIAA0124 and human homologues of mouse block of proliferation 1 (Bop1.) The nucleotide base at position 1466 of the KIAA0124 gene is guanine (G) and thus, the amino acid residue of the 465$^{th}$ position is histidine (H). On the contrary, in gene KM-PA-2, they are adenine (A) and arginine (R), respectively.

The nucleotide base sequence of gene KM-PA-4 and the amino acid sequence encoded by the gene are identical to those of coactosin-like protein (CLP.)

In order to obtain tumor antigen peptides from the above-described 9 genes encoding a tumor antigen, peptides were designed and synthesized based on the amino acid sequences encoded by the above-described genes. For gene 7, the gene was regarded as a part of a gene consisting of a longer base sequence, so that the peptides, which were derived from the amino acid sequence encoded by the gene (CPSF) homologous to gene 7, were also designed and synthesized. It has been known that a tumor antigen peptide capable of binding to the HLA-A2 has a motif (a specific sequence) in its sequence. Then, at first, the peptide having an HLA-A2 binding motif (a specific sequence) was searched for in the literature (J. Immunol., 152:163, 1994; Immunogenetics, 41:178, 1994,) and the peptides of 9-mer to 11-mer, which were different from each other and suited to the motif obtained, were designed and synthesized based on the amino acid sequence encoded by the above described genes. Recognition of each peptide by CTL was measured using OK-CTLp or several kinds of OK-CTL clones obtained by cloning OK-CTLp by the limiting dilution method using IFN-γ production from these CTL as an indicator. The OK-CTL clones are the cells recognizing any one of the above-described genes 1 to 7. On the other hand, OK-CTLp recognizes any of genes 1 to 7. The results revealed that OK-CTLp is a cell population recognizing various kinds of tumor antigens. Therefore, when the OK-CTL clones were used to test the peptide for its ability to activate CTL, a clone was used which recognizes the product of the gene encoding the same peptide as that to be tested. Forty four peptides (SEQ ID NO:1 to SEQ ID NO:44; Table 2 and Table 3) among those synthesized were recognized by OK-CTLp or OK-CTL clones and enhanced IFN-γ production from CTL. Among these peptides, P1 to P5, P6 to P9, P10 to P13, P14 and P15, P16 to P18, and P19 are the peptides consisting of a partial sequence of the amino acid sequences encoded by gene 1, gene 2, gene 3, gene 4, gene 5, and gene 6, respectively, and encoded also by genes UBE2V, HNRPL, WHSC2, EIF4-EBP1, ppMAPkkk, and 2-5 OAS3 having high homology with each genes. On the other hand, P25, P26, P27, P28, P30, and P31 are the peptides consisting of a partial sequence of the amino acid sequences encoded by gene 7 and gene CPSF having high homology with gene 7. P20, P21, P22, P23, P24, P29, and P32 consist of a partial sequence of the amino acid sequence specific to CPSF.

TABLE 2

| Number | Origin of peptide | Position of amino acid sequence | Amino acid sequence | SEQ ID NO: in sequence listing |
|---|---|---|---|---|
| P 1 | Gene 1 | 43-51 | RLQEWCSVI | 1 |
| P 2 | (UBE2V) | 64-73 | LLLLARWEDT | 2 |
| P 3 | | 85-93 | LIADFLSGL | 3 |
| P 4 | | 201-209 | LLQDWHVIL | 4 |
| P 5 | | 208-216 | ILPRKHHRI | 5 |
| P 6 | Gene 2 | 140-148 | ALVEFEDVL | 6 |
| P 7 | (HNRPL) | 404-412 | CLYGNVEKV | 7 |
| P 8 | | 443-451 | FMFGQKLNV | 8 |
| P 9 | | 501-510 | NVLHFFNAPL | 9 |
| P10 | Gene 3 | 103-111 | ASLDSDPWV | 10 |
| P11 | (WHSC2) | 141-149 | ILGELREKV | 11 |
| P12 | | 157-165 | MLPLECQYL | 12 |
| P13 | | 267-275 | TLLRKERGV | 13 |
| P14 | Gene 4 | 51-59 | RIIYDPKFL | 14 |
| P15 | (EIF4EBP1) | 52-60 | IIYDRKFIM | 15 |
| P16 | Gene 5 | 290-298 | QILKLLFL | 16 |
| P17 | (ppMAPkkk) | 294-302 | GLLFLHTRT | 17 |
| P18 | | 432-440 | DLLSHAFFA | 18 |
| P19 | Gene 6 (2-5 OAS3) | 666-674 | QQLCVYWIV | 19 |
| P20 | CPSF | 285-293 | SLLYLNQSV | 20 |
| P21 | CPSF | 250-258 | KVHPVIWSL | 21 |
| P22 | CPSF | 534-542 | DMWTVIAPV | 22 |
| P23 | CPSF | 882-890 | QLGQGNLKV | 23 |
| P24 | CPSF | 392-400 | LLLKYTEKL | 24 |

TABLE 2-continued

| Number | Origin of peptide | Position of amino acid sequence | Amino acid sequence | SEQ ID NO: in sequence listing |
|---|---|---|---|---|
| P25 | Gene 7 | 1367-1375 | TMLPHHAGL | 25 |
| P26 | Gene 7 | 1296-1304 | LLRRADFHV | 26 |
| P27 | Gene 7 | 1401-1409 | ELLNRYLYL | 27 |
| P28 | Gene 7 | 1358-1366 | LLMLQNALT | 28 |
| P29 | CPSF | 797-805 | YQLPDWRLV | 29 |
| P30 | Gene 7 | 1359-1368 | LMLQNALTTM | 30 |
| P31 | Gene 7 | 1358-1367 | LLMLQNALTT | 31 |
| P32 | CPSF | 456-465 | TQLATYSFEV | 32 |

TABLE 3

| Number | Origin of peptide | Position of amino acid sequence | Amino acid sequence | SEQ ID NO: in sequence listing |
|---|---|---|---|---|
| P 33 | KM-PA-2 | 29-38 | LEWYDDFPHV | 33 |
| P 34 | | 115-124 | FSGDVMIHPV | 34 |
| P 35 | | 172-180 | WAQEDPNAV | 35 |
| P 36 | | 179-188 | AVLGRHKMHV | 36 |
| P 37 | | 326-335 | RLWEVATARC | 37 |
| P 38 | | 348-356 | VAWNPSPAV | 38 |
| P 39 | | 585-593 | DLLQNPLLV | 39 |
| P 40 | | 586-595 | LLQNPLLVPV | 40 |
| P 41 | | 612-621 | VIFHPTQPWV | 41 |
| P 42 | KM-PA-4 | 15-24 | NLVRDDGSAV | 42 |
| P 43 | | 57-65 | RLFAFVRFT | 43 |
| P 44 | | 104-113 | VVQNFAKEFV | 44 |

These tumor antigen peptides are presented on a cell surface by HLA-A2 and recognized by T cell receptor (TCR) expressed on the peptide-specific OK-CTL clone. The peptides derived from gene 1 and UBE2V, gene 2 and HNRPL, or gene 6 and 2-5 OAS3 are recognized by OK-CTL clone expressing TCR-Vβ 8.1, TCR-Vβ 3.2, or TCR-Vβ 14. In addition, Peptides derived from gene 3 and WHSC2, gene 4 and EIF4EBP1, or gene 5 and ppMAPkkk are recognized by OK-CTL clone expressing TCR-Vβ13, TCR-Vβ8.1, or TCR-Vβ18, respectively.

Two each of the OK-CTL clones that recognize peptides derived from gene 1 and UBE2V, gene 2 and HNRPL, and gene 6 and 2-5 OAS3 were expressed TCR possessing different complementarity-determining regions 3 (CDR 3; an element responsible for binding to antigenic epitopes on a groove of the HLA Class I molecules,) respectively. The OK-CTL clone recognizing peptides derived from gene 3 and WHSC2, gene 4 and EIF4EBP1, and gene 5 and ppMAPkkk also expressed TCR possessing the different CDR3, respectively.

Moreover, the above-described 44 peptides recognized by OK-CTLp each induced HLA-A2-restricted tumor-specific CTL in vitro from the peripheral blood mononuclear cells (which, hereinafter, may be abbreviated to PBMC) which are autologous cells derived from a colon cancer patient from whom OK-CTLp was obtained, and/or from the PBMC of HLA-A0201[+] cancer patients (pancreatic cancer, colon cancer, and stomach cancer.) The above-described CTL induced from the peripheral blood mononuclear cells of the cancer patients lysed HLA-A2[+] tumor cells in a dose-dependent manner. However, no lysis was observed in the HLA-A2[−] tumor cell RERF-LC-MS, and HLA-A[+] autologous EBV-B cells and HLA-A⁺ T cells stimulated by PHA, both of which are derived from normal cells. In addition, the above-described CTL showed cytotoxicity in a dose-dependent manner against the T2 cells that were pulsed with the same peptide as that used for stimulation.

On the basis of the examination described above, 44 tumor antigen peptides capable of activating OK-CTLp were obtained. Furthermore, it was found that these peptides could induce HLA-A2-restricted tumor-specific CTLs from PBMC derived from patients of pancreatic cancer, colon cancer, and/or stomach cancer. In addition, it was revealed that both the pancreatic adenocarcinoma cell line Panc-1 and the colon adenocarcinoma cell line SW620 are recognized by CTLp and by CTLs induced from PBMC by the above described peptide. This result suggests that pancreatic cancer and colon cancer have a common tumor antigen epitope recognized by host CTLs.

(Polypeptide and Peptide)

A polypeptide according to the present invention is a polypeptide consisting of the amino acid sequence each of which is encoded by the above described genes 1 to 7 obtained from the human pancreatic adenocarcinoma cell line Panc-1 or gene KM-PA-2 or KM-PA-4 obtained from the human pancreatic adenocarcinoma cell line CFPAC-1, and preferably, a polypeptide consisting of the amino acid sequence described in any one of those from SEQ ID NO:45 to SEQ ID NO:53. These polypeptides can be used for inducing and/or activating CTL as a tumor antigen. Moreover, these polypeptides can be used as a material for specifying a tumor antigen epitope to obtain a tumor antigen peptide.

A peptide according to the present invention can be obtained by designing peptides, for example, which are suited for the HLA-A2-restricted motif, based on the amino acid sequence of the above-described polypeptide, to select ones recognized by CTL, for example, which activate and/or induce CTL, from the designed peptides. A peptide according to the present invention may be the peptide having a property of a tumor antigen epitope presented on the surface of an antigen-presenting cell through binding to HLA-A2 and recognized by CTL. The peptide consists of amino acid residues of at least about 5 or more, preferably about 7 or more, and more preferably 9 to 10. Particularly preferably, the peptide is one consisting of an amino acid sequence described in any one of those from SEQ ID NO:1 to SEQ ID NO:44. These peptides can be used as a tumor antigen peptide for activating and/or inducing the HLA-A2-restricted tumor-specific cytotoxic T lymphocytes.

For activating and/or inducing CTL, one of the above-described polypeptide or peptide may be used or they may be used in combination of two or more. As described above, CTL is a population consisting of plural cells that recognize various antigens, so that it is recommended to use these peptides preferably in combination of two or more.

A polypeptide or peptide, which has one or several amino acid(s) with a mutation such as deletion, substitution, addition, or insertion introduced into the polypeptide or peptide specified as above and is recognized by at least the HLA-A2-restricted CTL, is also included within the scope of the present invention. A means for introducing mutations such as a deletion, substitution, addition, or insertion is well known and, for example, Ulmer's technique (Science, 219:666, 1983) can be employed. When introducing such mutation, in view of preventing a change of the fundamental properties (such as the physical properties, activity, or immunological activity) of the peptide, mutual substitution among, for example, amino acids having similar properties (polar amino acids, non-polar amino acids, hydrophobic amino acids, hydrophilic amino acids, positively charged amino acids, negatively charged amino acids, aromatic amino acids, and so on) can be carried out. In addition, some modification can be made on these peptides to such an extent that there is no notable change of their function, such as modification of the constitutive amino group or carboxyl group.

(Polynucleotide)

A polynucleotide according to the present invention is a polynucleotide consisting of the nucleotide base sequence described in any one of those from SEQ ID NO:54 to SEQ ID NO:62, which are the nucleotide base sequences of genes 1 to 7 or gene KM-PA-2 or KM-PA-4 obtained from the human pancreatic adenocarcinoma cell line Panc-1 or the human pancreatic adenocarcinoma cell line CFPAC-1 as described above, or the complementary strand thereof. The polynucleotide may also be a polynucleotide encoding each of the peptides consisting of the amino acid sequences described in any one of those from SEQ ID NO: 1 to SEQ ID NO:44 or a polypeptide consisting of the amino acid sequence described in any one of SEQ ID NO:45 to SEQ ID NO:53, or the complementary strand thereof. Moreover, the above-described polynucleotide may consist of a nucleotide base sequence of at least about 15 or more, preferably about 21 to 30 or more nucleotides, wherein the nucleotide base sequence corresponds to a region encoding a tumor antigen epitope in the amino acid sequence of the polypeptides according to the present invention, or the complementary strand thereof. Selection of a useful polynucleotide and determination of its nucleotide base sequence are possible, for example, by employing well-known protein expression systems to confirm the ability of the expressed protein to induce and/or activate CTL.

Moreover, a polynucleotide that hybridizes to the above-described polynucleotide under stringent conditions is included in the scope of the present invention. In the case where the polynucleotide molecule is a DNA molecule, "a DNA molecule that hybridizes to a DNA molecule under stringent conditions" can be obtained, for example, by the method described in "Molecular Cloning: A Laboratory Manual (Cold Spring Harbor Laboratory, 1989.)" "To hybridize under stringent conditions" herein means that a positive hybridizing signal is still observed even under the condition in which, for example, hybridization is carried out in a solution containing 6×SSC, 0.5% SDS, and 50% formamide at 42° C. and then, washing is carried out in a solution containing 0.1×SSC and 0.5% SDS at 68° C.

The above-described polynucleotide can induce and/or activate the HLA-A2-restricted CTL, when it is expressed in cells having HLA-A2. In this case, the above-described polynucleotide has a poly(A) structure in its 3'-terminal. The number of poly(A) does not have an influence on the site encoding the amino acid acting as a tumor antigen, so that the number of poly(A,) of the polynucleotide is not limited.

All of the above-described polynucleotides provide genetic information useful for producing a polypeptide or a peptide according to the present invention or can be also utilized as a reagent and a standard of a nucleic acid.

(Recombinant Vector)

A recombinant vector can be obtained by inserting the above-described polynucleotide into an adequate DNA vector. The DNA vector used is properly selected in accordance with the kind of host and the purpose of use. The DNA vector may be a naturally existing one and also may be one that lacks a part of its DNA other than that necessary for replication. For example, vectors can be exemplified as those derived from a chromosome, an episome, and a virus, for example, vectors derived from a bacterial plasmid, derived from a bacteriophage, derived from a transposon, derived from an enzyme episome, derived from an inserting element, and derived from an enzyme chromosome element, for example, vectors derived from a virus such as baculovirus, papovavirus, SV40, vacciniavirus, adenovirus, fowlpox virus, pseudorabies virus, and retrovirus, and vectors prepared by combination of them, for example, vectors derived from the genetic element of the plasmid and the bacteriophage, for example, a cosmid and a phagemid. Further, an expression vector and a cloning vector etc. can be used in accordance with the desired purpose.

The recombinant vector, which comprises the constitutional elements of the desired DNA sequence and a DNA sequence possessing information relating to replication and regulation, such as a promoter, a ribosome-binding site, a terminator, a signal sequence, an enhancer, and so on, can be prepared by combining them using well-known methods. As a method for inserting the polynucleotide according to the present invention into the above-described DNA vector, the well-known methods can be employed. For example, a method can be used, wherein an appropriate restriction enzyme is chosen for treating a DNA to cleave it at a specific site, and then, the DNA is mixed with the DNA used as a vector treated in the same way, followed by ligating with a ligase. A desired recombinant vector can also be obtained by ligating an adequate linker to the desired polynucleotide followed by inserting the resultant molecule into a multi-cloning site of a vector suitable for a purpose.

(Transformant)

The DNA vector in which the above-described polynucleotide has been inserted can be used to obtain a transformant by transforming a well-known host such as *Escherichia coli*, yeast, *Bacillus subtillis*, an insect cell, or a mammalian cell therewith by well-known methods. In the case of carrying out the transformation, a more preferable system is exemplified by the method for integrating the gene in the chromosome, in view of achieving stability of the gene. However, an autonomous replication system using a plasmid can be conveniently used. Introduction of the DNA vector into the host cell can be carried out by standard methods such that described in "Molecular Cloning: A Laboratory Manual" (ed. by Sambrook et al., Cold Spring Harbor Laboratory Press, Cold Spring Harbor, N.Y., 1989.) Concretely, calcium phosphate transfection, DEAE-dextran-mediated transfection, microinjection, cation lipid-mediated transfection, electroporation, transduction, scrape loading, ballistic introduction and infection can be employed.

(Producing Polypeptide or Peptide)

Using an expression vector as a DNA vector for transduction of the above-described transformant, a polypeptide or a peptide according to the present invention can be provided. A transformant, transformed with a DNA expression vector comprising the above-described polynucleotide, is cultured under well-known culture conditions suitable for each host. Culturing may be conducted by using indicators, such as a function of the polypeptide or a peptide according to the present invention that is expressed by the transformant, particularly at least the activity to induce and/or activate CTL, or the peptide or the amount of the peptide produced in the host or outside of the host. Subculturing or batch culturing may be also carried out using an amount of the transformant in the culture as an indicator.

A peptide according to the present invention can be produced by a general method known in peptide chemistry. For example, "Peptide Synthesis (Maruzen) 1975" and "Peptide Synthesis, Interscience, New York, 1996" are exemplified. However, any widely known method can be used.

A polypeptide or peptide according to the present invention can be purified and collected by a method, such as a gel filtration chromatography, an ion column chromatography, an affinity chromatography, and the like, in combination, or by fractionation means on the basis of a difference in solubility using ammonium sulfate, alcohol, and the like, using a CTL-activating ability of the polypeptide or the peptide as an indicator. More preferably used is a method, wherein the polypeptide or the peptides are specifically adsorbed and collected by using polyclonal antibodies or monoclonal antibodies, which are prepared against the polypeptide or the peptides based on the information of their amino acid sequences.

(Antibody)

An antibody according to the present invention is prepared by using the above-described polypeptide or peptide as an antigen. An antigen may be the above-described polypeptide or peptide itself, or its fragment that is composed of at least 5, more preferably at least 8 to 10 amino acids. In order to prepare the antibody specific to the above-described polypeptide or peptide, a region consisting of the amino acid sequence intrinsic to the above-described polypeptide or peptide is desirably used. The amino acid sequence is not necessarily homologous to the amino acid sequence of the polypeptide or the peptide, but is preferably a site exposed to outside of a stereo-structure of the polypeptide or the peptide. In such a case, it is sufficient that the amino acid sequence of the exposed site is consecutive in the exposed site, even if it may be discrete in its primary structure. The antibody is not limited as long as it binds or recognizes the polypeptide or the peptide immunologically. The presence or absence of the binding or the recognition can be determined by a well-known antigen-antibody binding reaction.

In order to produce an antibody, a well-known method for antibody production can be employed. For example, the antibody is obtained by administration of the polypeptide or peptide according to the present invention to an animal in the presence or absence of an adjuvant with or without linking such to a carrier so as to induce humoral immunity and/or cell-mediated immunity. Any carrier can be used as long as it is not harmful to the host. For example, cellulose, a polymerized amino acid, albumin, and the like are exemplified, but not limited thereto. As an animal used for immunization, a mouse, rat, rabbit, goat, horse, and so on, is preferably used.

A polyclonal antibody can be obtained from serum of an animal subjected to the above-described immunological means by a well-known method for collecting antibodies. A preferable means is exemplified by immunoaffinity chromatography.

A monoclonal antibody can be produced by collecting antibody-producing cells (for example, a lymphocyte derived from a spleen or a lymph node) from the animal subjected to the above-described immunological means, followed by introducing a well-known transformation means with a permanently proliferating cell (for example, myeloma strain such as P3/X63-Ag8 cells.) For example, the antibody-producing cells are fused with the permanent proliferating cells by a well-known method to prepare hybridomas. Then, the hybridomas are subjected to cloning, followed by selecting ones producing the antibody that recognizes specifically the above-described polypeptide or peptide to collect the antibody from a culture solution of the hybridoma.

The polyclonal antibody or the monoclonal antibody thus obtained, which recognizes and binds to the above-described polypeptide or peptide, can be utilized as an antibody for purification, a reagent, a labeling marker and so on.

(Screening and Compound Obtained by Screening)

The above-described polypeptide or peptide, the polynucleotide encoding the same and the complementary strand thereof, the cell transformed based on the information concerning the amino acid sequence and nucleotide base sequence, or the antibody immunologically recognizing the same provide an effective means for screening a substance capable of inducing and/or activating CTL, when using them solely or in combination with each other. The screening method can be constructed utilizing a well-known screening system. For example, as shown in Examples herein, using a system in which the activation of CTL by the antigen-presenting cells that are pulsed with the tumor antigen peptide, is measured on the basis of the amount of IFN-γ production from CTL. Addition of a test substance to the system allows one to select the substance inducing and/or activating CTL and the substance enhancing the induction and/or the activation. This system describes one screening method, but the screening method according to the present invention is not limited thereto.

A compound obtained by the above-described screening method is also part of the present invention. The compound may be a compound enhancing the recognition of the polypeptide or the peptide by CTL through an interaction with the polypeptide or the peptide according to the present invention, and/or HLA-A2. Further, it may be a compound enhancing the expression of the polynucleotide according to the present invention through an interaction with the polynucleotide.

The compound thus selected can be used in a pharmaceutical composition by selecting ones having both biological usefulness and low toxicity.

(Pharmaceutical Composition)

The polypeptide or peptide according to the present invention can be used for activating and/or inducing the HLA-A2-restricted tumor-specific cytotoxic T lymphocytes, as a tumor antigen or a tumor antigen peptide. In other words, the method for inducing CTL, which is characterized in that the above-described polypeptide or peptide is used, and a inducer of CTL comprising the above-described polypeptide or peptide are included in the scope of the present invention.

The polypeptide or the peptide according to the present invention, the polynucleotide encoding the polypeptide and the complementary strand thereof, the recombinant vector prepared based on the information of their amino acid sequences and nucleotide base sequences, the cell transformed with the recombinant vector, or the antibody immunologically recognizing the polypeptide or the peptide, the compound enhancing the recognition of the polypeptide or the peptide by CTL through interaction with the polypeptide or the peptide, and/or HLA-A2, or the compound enhancing expression of the polynucleotide through interaction therewith can used a pharmaceutical composition comprising at least one species thereof, when using them solely or in combination with each other.

Concretely, for example, composition consisting of the polypeptide or the peptide according to the present invention, and the pharmaceutical composition comprising the polypeptide or the peptide according to the present invention can be used as a so-called anti-cancer vaccine. In such a case, in order to activate the cell-mediated immunity, the polypeptide or the peptide according to the present invention can be used in the presence or absence of an adjuvant with or without linking such to a carrier. Any carrier can be used as long as it is not harmful to the human body. For example, cellulose, a polymerized amino acid, or albumin is exemplified, but the carrier is not limited thereto. A dosage form is properly chosen from those to which the well-known means for preparing a polypeptide or a peptide are applied. The amount thereof to be administered depends on a degree of recognition of the peptide by CTL, and is generally 0.01 mg to 100 mg/day/adult human body, preferably 0.1 mg to 10 mg/day/adult human body as an amount of active substance. Such an amount is administered once every several days or every several months.

Alternately, an effective action of an anti-cancer vaccine can also be obtained by collecting a mononuclear cell fraction from the peripheral blood of a patient, and culturing the fraction with a peptide according to the present invention, followed by returning the mononuclear cell fraction, in which CTL are induced and/or activated, back into the blood of the patient. Culture conditions, such as the concentration of mononuclear cells and the concentration of the polypeptide or the peptide according to the present invention when they are cultured, can be readily determined. Further, a substance, such as interleukin 2 (IL-2) having an ability to induce the growth of lymphocytes may be added to the culture.

In the case of using the polypeptide or the peptide according to the present invention as an anti-cancer vaccine, using even only one polypeptide or one peptide is effective as an anti-cancer vaccine. However, plural kinds of the above-described polypeptide or peptide can be used in combination. CTL of the cancer patient is the population of cells recognizing various tumor antigens, so that using plural kinds of polypeptides or peptides as an anti-cancer vaccine may give a higher effect than using only one kind.

The above-described composition, inducer of the cytotoxic T lymphocytes, anti-cancer vaccine and pharmaceutical composition are useful for treatment of a cancer disease such as pancreatic cancer, colon cancer, or stomach cancer.

In addition, the polynucleotide encoding the polypeptide according to the present invention and the complementary strand thereof are also useful for gene therapy of a cancer disease such as pancreatic cancer, colon cancer, or stomach cancer.

A method in which these polynucleotides are present in a vector and directly introduced in vivo, and a method in which cells are collected from a donor followed by introducing polynucleotides present in a vector in vitro, can be both utilized. Retrovirus, adenovirus, and vaccinia virus exemplify the vectors, and retrovirus-related ones are preferred. Needless to say, these viruses show deficiency for replication. The amount of administration thereof can depend on the degree of recognition by CTL of the polypeptide encoded by the polynucleotide. Generally, as a DNA content encoding the tumor antigen peptide according to the present invention, the amount ranges from 0.1 μg to 100 mg/day/adult human body, preferably 1 μg to 50 mg/day/adult human body. This amount is administered once every several days or every several months.

(Measuring Method for Diagnosis and Reagent)

The polypeptide or the peptide according to the present invention, the polynucleotide encoding the polypeptide and the complementary strand thereof, and the antibody immunologically recognizing the polypeptide or the peptide can be used independently for a diagnostic marker and a reagent etc. The present invention also provides a reagent kit comprising one or more containers in which one or more species thereof are present. For the preparation thereof, it is sufficient to use a well-known means for their preparation according to each of polypeptide or peptide, polynucleotide, or antibody.

Diagnostic means for a disease related to expression or activity of the polypeptide or the peptide according to the present invention can be carried out, for example, utilizing the interaction or reactivity with the polynucleotide encoding the polypeptide, by determining the existing amount of the corresponding nucleic acid molecule, and/or determining a distribution of the polypeptide or the peptide in an individual living body, and/or determining a presence of the polypeptide or the peptide, and the existing amount in a sample derived from the individual body. In other words, measurement is carried out quantitatively or qualitatively for the polypeptide or the peptide according to the present invention or the polynucleotide encoding the same as the diagnostic marker. As a method for quantitative or qualitative measurement of the polypeptide or the peptide or the nucleic acid encoding the same, which are present in the sample, a well-known method can be utilized. Radioimmunoassay, competitive binding assay, Western blotting analysis, ELISA, and the like exemplify such a method. In addition, the nucleic acid molecule can be detected and quantified at an RNA level by using, for example, amplification, polymerase chain reaction (PCR,) RT-PCR, RNase protection, Northern blotting method, and other hybridization methods.

The sample subjected to measurement is exemplified by the cells derived from an individual human body present in for example, blood, urine, saliva, spinal fluid, tissue biopsy, or autopsy material, and the like. The nucleic acid molecule subjected to measurement is obtained from the each sample described above by a well-known method for nucleic acid preparation. For the nucleic acid molecule, genomic DNA can be directly used for detection, or it may be enzymatically amplified by using PCR or any other amplification method before the analysis. RNA or cDNA may be similarly used. In comparing with a normal genotype, a deletion or insertion can be detected in accordance with a size change of an amplification product. Hybridizing the amplified DNA with the labeled DNA encoding the above-described polypeptide can identify point mutations.

Detecting mutation of, reduction of, and increase in the polypeptide according to the present invention and the DNA encoding the polypeptide by the above-described measuring method, makes it possible to diagnose diseases, to which the polypeptide is associated, such as pancreatic cancer, colon cancer, or stomach cancer.

EXAMPLES

The present invention will be illustrated more concretely with the following examples, but is not limited thereto.

Example 1

Establishment of HLA-A2-Restricted CTL

The HLA-A2-restricted tumor-specific cytotoxic T lymphocyte line was established from tumor infiltrating lymphocytes (TIL) of a colon tumor patient (HLA-A0207/3101, HLA-B46/51, HLA-Cw1) (Int. J. CANCER, 81:459-466, 1999; J. Immunol., 163:4994-5004, 1999.) Specifically, TIL obtained from the colon tumor patient was cultured for along period up to 50 days or longer by adding 100 U/ml of recombinant human interleukin 2 (IL-2.) Every 7 days, a portion of TIL activated by IL-2 was collected and cultured together with various kinds of tumor cells or normal cells to assay its CTL activity by measuring the produced IFN-γ and by measuring $^{51}$Cr released from the cancer cells (J. Immunol., 163: 4994-5004, 1999.) IFN-γ was measured by an enzyme-linked immunosorbent assay (ELISA). At day 58 after the start of the culture, OK-CTLp, which is one of sublines showing HLA-A2-restricted tumor-specific CTL activity, was obtained. OK-CTLp obtained is a cell population in which 80% of the cells have a phenotype of CD3$^+$CD4$^-$CD8$^+$ and 20% of the cells have a phenotype of CD3$^+$CD4$^+$CD8$^-$. Using OK-CTLp as an effector cell and culturing it together with various kinds of cells that are used as a target cell, such as a tumor cell, the cytotoxicity to the target cell and activation of OK-CTLp were measured using the $^{51}$Cr-release test and by using IFN-γ production as an indicator, respectively. The results are each presented in FIG. 1 and FIG. 2.

Figure 2:
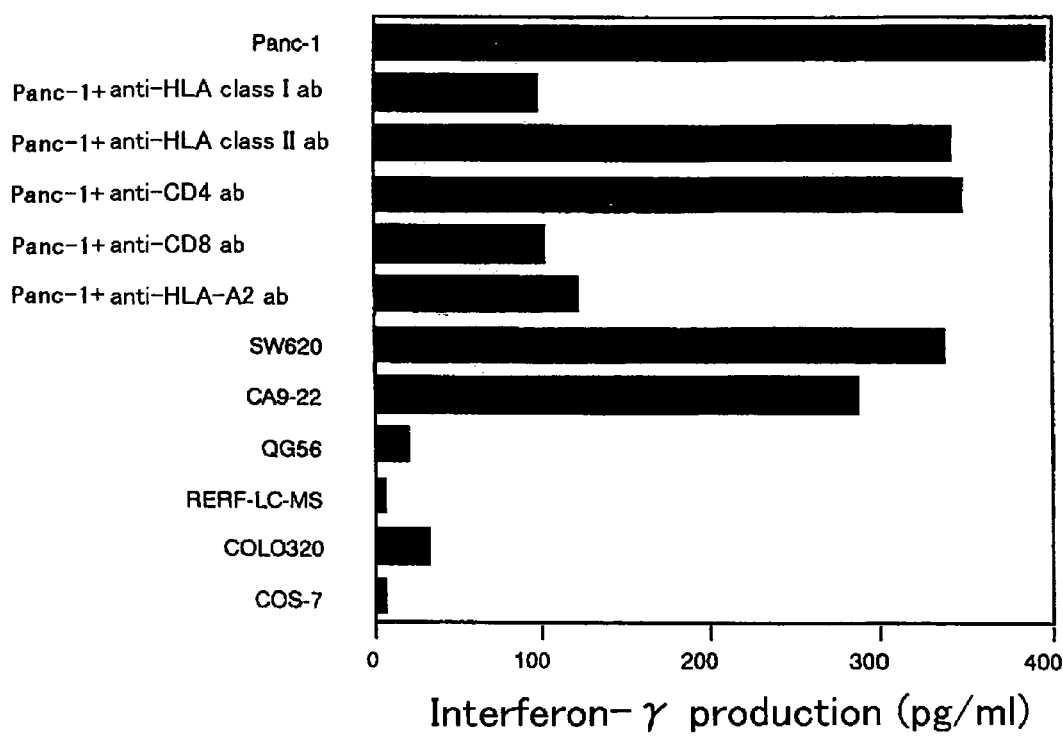
FIG. 2 illustrates that recognition of the human pancreatic adenocarcinoma cell line Panc-1 by OK-CTLp and interferon-γ production as a result thereof is an HLA-A2-restricted event.

OK-CTLp obtained, as shown in FIGS. 1 and 2, recognized HLA-A0201$^+$Panc-1 pancreatic adenocarcinoma cell, SW620 colon adenocarcinoma cell, HLA-A0206$^+$KE3 esophageal squamous-cell carcinoma (SCC) cell and HLA-A0207$^+$CA9-22 oral SCC cell to produce IFN-γ and represent sufficient cytotoxicity. However, no cytotoxicity was shown against HLA-A2$^-$ tumor cells, such as QG56 lung adenocarcinoma cell, RERF-LC-MC lung adenocarcinoma cell, and COLO320 colon adenocarcinoma cell, and autologous Epstein-Barr virus transformed B cell (EBV-B) and autologous phytohemagglutinin (PHA)-blastoid T cells both derived from the normal cells. Further, OK-CTLp lysed all of the HLA-A2$^+$ tumor cells tested (R27 breast cancer cell, HAK-2 primary hepatocellular carcinoma cell, SK-MEL-5 melanoma cell, and SF126 astrocytoma cell, which are HLA-A0201$^+$, and HLA-A0206$^+$ PC9 lung adenocarcinoma cell, and 1-87 lung adenocarcinoma cell and OMC-4 cervical SCC cell, which are HLA-A0207$^+$.) The CTL activity was inhibited by an anti-HLA class I monoclonal antibody (mAb), an anti-CD8 mAb or an anti-HLA-A2 mAb, but not inhibited by other mAbs (FIG. 2.) This result revealed that OK-CTLp recognizes the above-described tumor cells in a HLA-A2-restricted manner and shows cytotoxicity.

Meanwhile, the genotype of the HLA class I alleles of the above-described tumor cells has been disclosed (J. Immunol., 163:4994-5004, 1999.) The serotype of the HLA class I of the above-described patients was determined by applying a conventional method using the peripheral blood mononuclear cells (PBMC). In addition, the HLA-A2 subtype was determined by a sequence-specific oligonucleotide probe method and direct DNA sequencing. The phenotype of OK-CTLp was analyzed by direct immunofluorescence analysis using anti-CD3 mAb, anti-CD4 mAb, or anti-CD8 mAb (made by Nichirei) or anti-TCRαβ mAb (WT31, Becton Dickinson), which were labeled with fluorescein isothiocyanate (FITC). In addition, the antibodies used to analyze for HLA-A2 restriction and specificity of OK-CTLp were anti-HLA class I mAb (W6/32, IgG2a,) anti-HLA-A2 mAb (BB7.2, IgG 2b,) anti-CD8 mAb (Nu-Ts/c, IgG2a,) anti-HLA class II mAb (H-DR-1, IgG2A,) and anti-CD4 mAb (Nu-Th/i, IgG1.) Anti-CD13 mAb (MCS-2, IgG2a) and Anti-CD14 mAb (JML-H14, IgG1) were used as an isotype-matching control mAb.

Example 2

Isolation and Identification of cDNA Clone Encoding Tumor Antigen

A gene encoding the tumor antigen of the Panc-1 tumor cell recognized by OK-CTLp was isolated and identified according to the well-known gene expression cloning method (J. Immunol., 163:4994-5004, 1999.) Specifically, poly(A)$^+$ RNA of the Panc-1 tumor cells was converted to cDNA, and ligated with a SalI adapter so as to insert into the expression vector pCMV-SPORT-2 (Invitrogen Corp.)

cDNAs of HLA-A0207, HLA-A2402, or HLA-A2601 were obtained by reverse transcriptase polymerase chain reaction (RT-PCR) and cloned into the eukaryote expression vector pCR3 (Invitrogen Corp.)

200 ng of the above-described plasmid DNA pool or clones of Panc-1 cell cDNA library was mixed with 200 ng of the cDNA of HLA-A0207 in 100 μl of Opti-MEM (Invitrogen Corp.) for 30 min. 50 μl of this mixture was added to COS-7 cells ($5 \times 10^3$) and incubated for 6 h in a 96-well U-bottom type microculture plate (Nunc Corp.) for co-tranduction. Then, RPMI-1640 culture medium containing 10% FCS was added to and culturing was carried out for 2 days, followed by the addition of OK-CTLp ($5 \times 10^4$) to each well. After a further 18 h incubation, 100 μl of the supernatant was collected and IFN-γ production was measured thereon by ELISA. In this case, using COS-7 cells to which the gene had not been transfected as a target, IFN-γ production by OK-CTLp was examined and the value of IFN-γ produced was subtracted as a background from that of each measurement. As a result, seven cDNA clones were obtained, which enhanced IFN-γ production by OK-CTLp through recognition by OK-CTLp.

The nucleotide sequence of the seven cDNA clones obtained was determined by dideoxynucleotide sequencing method using a DNA sequencing kit (Perkin Elmer Corp.) and using an ABI PRISM™377DNA sequencer (Perkin Elmer Corp.) In addition, the amino acid sequence encoded by each clone was deduced from the nucleotide base sequence. Also, a homology search of the nucleotide base sequence of these clones was conducted through accessing GenBank. The results are presented in the above-described Table 1. With regard to clone 3 among the seven cDNA clones (clones 1 to 7) obtained, the sequence of an initial clone, which was obtained by the gene expression cloning method described above, was 25 bp shorter at the 5'-terminal region than that of WHSC2 showing high homology, so that full-length cDNA was obtained from the cDNA library of the Panc-1 cell by a standard colony hybridization method using the clone labeled with $^{32}P$ as a probe.

Figure 3:
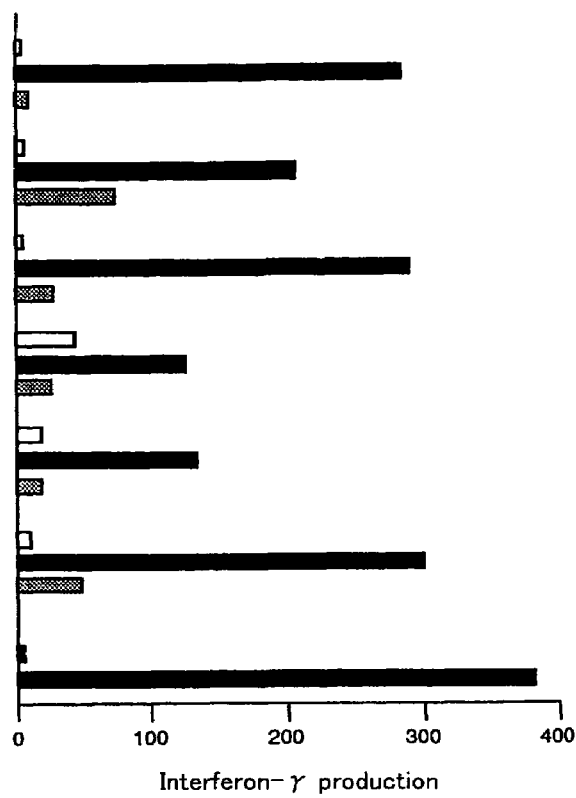
FIGS. 3A-3B illustrate that OK-CTLp recognizes COS7 cells, in which each of cDNA clones 1 to 6 (FIG. 3A) and cDNA clone 7 (FIG. 3B), obtained from the human pancreatic adenocarcinoma cell line Panc-1, was coexpressed with HLA-A2, in an HLA-A2-restricted manner.
Figure 3:
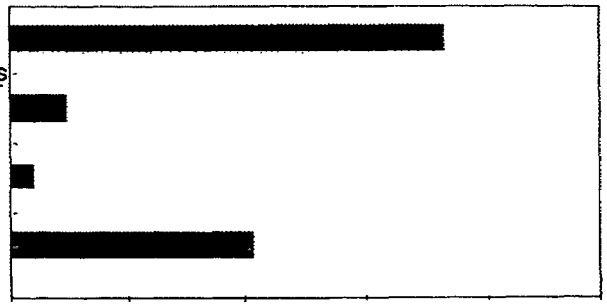
Figure 4:
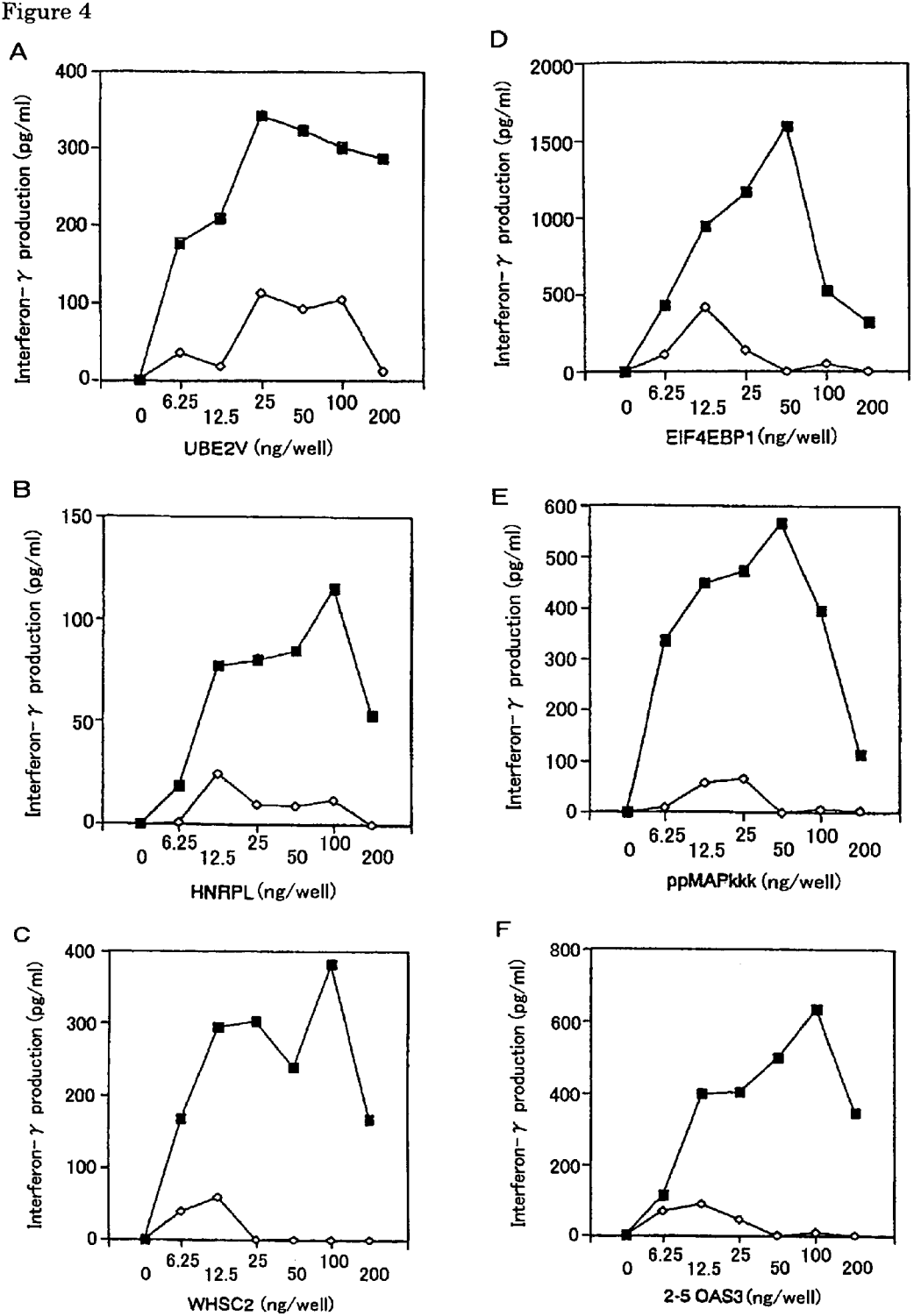
FIGS. 4A-4F illustrate that cDNA clones 1 to 6, obtained from the human pancreatic adenocarcinoma cell line Panc-1, are recognized by OK-CTLp in a dose-dependent manner.
Figure 5:
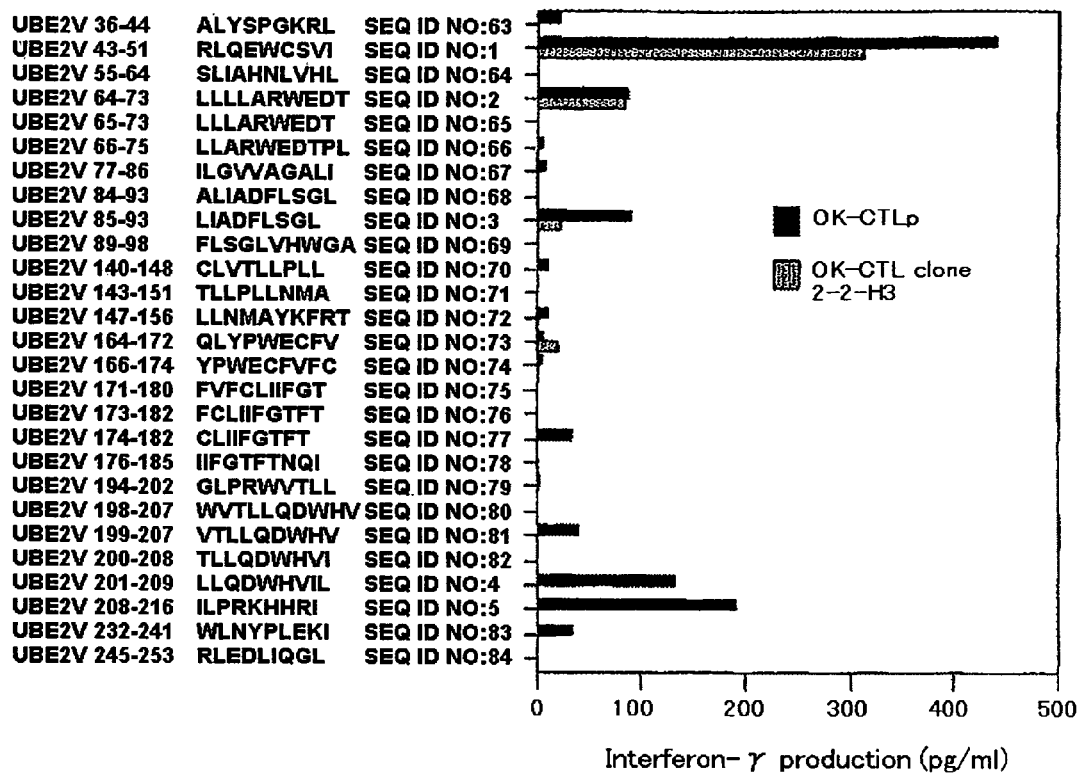
FIG. 5 illustrates that OK-CTLp or OK-CTL clone recognizes five peptides derived from a gene product of the tumor antigen gene 1 that is obtained from the human pancreatic adenocarcinoma cell line Panc-1, which has high homology with UBE2V.
Figure 6:
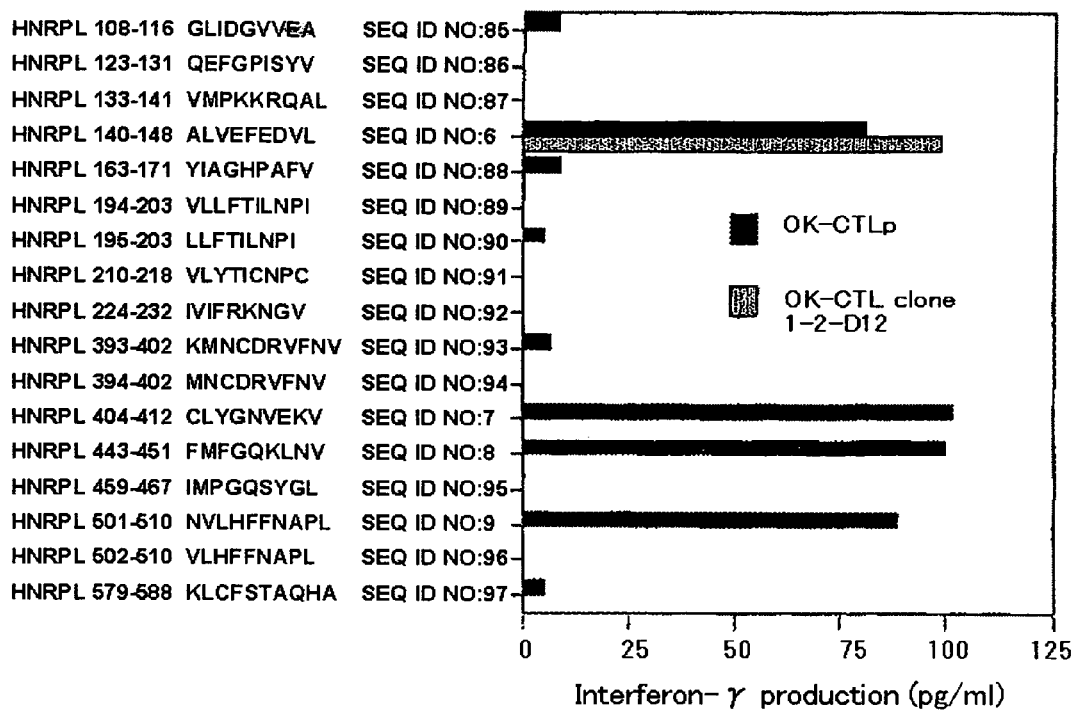
FIG. 6 illustrates that OK-CTLp or OK-CTL clone recognizes four peptides derived from a gene product of the tumor antigen gene 2 that is obtained from the human pancreatic adenocarcinoma cell line Panc-1, which has high homology with HNRPL.
Figure 7:
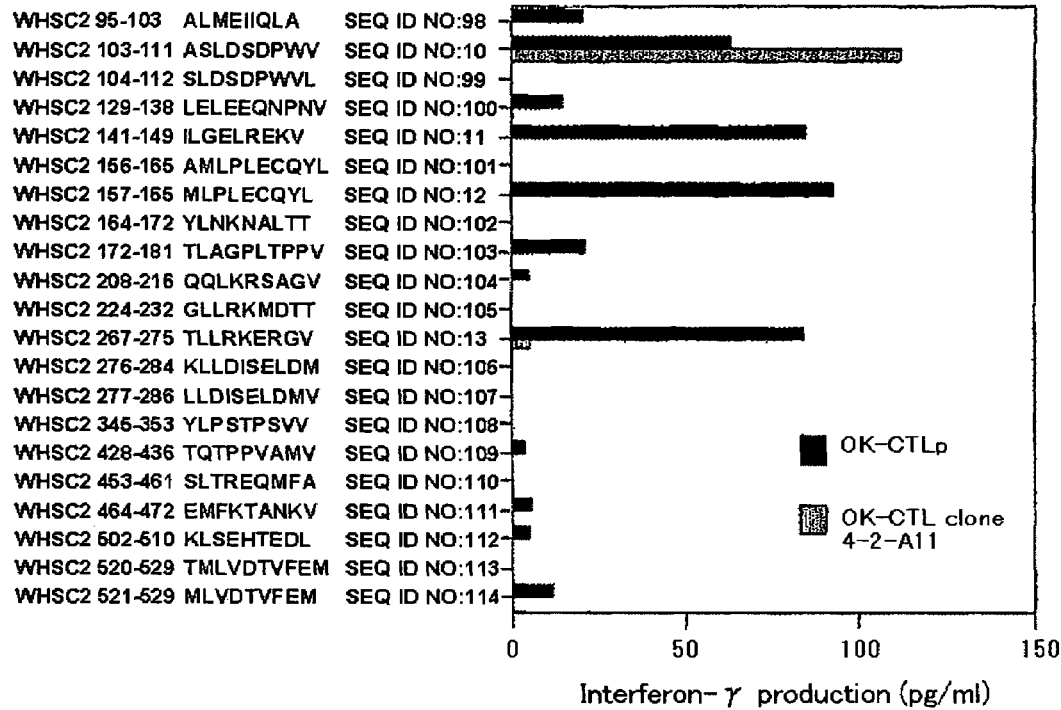
FIG. 7 illustrates that OK-CTLp or OK-CTL clone recognizes four peptides derived from a gene product of the tumor antigen gene 3 that is obtained from the human pancreatic adenocarcinoma cell line Panc-1, which has high homology with WHSC2.
Figure 8:
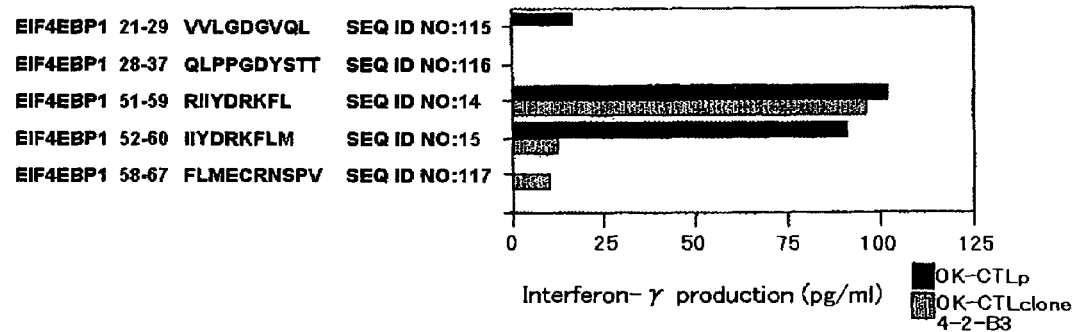
FIG. 8 illustrates that OK-CTLp or OK-CTL clone recognizes two peptides derived from a gene product of the tumor antigen gene 4 that is obtained from the human pancreatic adenocarcinoma cell line Panc-1, which has high homology with EIF4EBP1.
Figure 9:
FIG. 9 illustrates that OK-CTLp or OK-CTL clone recognizes three peptides derived from a gene product of the tumor antigen gene 5 that is obtained from the human pancreatic adenocarcinoma cell line Panc-1, which has high homology with ppMAPkkk.
Figure 10:
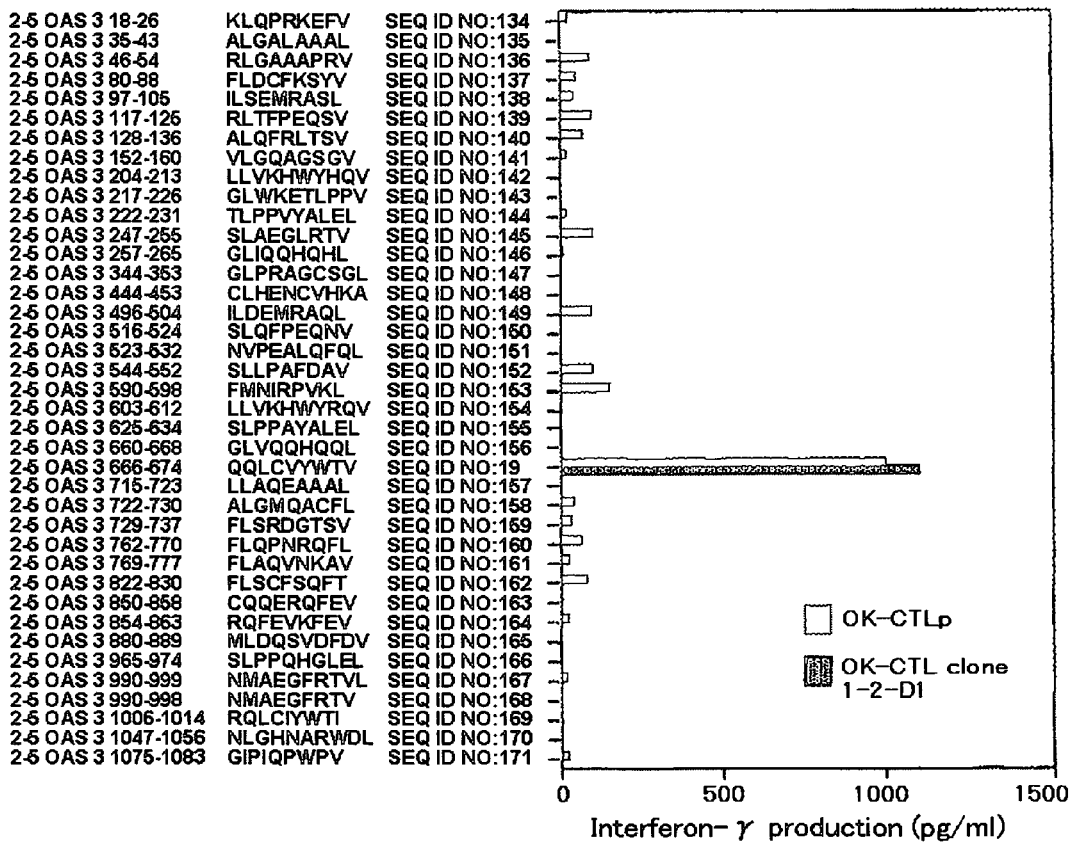
FIG. 10 illustrates that OK-CTLp or OK-CTL clone recognizes one peptide derived from a gene product of the tumor antigen gene 6 that is obtained from the human pancreatic adenocarcinoma cell line Panc-1, which has high homology with 2-5 OAS3.
Figure 11:
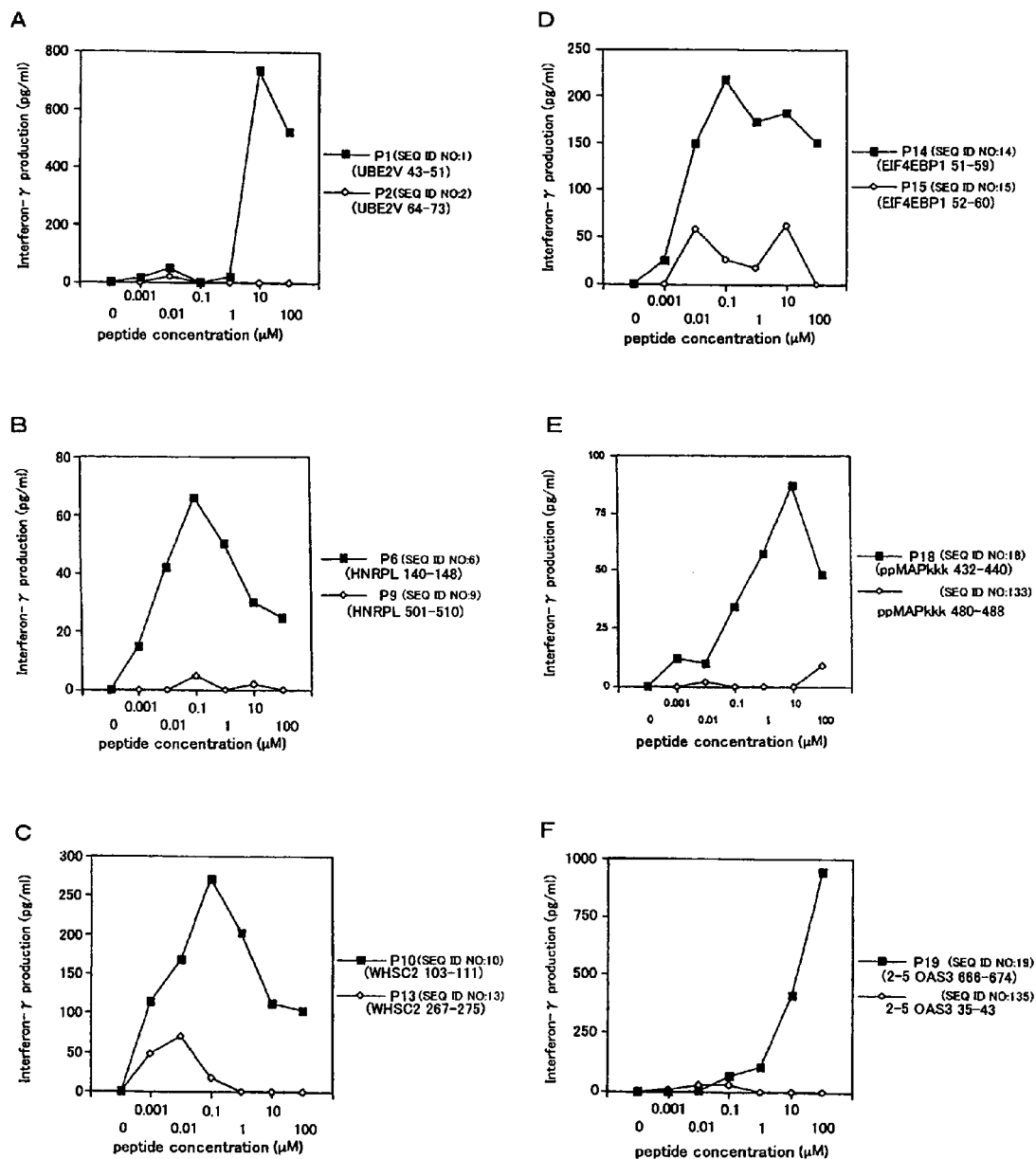
FIGS. 11A-11F illustrate representative peptides showing that the tumor antigen peptides, which are derived from products of the tumor antigen genes obtained from the human pancreatic adenocarcinoma cell line Panc-1, are recognized by OK-CTL clone in a dose-dependent manner.
Figure 12:
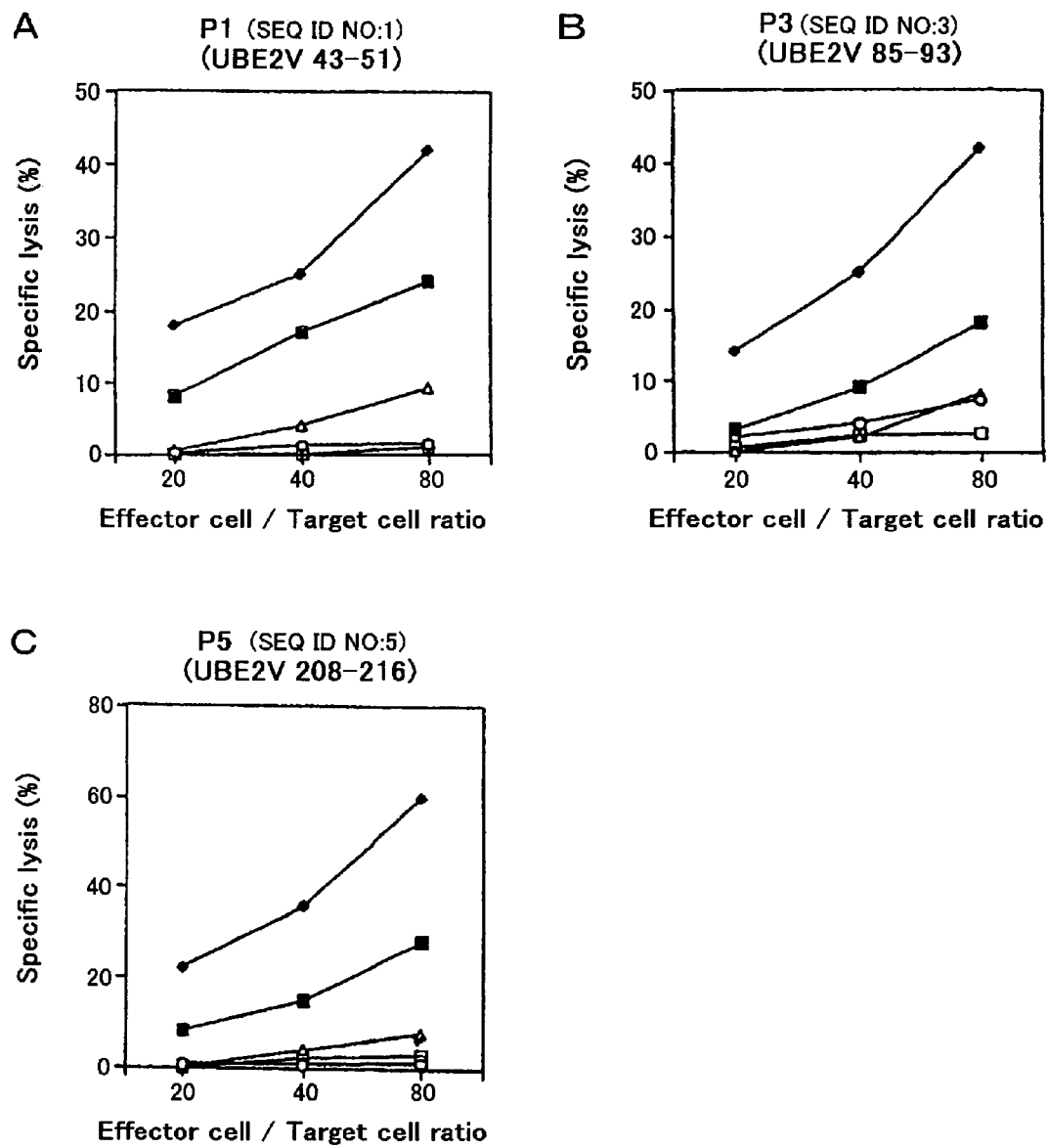
FIGS. 12A-12C illustrate that three peptides derived from a gene product of the tumor antigen gene 1 having high homology with UBE2V can induce CTL showing cytotoxicity against HLA-A2$^+$ tumor cell, from peripheral blood mononuclear cells of a cancer patient. The symbol —□— shows the human pancreatic adenocarcinoma cell line Panc-1 (HLA-A0201/1101,) —◆— shows the human colon adenocarcinoma cell line SW620 (HLA-A0201/2402,) —○— shows the HLA-A2$^-$ lung adenocarcinoma cell line RERF-LC-MS (HLA-A1101/1101,) —△— shows an EBV transformed B cell (HLA-A0207/3101,) and —□— shows a PHA blast of autologous T cell (HLA-A0207/3101.) These symbols are also used in the same manner in FIGS. 13 to 17 described below.
Figure 13:
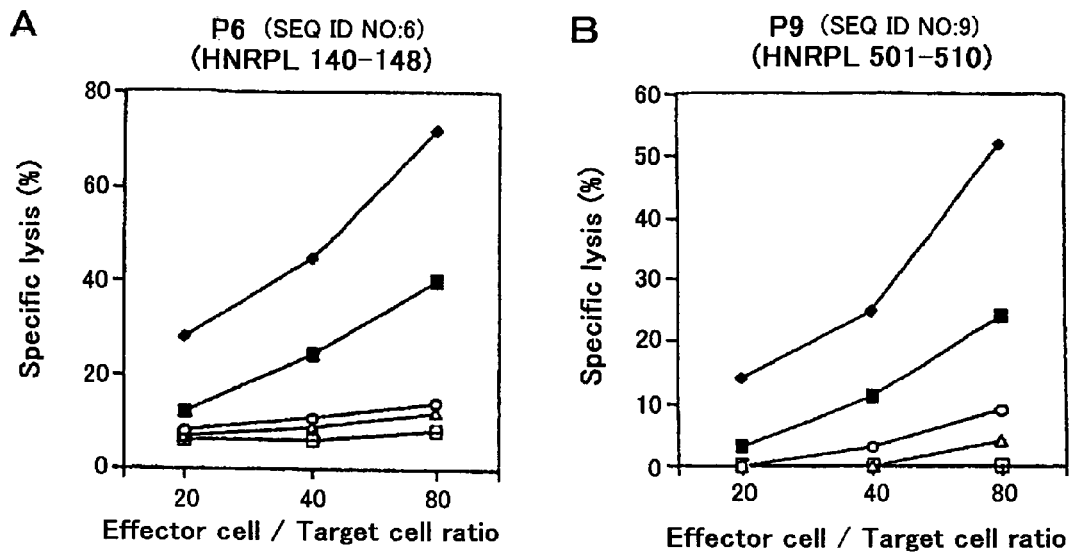
FIGS. 13A-13B illustrate that two peptides derived from a gene product of the tumor antigen gene 2 having high homology with HNRPL can induce CTL showing cytotoxicity against HLA-A2$^+$ tumor cell, from peripheral blood mononuclear cells of a cancer patient.
Figure 14:
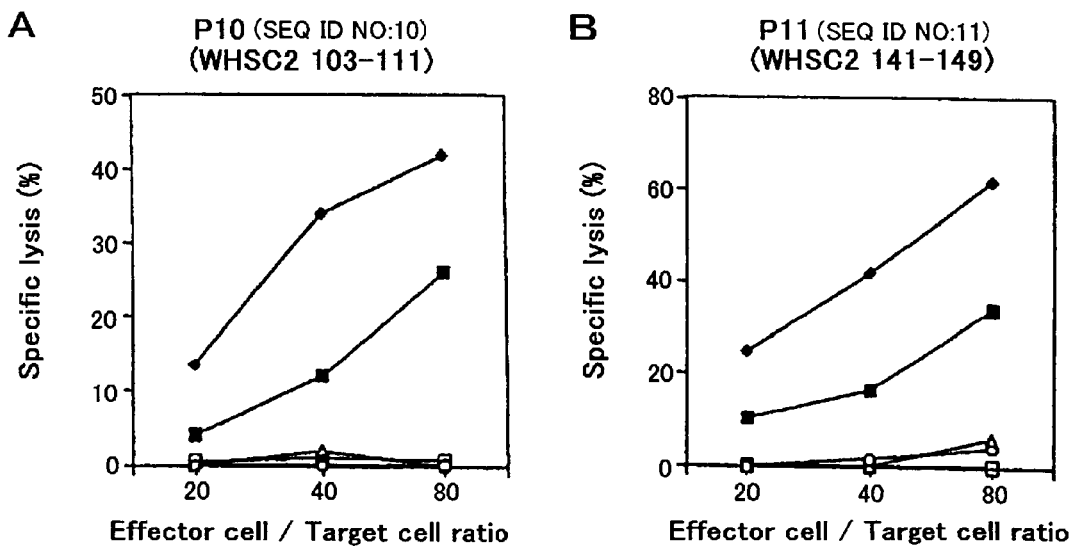
FIGS. 14A-14B illustrate that two peptides derived from a gene product of the tumor antigen gene 3 having high homology with WHSC2 can induce CTL showing cytotoxicity against HLA-A2$^+$ tumor cell, from peripheral blood mononuclear cells of a cancer patient.
Figure 15:
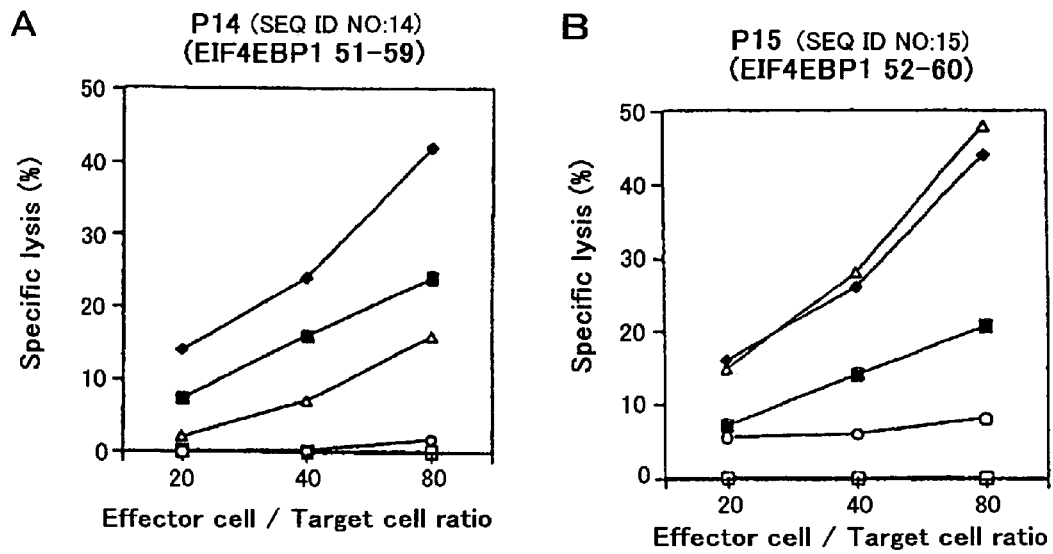
FIGS. 15A-15B illustrate that two peptides derived from a gene product of the tumor antigen gene 4 having high homology with EIF4EBP1 can induce CTL showing cytotoxicity against HLA-A2$^+$ tumor cell, from peripheral blood mononuclear cells of a cancer patient.
Figure 16:
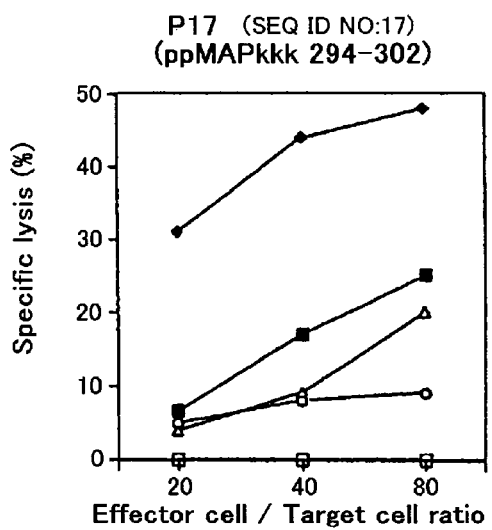
FIG. 16 illustrates that one peptide derived from a gene product of the tumor antigen gene 5 having high homology with ppMAPkkk can induce CTL showing cytotoxicity against HLA-A2$^+$ tumor cell, from peripheral blood mononuclear cells of a cancer patient.
Figure 17:
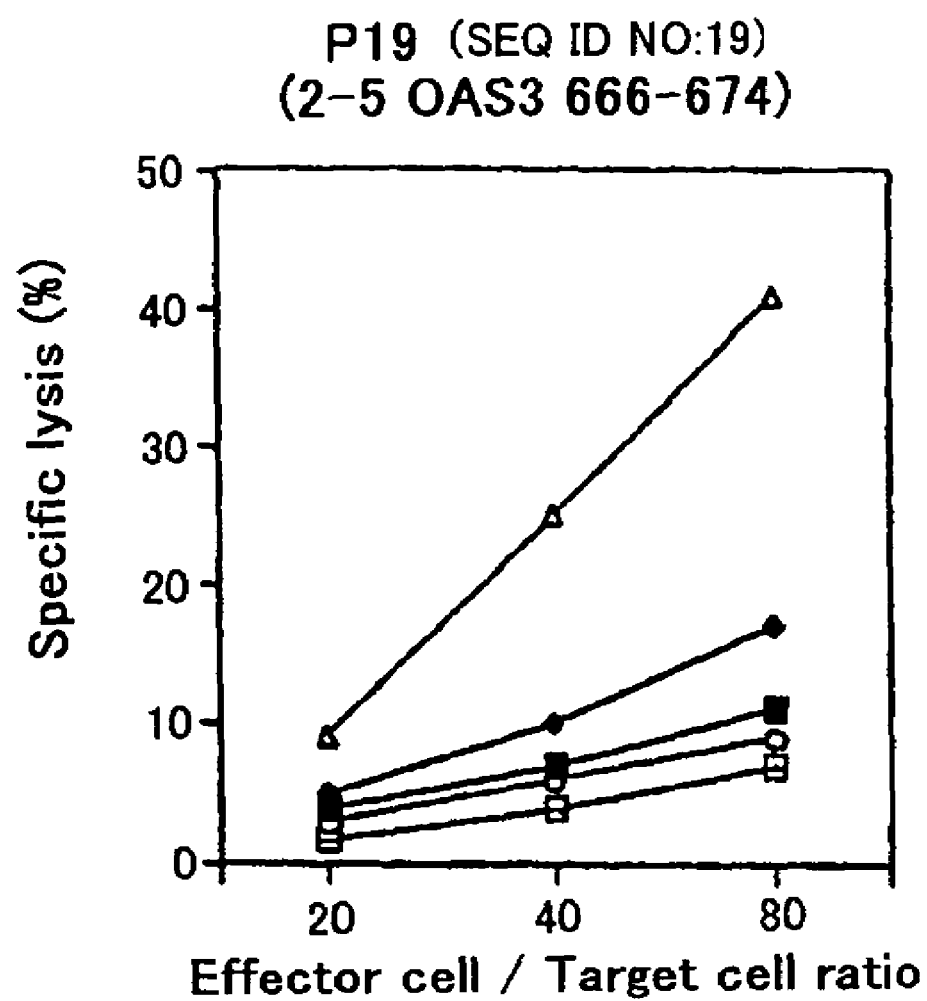
FIG. 17 illustrates that one peptide derived from a gene product of the tumor antigen gene 6 having high homology with 2-5 OAS3 can induce CTL showing cytotoxicity against HLA-A2$^+$ tumor cell, from peripheral blood mononuclear cells of a cancer patient.
Figure 18:
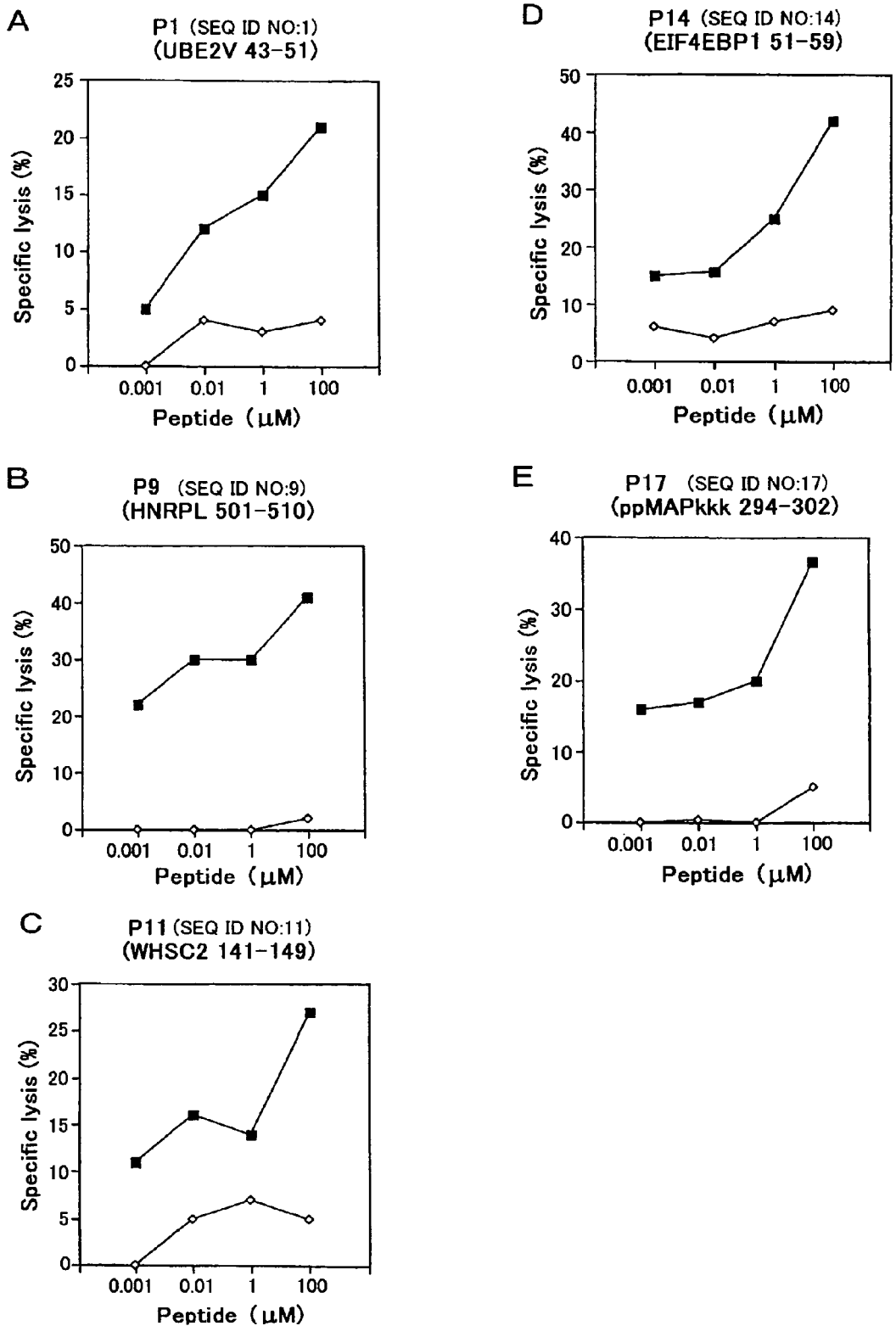
FIGS. 18A-18E illustrate that tumor antigen peptides can induce CTL, which shows cytotoxic activity in an HLA-A2-restricted manner and in a dose-dependent manner, from peripheral blood mononuclear cells of a cancer patient.

As shown in FIGS. 3A and 3B, clones 1 to 7 were each recognized by OK-CTLp to enhance IFN-γ production of OK-CTLp. However, OK-CTLP did not recognize COS-7 cells to which HLA-A0207 cDNA and the cDNA clone used as a negative control were cotransfected, or COS-7 cells to which any one of cDNA clones 1 to 7 and the cDNA of HLA-A2402 or HLA-A2601 were cotransfected, and did not show the IFN-γ production. When various concentrations of cDNA clones 1 to 6 were cotransfected into COS-7 cells together with 100 ng of HLA-A0207 cDNA or HLA-A2402 cDNA, IFN-γ production by OK-CTL was observed in a dose-dependent manner (FIGS. 4A to 4F.)

Expression of the mRNA of these genes was examined by Northern blotting analysis. The same expression pattern was observed except for gene 5. These genes are expressed commonly in the tumor cells and normal cells. However, expression levels in tumor cells such as Panc-1 cell, SW620 cell, and CA9-22 cell were significantly higher than that in normal cells, such as the T cell stimulated by PHA and a B cell transformed by Epstein-Barr virus (EBV-B). Expression of mRNA of gene 5 was barely detected under these experimental conditions. The reason may be that expression of gene 5 is rare as proven by the fact that colony hybridization using clone 5 labeled with $^{32}P$ gives only 3 clones from an about $1 \times 10^6$ cDNA library.

Example 3

Establishing OK-CTL Clone

Since CTL activated by recognizing the tumor antigen is a population of cells recognizing plural kinds of tumor antigens, the above-described OK-CTLp was subjected to cloning by limiting dilution culture (0.3, 0.5, 1, 2, and 4 cells/well) to obtain an OK-CTL clone (J. Immunol., 163:4994-5004, 1999.) These clones are those having CTL activity selected by culturing them together with COS-7 cells into which 100 ng/well of any one of the above-described seven cDNA clones and 100 ng/well of HLA-A0207 cDNA were cotransfected, or with the tumor cells, in a cell ratio of 1:1, and measuring IFN-γ production. Specifically, three hundred CTL clones were obtained from the parent line OK-CTLp by a limiting dilution culture. Eighty CTL clones among them had HLA-A2-restricted tumor-specific CTL activity and expressed the phenotype of CD3$^+$ CD4$^-$ CD8$^+$ and TCR αβ$^+$. Among them, 2, 3, 1, 3, 2, and 4 CTL clones showed reactivity to the COS-7 cells expressing clone 1, clone 2, clone 3, clone 4, clone 5, and clone 6, respectively. In other words, it was revealed that the tumor antigen recognized by CTL differs in accordance with the CTL clones. Table 4 shows data of fifteen typical CTL clones. This suggested that OK-CTLp, i.e., CTL derived from the cancer patient, is a population of cells recognizing plural kinds of tumor antigens.

TABLE 4

| | cDNA expressed in COS-7 cell together with HLA-A0207 cDNA | | | | | | | |
|---|---|---|---|---|---|---|---|---|
| CTL clone | clone 1 (UBE2V) | clone 2 (HNRPL) | clone 3 (WHSC2) | clone 4 (EIF4EBP1) | Clone 5 (ppMAPkkk) | clone 6 (2-5 OAS3) | no cDNA | Panc-1 |
| 2-2-H3 | 110 | 0 | 0 | 0 | 0 | 0 | 0 | 340 |
| 2-1-H12 | 134 | 0 | 0 | 0 | 0 | 0 | 0 | 264 |
| 1-2-D7 | 0 | 200 | 0 | 0 | 0 | 0 | 0 | 235 |
| 1-2-D12 | 0 | >1000 | 0 | 0 | 0 | 0 | 0 | >1000 |
| 4-1-H8 | 0 | 133 | 0 | 0 | 0 | 0 | 0 | 84 |
| 4-2-A11 | 0 | 0 | 100 | 0 | 0 | 0 | 0 | 725 |
| 0.5-1-H12 | 0 | 0 | 0 | >1000 | 0 | 0 | 0 | >1000 |
| 0.5-1-D6 | 19 | 0 | 0 | 118 | 0 | 13 | 0 | 448 |
| 4-2-B3 | 0 | 0 | 0 | 95 | 0 | 0 | 0 | 100 |
| 2-1-F4 | 0 | 0 | 0 | 0 | >1000 | 0 | 0 | >1000 |
| 0.5-1-H2 | 0 | 0 | 0 | 0 | 81 | 0 | 0 | 122 |
| 0.5-1-D7 | 27 | 34 | 0 | 0 | 0 | 110 | 0 | 304 |
| 0.5-2-A4 | 0 | 0 | 0 | 0 | 0 | 113 | 0 | >1000 |

TABLE 4-continued

| | cDNA expressed in COS-7 cell together with HLA-A0207 cDNA | | | | | | | |
|---|---|---|---|---|---|---|---|---|
| CTL clone | clone 1 (UBE2V) | clone 2 (HNRPL) | clone 3 (WHSC2) | clone 4 (EIF4EBP1) | Clone 5 (ppMAPkkk) | clone 6 (2-5 OAS3) | no cDNA | Panc-1 |
| 1-2-D1 | 21 | 0 | 22 | 44 | 0 | 61 | 0 | 78 |
| 2-2-B4 | 0 | 0 | 0 | 0 | 0 | >1000 | 0 | >1000 |

Example 4

Preparation of Tumor Antigen Peptide and its CTL-Inducing Activity

In order to obtain the tumor antigen peptide derived from the seven tumor antigen genes, which were obtained in Example 2 and can induce CTL in a HLA-A2-restricted manner, a peptide having an HLA-A2 binding motif (a specific sequence) was searched for in the literature (J. Immunol., 152:163, 1994; Immunogenetics, 41:178, 1994,) and peptides of 9-mer to 11-mer, which were different from each other and suited to the motif obtained, was designed and synthesized based on the amino acid sequence encoded by the above-described genes 1 to 7 and the amino acid sequence of UBE2V, HNRPL, WHSC2, EIF4EBP1, ppMAPkkk, 2-5 OAS3, and CPSF having high homology with these genes. The purity of the peptides obtained was each 70% or higher.

Binding activity of the peptide to the HLA-A0201 molecule was tested using a T2 cell mutant strain (Cancer Res., 54:1071-1076, 1994.) The T2 cell expresses the HLA-A2 molecule on a cell surface without binding to a peptide, because of deficiency of TAP. Specifically, the synthesized peptide (10 µM) and the T2 cells were incubated at 26° C. for 3 h and, subsequently, incubated in 5% $CO_2$ and 95% air at 37° C. for 3 h. Thus, T2 cells, on whose surface the peptide was presented by HLA-A2, were obtained. The cells were incubated together with anti-HLA-A2 mAb (BB7.2) followed by staining with R-phycoerythrin linked F (ab')$_2$ rabbit anti-mouse immunoglobulin (Ig) (DAKO Corp.) Then, the expression pattern was analyzed by employing FACScan (Beckman Dickinson Corp.), which resulted in confirmation that HLA-A0201 molecules with the peptide were expressed on the cell surface.

In order to test for recognition of a peptide by CTL, the T2 cells previously pulsed with each peptide (10 µM) was used as a target cell (T), and OK-CTLp or OK-CTL clone was used as an effector cell (E). The target cell and the effector cell were incubated for 18 h, the supernatant collected, followed by measuring IFN-γ contained in the supernatant by an ELISA. In the case where OK-CTLp was used as the effector, an E/T ratio was set to 10:1. In the case where the OK-CTL clone was used, it was set to 2:1 to conduct the test. On the other hand, in case where the OK-CTL clone was used to test for the CTL activating ability of the peptide, the clone was used which recognized the gene product encoding the peptide being examined. Using IFN-γ production of OK-CTLp or OK-CTL clone against the T2 cells, which had not been pulsed with the peptide, as a background, subtraction was performed from each measurement value. The results were shown in FIGS. 5 to 10. FIG. 5, FIG. 6, FIG. 7, FIG. 8, FIG. 9, and FIG. 10 each show the result of the peptide derived from gene 1 and UBE2V, gene 2 and HNRPL, gene 3 and WHSC2, gene 4 and EIF4EBP1, and gene 5 and ppMAPkkk, and gene 6 and 2-5 OAS3.

Moreover, the various concentrations of each peptide were used for incubation together with the T2 cells to examine the CTL clone-activating ability, resulting in finding that the CTL clone can be activated by each peptide in a dose-dependent manner. Representative examples of peptides derived from gene 1 and UBE2V, gene 2 and HNRPL, gene 3 and WHSC2, gene 4 and EIF4EBP1, gene 5 and ppMAPkkk, and gene 6 and 2-5 OAS3 were presented in FIGS. 11A-11F, respectively. On the other hand, Table 5 shows peptides derived from gene 7 and CPSF. In Table 5, the peptide derived from EBV and the peptide derived from influenza virus are positive controls, which can activate CTL.

As the result of these experiments, it was revealed that the peptides shown in Table 2 described-above can activate OK-CTLp and/or OK-CTL clone to produce IFN-γ.

TABLE 5

| | IFN-γ production (pg/ml) Concentration of peptide | | | |
|---|---|---|---|---|
| Peptide | 0.1 µM | 1 µM | 10 µM | 50 µM |
| Derived from influenza virus | 0 | 93 | 693 | 35 |
| Derived from EBV | 119 | 390 | 371 | 117 |
| P20 | 344 | 643 | 0 | 34 |
| P21 | 428 | 501 | 81 | 195 |
| P22 | 254 | 1027 | 431 | 407 |
| P23 | 6360 | 0 | 345 | 160 |
| P24 | 728 | Detection limit or higher | 103 | 2 |
| P25 | 69 | 1569 | 25 | 122 |
| P26 | 141 | 418 | 1239 | 0 |
| P27 | 352 | 889 | 250 | 0 |
| P28 | 898 | Detection limit or higher | 0 | 144 |
| P29 | 0 | Detection limit or higher | 86 | 362 |
| P30 | 88 | 7001 | Detection limit or higher | Detection limit or higher |
| P31 | 443 | Detection limit or higher | Detection limit or higher | 314 |

Example 5

CTL Induction from Peripheral Blood Mononuclear Cells Derived from Cancer Patient by a Peptide Among the peptides that were able to enhance IFN-γ production from the OK-CTLP or OK-CTL clone in Example 4, those from P1 to P19 were examined for their ability to induce CTL from peripheral blood mononuclear cells derived from a cancer patient. The method for inducing CTL by a peptide was according to the well-known method (J. Exp. Med., 187:277-288, 1998; Cancer Res., 59:4056-4063, 1999.) Specifically, autologous peripheral blood mononuclear cells (PBMC) derived from a cancer patient, from whom OK-CTLp was obtained, were incubated together with the peptide (10 μM.) The cells were re-stimulated at day 10 and 14 after the start of culturing, using autologous PBMCs as an antigen presenting cell (APC) which were pulsed with 10 μM of the same peptide for 2 h and exposed to irradiation (30 gray.) At day 21 after the start of culturing, the cells were collected to test for surface phenotype. In addition, the cells were examined for the recognition of various target cells, using IFN-γ production measured by ELISA when they were cultured together with the target cells as an indicator. As a target cells, SW620 cell, CA9-22 cell, and Panc-1 cell, which are the HLA-A2⁺ tumor cells, were used. The result was shown in Table 6.

Moreover, CTL-activating ability of these 19 peptides was directly examined in a $^{51}$Cr-releasing test using toxicity to the target cells as an indicator. Specifically, the above-described PBMC, in which CTL was induced, was further recultured to proliferate in the presence of autologous APC, IL-2, and a corresponding peptide. At about day 21 to 28 after the start of reculturing, PBMC was collected and cytotoxicity thereof was tested again by measuring IFN-γ and by a 6-h $^{51}$Cr-releasing test. The results were shown in FIGS. 12 to 17. PBMC of the cancer patient, which was stimulated by these peptides, lysed the HLA-A2⁺ tumor cells. However, the autologous EBV-B cells and the T cells stimulated by PHA, both of which were derived from normal cells and were expressing HLA-A2, and the HLA-A2⁻ tumor cell RERF-

TABLE 6

IFN-γ production (pg/ml) from peripheral blood mononuclear cells in recognition of various target cells

| Peptide | MFI | QG56 (HLA-A26/26) | RERF-LC-MS (HLA-A11/11) | COLO320 (HLA-A24/24) | SW620 (HLA-A0201/24) | CA9-22 (HLA-A0207/24) | Panc-1 (HLA-A0201/11) |
|---|---|---|---|---|---|---|---|
| P1 | 571 | 0 | 26 | 50 | 235 | 81 | 492 |
| P2 | 607 | 0 | 0 | 5 | 53 | 0 | 0 |
| P3 | 910 | 0 | 0 | 44 | 188 | 58 | 289 |
| P4 | 1008 | 0 | 0 | 0 | 60 | 0 | 0 |
| P5 | 637 | 0 | 0 | 38 | 500 | 96 | 638 |
| P6 | 819 | 0 | 8 | 40 | 344 | 863 | 527 |
| P7 | 783 | 0 | 0 | 0 | 344 | 0 | 54 |
| P8 | 499 | 0 | 26 | 0 | 142 | 165 | 186 |
| P9 | 832 | 0 | 27 | 0 | 194 | 98 | 339 |
| P10 | 504 | 0 | 0 | 0 | 108 | 130 | 163 |
| P11 | 1089 | 0 | 0 | 0 | 893 | 62 | >1000 |
| P12 | 780 | 0 | 0 | 40 | 46 | 0 | 197 |
| P13 | 656 | 0 | 15 | 0 | 151 | 95 | 115 |
| P14 | 591 | 0 | 0 | 0 | 112 | 184 | 265 |
| P15 | 789 | 0 | 32 | 0 | 199 | 219 | 502 |
| P16 | 887 | 0 | 0 | 0 | 0 | 147 | 113 |
| P17 | 660 | 0 | 0 | 0 | >1000 | >1000 | 691 |
| P18 | 657 | 29 | 0 | 0 | >1000 | 70 | >1000 |
| P19 | 775 | 0 | 30 | 66 | 55 | 48 | 105 |
| no Peptide | 491 | 0 | 0 | 36 | 0 | 0 | 17 |

PBMC stimulated in vitro using P1, P3, P5, P6, P8, P9, P10, P11, P13, P14, P15, P17, or P18 among the 19 peptides recognized SW620 cells, CA9-22 cells and Panc-1 cells, which are the HLA-A2⁺ tumor cells, produced IFN-γ in a significant amount. However, the PBMC barely recognized the HLA-A2⁻ tumor cell. On the other hand, P2, P4, P7, P12, and P16 also induced CTL recognizing any one of the HLA-A2 tumor cells. PBMC stimulated by P19 recognized not only the tumor cells expressing HLA-A2, but also the tumor cells expressing other types of HLA. IFN-γ production from these CTL was inhibited by anti-HLA class I mAb, anti-CD8 mAb, or anti-HLA-A2 mAb, and not inhibited by other mAbs. In addition, when peripheral blood mononuclear cells (PBMC) were prepared from blood of two HLA-A0201⁺ patients (a colon cancer patient and a pancreatic cancer patient) to examine CTL induction by the peptides, the same result as above was obtained. In other words, it was found that the above-described peptides can induce HLA-A2-restricted CTL from the peripheral blood mononuclear cells of the patient.

Binding affinity of the peptides to HLA-A0201 molecule was expressed as a relative mean fluorescence intensity (MFI) of the HLA-A2 molecule. The MFI of positive and negative controls were 898 and 490, respectively. It can be supposed that binding affinity of a peptide to the HLA-A0201 molecule has no correlation with induction of CTL by the peptide.

LC-MS, were not lysed. However, PBMC stimulated by peptides P14, P15, and P17 also showed cytotoxicity to the autologous EBV-B cells. Moreover, PBMC stimulated by P19 showed high cytotoxicity to the autologous EBV-B cells. In addition, PBMC stimulated by these peptides showed cytotoxicity to the T2 cells, which was pulsed with the same peptide as that used for stimulation of PBMC, in a dose dependent manner. Typical examples are shown in FIGS. 18A-18E. From these above, it was found that the above-described peptides can induce CTL, which shows HLA-A2-restricted cytotoxicity, from the peripheral blood mononuclear cells of the cancer patient.

Example 6

CTL Induction from Peripheral Blood Mononuclear Cell of Patient by Peptide

For six peptides (P21, P22, P24, P26, P30, and P32) with a purity of 95% or higher among peptides from P20 to P32 derived from gene 7 and CPSF among the tumor antigen peptide obtained in Example 4, the activity to induce CTL in vitro from human peripheral blood mononuclear cells (PBMC) was examined using IFN-γ production as an indicator. PBMC used was prepared from each peripheral blood of sixteen HLA-A2-positive cancer patients (4 patients with pancreatic cancer, seven patients with stomach cancer, and 5 patients with colon cancer) and six healthy individuals. Specifically, $1\times10^5$ PBMC was added to each well of 96-well U-bottom type microculture plate (Nunc Corp.) and incubated together with 10 μM of each of the above-described peptides in 200l μl culture medium. The culture medium consisted of 45% RPMI-1640, 45% AIM-V (Invitrogen Corp.,) 10% fetal calf serum (FCS), 100 U/ml of human interleukin-2, and 0.1 μM MEM nonessential amino acid solution (Invitrogen Corp.). At day 4 and day 7 after the start of culturing, half of the culture medium was removed and replaced with the above-described composition containing each corresponding peptide. At day 10 after the start of culturing, the cells were collected and washed, followed by reacting with T2 cells, which were pulsed with each corresponding peptide, to measure the amount of IFN-γ produced.

Meanwhile, the above-described cells cultured for 10 days after stimulation by the peptide were further cultured for 10 days. The cytotoxicity of the obtained cells against the Panc-1 pancreatic adenocarcinoma cell (HLA-A2) was measured by the standard 6-h $^{51}$Cr-releasing test in an E/T ratio of 10:1. The results obtained are presented as % specific lysis (table 7). Together with this step, cytotoxicity against SSTW-9 tumor cell as the HLA-A2$^-$ tumor cell was measured to use as a background that was subtracted from the above-described result.

As a result, induction of HLA-A2-restricted CTL from PBMC by P21, P22, P23, P26, P30, and P32, which was specific to each peptide, was observed in patients of 31% (5/16,) 38% (6/16,) 25% (4/6,) 31% (5/16,) 44% (7/16,) and 7% (1/16) of the above-described sixteen patients, respectively. On the other hand, induction of CTL by P21 and P22 from the PBMC of healthy individuals was found in 50% (3/6) and 33% (2/6,) respectively. However, the other peptides did not induce CTL from the PBMC of healthy individuals (Table 7). The above-described CTL induced from PBMC of the cancer patients by using the peptide showed cytotoxicity against Panc-1 pancreatic adenocarcinoma cell, and also SW620 colon adenocarcinoma cell (HLA-A2/A24) and KWS stomach adenocarcinoma cell (HLA-A2), both of which are the HLA-A2$^+$ tumor cells. However, lysis was not observed in SSTW9 stomach adenocarcinoma cell (HLA-A24), which is the HLA-A2$^-$ tumor cell, or the PHA-blastoid T cells or the EBV-B transformed B cells, both of which express HLA-A2 and are not the tumor cells. Recognition of the tumor cell by the above-described CTL was inhibited by anti-HLA class I mAb, anti-CD8 mAb, or anti-HLA-A2 mAb, and not inhibited by other mAb.

TABLE 7

| Origin of PBMC | | INF-γ production (pg/ml)/% specific lysis | | | | | |
|---|---|---|---|---|---|---|---|
| | | P21 | P22 | P23 | P26 | P30 | P32 |
| pancreatic cancer patient | 1 | 0 | 0 | 0 | 0 | 0 | 0 |
| | 2 | 7 | 38/37 | 41/53 | 35/36 | 12 | 12 |
| | 3 | 0 | 0 | 0 | 0 | 0 | 0 |
| | 4 | 543/12 | 8 | 72/10 | 77/20 | 73/11 | 0 |
| stomach cancer patient | 5 | 0 | 0 | 0 | 53/11 | 0 | 0 |
| | 6 | 0 | 0 | 0 | 0 | 0 | 0 |
| | 7 | 0 | 0 | 46/10 | 0 | 0 | 0 |
| | 8 | 5 | 0 | 0 | 11 | 146/18 | 0 |
| | 9 | 1500</127 | 0 | 0 | 8 | 92 | 0 |
| | 10 | 0 | 0 | 0 | 0 | 46/26 | 0 |
| | 11 | 136/18 | 0 | 0 | 0 | 0 | 0 |
| colon cancer | 12 | 0 | 92/28 | 71/18 | 0 | 0 | 57/18 |
| | 13 | 0 | 179 | 138/10 | 0 | 41/12 | 0 |
| patient | 14 | 66/11 | 80/19 | 48 | 0 | 33/10 | 0 |
| | 15 | 0 | 5 | 14 | 40/12 | 0 | 0 |
| | 16 | 140 | 0 | 0 | 45 | 68 | 4 |
| healthy individuals | HD1 | 0 | 0 | 0 | 0 | 0 | 0 |
| | HD2 | 0 | 0 | 13 | 0 | 0 | 0 |
| | HD3 | 58 | 0 | 8 | 0 | 14 | 0 |
| | HD4 | 5 | 0 | 6 | 0 | 0 | 0 |
| | HD5 | 224 | 0 | 83 | 13 | 0 | 0 |
| | HD6 | 97 | 14 | 45 | 0 | 0 | 0 |

Example 7

Isolation and Identification of cDNA Encoding Tumor Antigen

Figure 19:
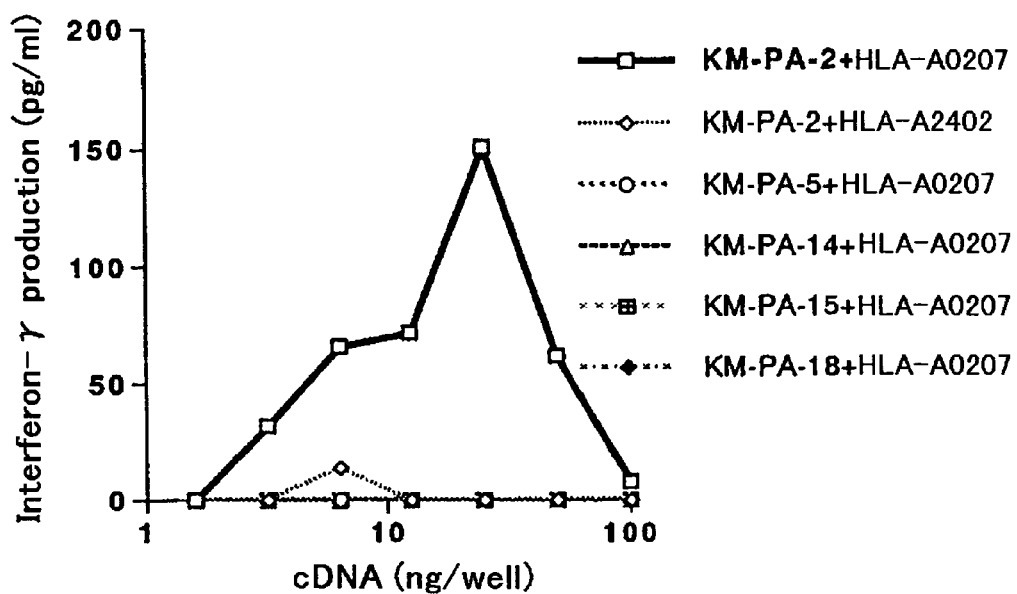
FIGS. 19A-19B illustrate that gene products of the tumor antigen genes KM-PA-2 (FIG. 19A) and KM-PA-4 (FIG. 19B), which were obtained from the human pancreatic adenocarcinoma cell line CFPAC-1, are recognized by OK-CTLp in an HLA-A2-restricted manner.
Figure 19:
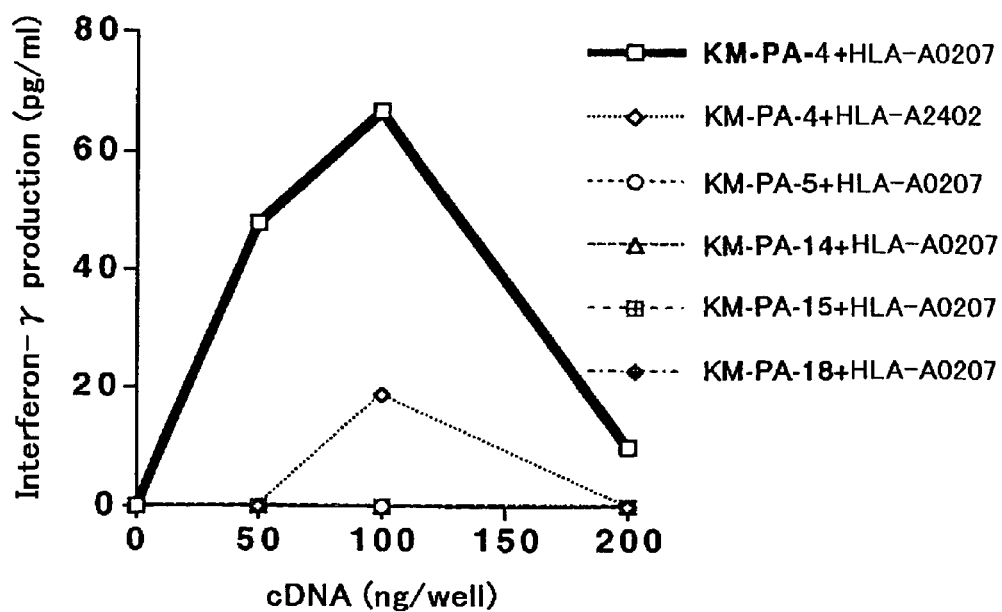

From the genes encoding the tumor antigens (Biochim. Biophys. Res. Commun., 281:936-944, 2001), which were detected by the SEREX (Serological Analysis of Recombinant cDNA Expression Libraries) method (Proc. Natl. Acad. Sci. USA, 92:11910-11813, 1995) and already reported, two tumor antigen genes, KM-PA-2 and KM-PA-4, which can activate HLA-A2-restricted CTL, were found by using the same method as that of Example 2. Specifically, cDNA clones each encoding KM-PA-2, KM-PA-4, KM-PA-5, KM-PA-14, KM-PA-15, or KM-PA-18 were packaged in pBluescript vector, and digested by EcoRI and XhoI to insert into pCMV-SPORT2. These cDNAs in various concentrations were each coexpressed in COS-7 cells together with HLA-A0207 or HLA-A2402. Using the COS-7 cells as a target cell, incubation was performed together with OK-CTLp. As a result, COS-7 cells, to which KM-PA-2 or KM-PA-4 was cotransfected with HLA-A0207, induced IFN-γ production from OK-CTLp, in a dose dependent manner of the gene (FIGS. 19A-19B.) The SEREX method is a method for detection of the tumor antigen. However, among 1500 or more kinds of tumor antigens detected by this method, those identified as tumor antigens capable of inducing both cell-mediated immunity and humoral immunity are only MAGE-1, tyrosinase, and NY-ESO-1. Therefore, even a gene identified by the SEREX method as encoding the tumor antigen cannot always activate CTL. It was first found that the above-described tumor antigen genes, KM-PA-2 and KM-PA-4, can activate CTL in an HLA-A2-restricted manner.

Example 8

Preparation of Tumor Antigen and Activity for Inducing CTL from PBMC of Cancer Patient In order to obtain the tumor antigen peptide derived from the tumor antigen genes, KM-PA-2 and KM-PA-4, obtained from Example 7, different peptides of 9-mer or 10-mer were designed based on the amino acid sequences encoded by KM-PA-2 and KM-PA-4 and synthesized by a well-known method, in the same way as that in Example 4.

Figure 20:
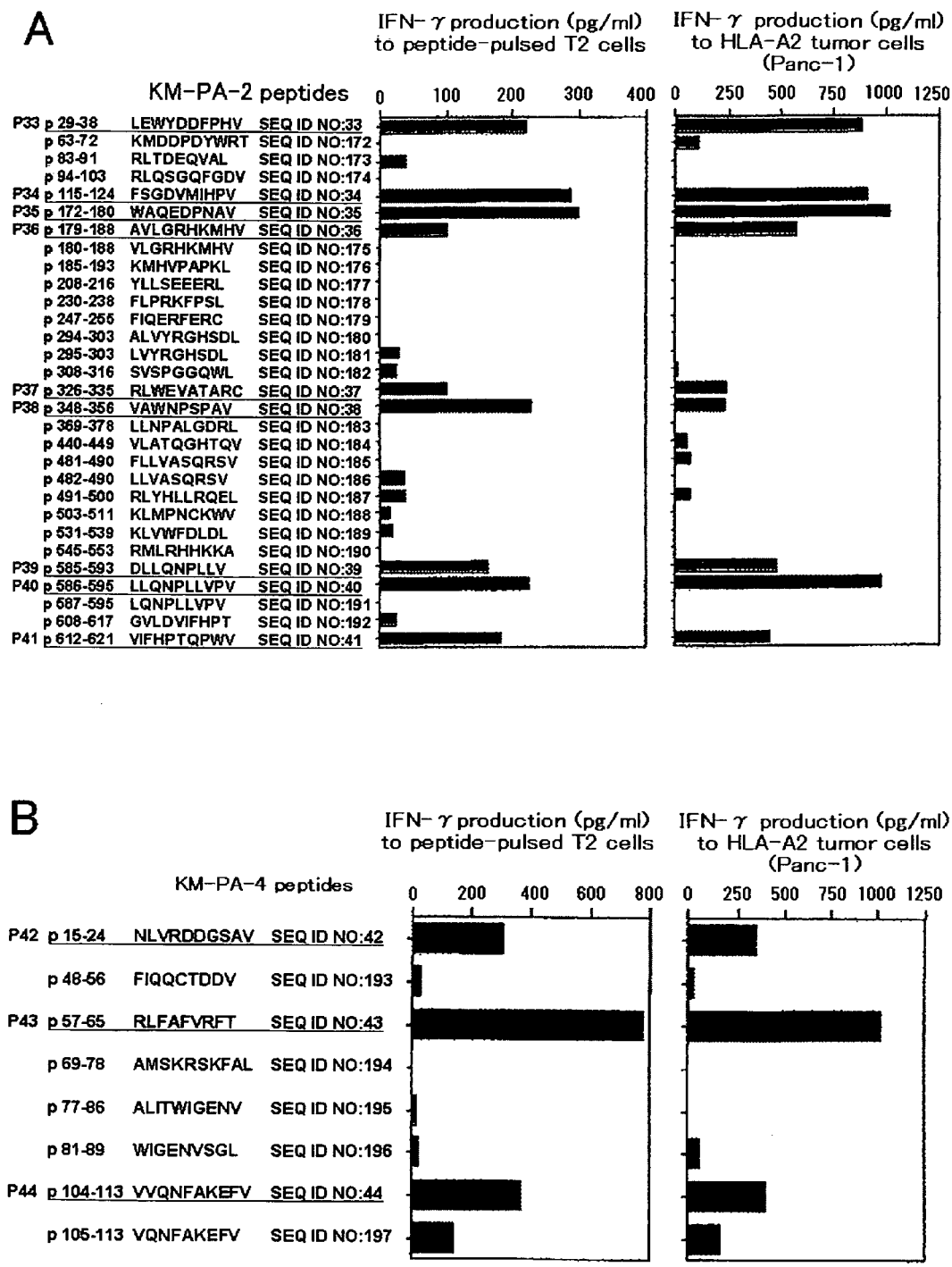
FIGS. 20A-20B show that peptides derived from the tumor antigen genes KM-PA-2 and KM-PA-4, respectively, which were obtained from the human pancreatic adenocarcinoma cell line CFPAC-1, can induce CTL from peripheral blood mononuclear cells (PBMC) of a cancer patient, which shows cytotoxicity against T2 cells which have been pulsed with the peptide corresponding to the peptide used for stimulating the PBMC (left-hand of FIGS. 20A-20B,) and an HLA-A2+ tumor cell Panc-1 (right-hand of FIGS. 20A-20B.)
Figure 21:
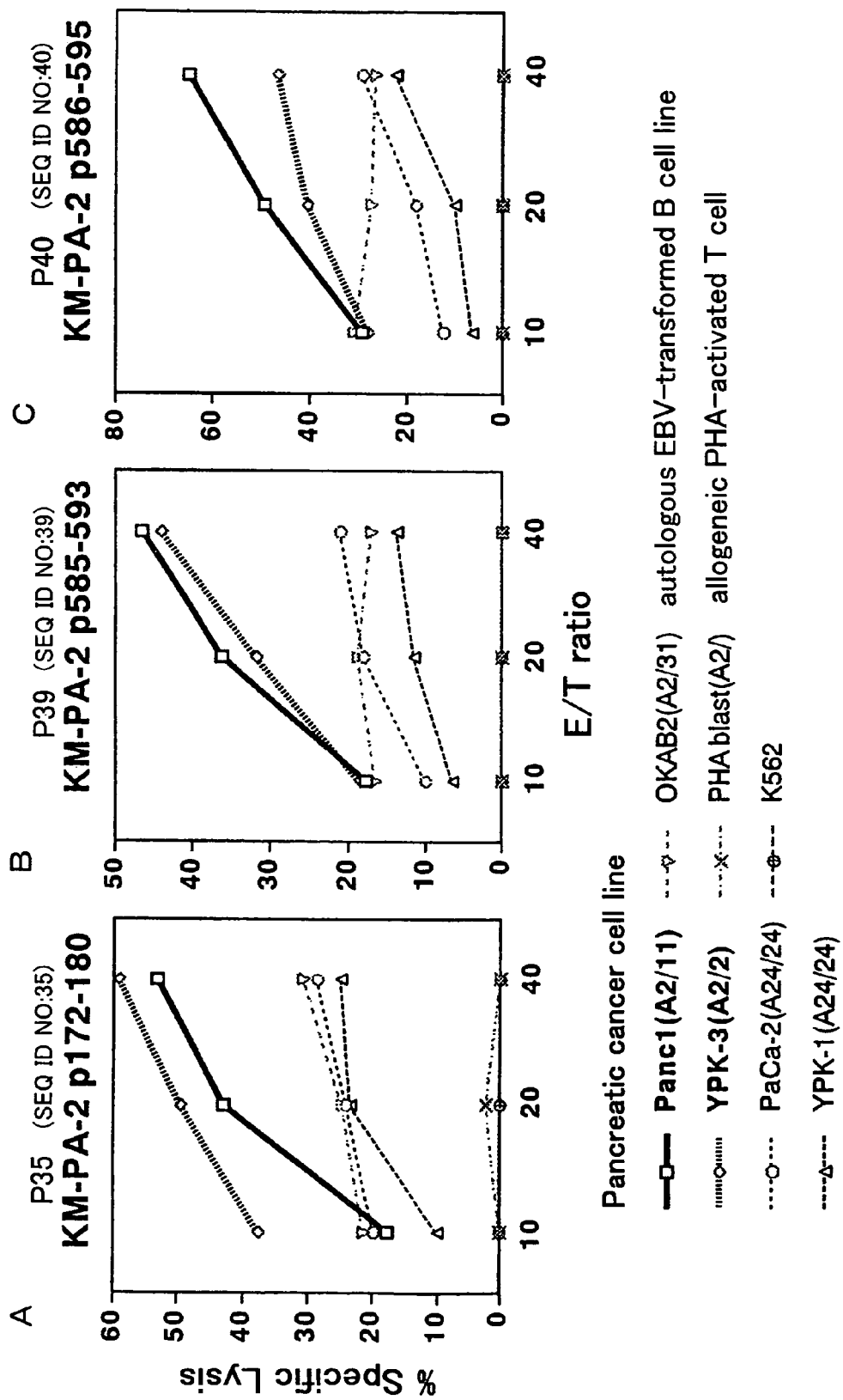
FIGS. 21A-21C show that CTL, which was induced from peripheral blood mononuclear cells of a cancer patient by peptide derived from the tumor antigen gene KM-PA-2 obtained from the human pancreatic adenocarcinoma cell line CFPAC-1, lyses tumor cells in an HLA-A2-restricted manner.

The ability of the synthesized peptide to induce CTL from the peripheral blood mononuclear cells of the colon cancer patient, from whom OK-CTLp was obtained, was examined in the same way as that in Example 6. As a result, as shown in FIGS. 20A-20B, PBMC that was stimulated in vitro using any one of peptides P33 to P41 (SEQ ID NO: 33 to SEQ ID NO:41) derived from KM-PA-2 and peptides P42 to P44 (SEQ ID NO:42 to SEQ ID NO:44) derived from KM-PA-4, produced IFN-γ through recognition of the T2 cells (left-hand figure of FIGS. 20A-20B,) which were pulsed with the peptide corresponding to that used for stimulation of the PBMC, and the Panc-1 cell (right-hand of FIGS. 20A-20B,) which is the HLA-A2$^+$ tumor cell. However, the PBMC reacted merely to the HLA-A2$^-$ tumor cell. As a result, it was revealed that any one of the above-described twelve peptides can induce the antigen specific CTL from PBMC of the cancer patient in an HLA-A2-restricted manner and that the induced CTL can recognize the above-described peptides to produce IFN-γ in an HLA-A2-restricted manner. In addition, cytotoxicity of these CTLs induced by the peptides was directly confirmed by the $^{51}$Cr-releasing test in the same way as that in Example 6. FIGS. 21A-21C show a representative example of the result. As shown in FIGS. 21A-21C, CTLs induced from PBMC of the cancer patient by P35, P39, or P40 lysed Panc-1 cells and YPK-3 cells, both of which are HLA-A2$^+$ tumor cells. However, the HLA-A2$^-$ tumor cell PaCa-2, the EBV-B cell line OKAB2, and the T cells stimulated by PHA, was not lysed. In other words, it was revealed that the above-described peptides can induce CTL showing cytotoxicity from the peripheral blood mononuclear cells of the cancer patient in an HLA-A2-restricted manner. Further, CTL was also induced by the above-described peptides from PBMC obtained from the cancer patient, such as a pancreatic cancer patient, in addition to the colon cancer patient from whom OK-CTLp was obtained.

Example 9

In order to determine the phenotype of TCR expressed on the cell surface of the CTL clone recognizing the above-described peptide, total RNA of each clone was obtained from each 5×10$^6$ CTL clones, which were obtained in Example 3, using RNAzol™B (TEL-TEST Corp.) cDNA was prepared using the SuperScript™ Preamplification System (Invitrogen Corp.) for first strand cDNA synthesis. Single stranded cDNA was amplified by polymerase chain reaction (PCR) using one of the 22 different Vβ primers (Vβ1 to 20) and 3° C. β primers. PCR was performed for 35 cycles, wherein 1 cycle comprised denaturation at 94° C. for 1 min, annealing at 58° C. for 2 min, and extension at 72° C. for 3 min. The PCR product was inserted into plasmid pCR2 followed by transformation into *Escherichia coli* using the TA cloning system (Invitrogen Corp.), selection of colonies, and plasmid preparation for determining the cDNA sequence.

As the result, two each of CTL clones reacting with the peptides derived from UBE2V and gene 1, the peptide derived from HNRPL and gene 2, and the peptide derived from 2-5 OAS3 and gene 6, expressed TCR-Vβ 8.1, TCR-Vβ 3.2, and TCR-Vβ 14, respectively. In addition, CTL clones recognizing the peptide derived from WHSC2 and gene 3, the peptide derived from EIF4EBP1 and gene 4, the peptide derived from ppMAPkkk and gene 5, expressed TCR-Vβ 13.1, TCR-Vβ 8.1, and TCR-Vβ 18, respectively (Table 8-1 and Table 8-2).

Two each of CTL clones recognizing the peptide derived from UBE2V and gene 1, the peptide derived from HNRPL and gene 2, and the peptide derived from 2-5 OAS3 and gene 6, expressed TCR possessing different complementarity-determining regions 3 (CDR3) (an element responsible for binding to the antigenic epitopes on the groove of the HLA class I molecules), respectively. CTL clones recognizing the peptide derived from WHSC2 and gene 3, the peptide derived from EIF4EBP1 and gene 4, the peptide derived from ppMAPkkk and gene 5, expressed TCR possessing different CDR3, respectively. The amino acid sequence of each CDR3 is that shown with an underline in Table 8-2.

TABLE 8-1

| CTL clone | Epitopes | Vβ | Dβ | Jβ | Cβ |
|---|---|---|---|---|---|
| 2-2-H3 | UBE2V 43-51 | 8.1 | 2.1 | 2.3 | 2 |
| 2-1-H12 | UBE2V 43-51 | 8.1 | 2.1 | 2.3 | 2 |
| 1-2-D7 | HNRPL 140-148 | 3.2 | 1.1 | 2.7 | 2 |
| 1-2-D12 | HNRPL 140-148 | 3.2 | 1.1 | 2.7 | 2 |
| 4-2-A11 | WHSC2 103-111 | 13.1 | 2.1 | 2.7 | 2 |
| 4-2-B3 | EIF4EBP1 51-59 | 8.1 | 1.1 | 1.1 | 1 |
| 0.5-1-H2 | ppMAPkkk 432-440 | 18 | 1.1 | 1.1 | 1 |
| 1-2-D1 | 2-5 OAS3 666-674 | 14 | 2.1 | 2.3 | 2 |
| 2-2-B4 | 2-5 OAS3 666-674 | 14 | 2.1 | 2.3 | 2 |

TABLE 8-2

| CTL clone | Vβ | Dβ* | Cβ |
|---|---|---|---|
| 2-2-H3 | IYFNNNVPIDDSGMPEDRFSAKMPNAS FSTLKIQPSEPRDSAVYFCAS | SLGLAGGEQFFGPGTRLTVL | EDLKNVFPPE |
| 2-1-H12 | IYFNNNVPIDDSGMPEDRFSAKMPNAS FSTLKIQPSEPRDSAVYFCAS | SLGLAGGEQFFGPGTRLTVL | EDLKNVFPPE |
| 1-2-D7 | VSREKKERFSLILESASTNQTSMYLCAS | SLDRSYEQYFGPGTRLTVT | EDLKNVFPPE |
| 1-2-D12 | VSREKKERFSLILESASTNQTSMYLCAS | SLDRSYEQYFGPGTRLTVT | EDLKNVFPPE |
| 4-2-A11 | QGEVPNGYNVSRSTTEDFPLRLLSAAP SQTSVYFCAS | SYGGGSSYEQYFGPGTRLTVT | EDLKNVFPPE |
| 4-2-B3 | IYFNNNVPIDDSGMPEDRFSAKMPNAS FSTLKIQPSEPRDSAVYFCAS | SRVSGEAFFGQGTRLTVV | EDLKNVFPPE |
| 0.5-1-H2 | DESGMPKERFSAEFPKEGPSILRIQQV VRGDSAAYFCAS | SPTELDTEAFFGQGTRLTVV | EDLKNVFPPE |
| 1-2-D1 | VSREKPNFPLILESPSPNQTSLYFCAS | GGSTDTQYFGPGTRLTVL | EDLKNVFPPE |
| 2-2-B4 | VSRKEKRNFPLILESPSPNQTSLYFCAS | GGSTDTQYFGPGTRLTVL | EDLKNVFPPE |

INDUSTRIAL APPLICABILITY

According to the present invention, HLA-A2-restricted cytotoxic T lymphocytes can be induced, which makes it possible to achieve a specific immunotherapy for pancreatic cancer, colon cancer, and stomach cancer. HLA-A2 alleles are found in 23% of African Blacks, 53% of Chinese, 40% of Japanese, 49% of Northern Caucasians, and 38% of Southern Caucasians. Consequently, the present invention can be expected its great contribution to cancer therapy. Moreover, the present invention greatly contributes to fundamental research on the molecule related to recognition by T cells of a pancreatic cancer cell, a colon cancer cell, stomach cancer, and so on.

The invention claimed is:

1. An isolated polypeptide consisting of the amino acid sequence of SEQ ID NO:49 or a peptide fragment thereof, wherein said fragment is selected from the group consisting of SEQ ID NO:16, SEQ ID NO:17, and SEQ ID NO:18.

2. A composition comprising a polypeptide consisting of the amino acid sequence of SEQ ID NO:49 or a peptide fragment thereof, wherein said fragment is selected from the group consisting of SEQ ID NO:16, SEQ ID NO:17, and SEQ ID NO:18, and a pharmaceutically acceptable carrier.

3. A method for inducing cytotoxic T lymphocytes, comprising contacting, in vitro, lymphocytes with a composition comprising peripheral blood-mononuclear cells incubated together with a peptide fragment selected from the group consisting of SEQ ID NO:16, SEQ ID NO:17 and SEQ ID NO:18, wherein the lymphocytes contain HLA-A2-restricted cytotoxic T lymphocytes.

* * * * *

SEQUENCE LISTING

```
<160> NUMBER OF SEQ ID NOS: 197

<210> SEQ ID NO 1
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 1

Arg Leu Gln Glu Trp Cys Ser Val Ile
1               5

<210> SEQ ID NO 2
<211> LENGTH: 10
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 2

Leu Leu Leu Leu Ala Arg Trp Glu Asp Thr
1               5                   10

<210> SEQ ID NO 3
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 3

Leu Ile Ala Asp Phe Leu Ser Gly Leu
1               5

<210> SEQ ID NO 4
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 4

Leu Leu Gln Asp Trp His Val Ile Leu
1               5

<210> SEQ ID NO 5
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes
```

```
<400> SEQUENCE: 5

Ile Leu Pro Arg Lys His His Arg Ile
1               5

<210> SEQ ID NO 6
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 6

Ala Leu Val Glu Phe Glu Asp Val Leu
1               5

<210> SEQ ID NO 7
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 7

Cys Leu Tyr Gly Asn Val Glu Lys Val
1               5

<210> SEQ ID NO 8
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 8

Phe Met Phe Gly Gln Lys Leu Asn Val
1               5

<210> SEQ ID NO 9
<211> LENGTH: 10
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 9

Asn Val Leu His Phe Phe Asn Ala Pro Leu
1               5                   10

<210> SEQ ID NO 10
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 10

Ala Ser Leu Asp Ser Asp Pro Trp Val
1               5

<210> SEQ ID NO 11
<211> LENGTH: 9
<212> TYPE: PRT
```

```
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 11

Ile Leu Gly Glu Leu Arg Glu Lys Val
1               5

<210> SEQ ID NO 12
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 12

Met Leu Pro Leu Glu Cys Gln Tyr Leu
1               5

<210> SEQ ID NO 13
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 13

Thr Leu Leu Arg Lys Glu Arg Gly Val
1               5

<210> SEQ ID NO 14
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 14

Arg Ile Ile Tyr Asp Arg Lys Phe Leu
1               5

<210> SEQ ID NO 15
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 15

Ile Ile Tyr Asp Arg Lys Phe Leu Met
1               5

<210> SEQ ID NO 16
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 16

Gln Ile Leu Lys Gly Leu Leu Phe Leu
1               5
```

```
<210> SEQ ID NO 17
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 17

Gly Leu Leu Phe Leu His Thr Arg Thr
1               5

<210> SEQ ID NO 18
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 18

Asp Leu Leu Ser His Ala Phe Phe Ala
1               5

<210> SEQ ID NO 19
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 19

Gln Gln Leu Cys Val Tyr Trp Thr Val
1               5

<210> SEQ ID NO 20
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 20

Ser Leu Leu Tyr Leu Asn Gln Ser Val
1               5

<210> SEQ ID NO 21
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 21

Lys Val His Pro Val Ile Trp Ser Leu
1               5

<210> SEQ ID NO 22
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes
```

```
<400> SEQUENCE: 22

Asp Met Trp Thr Val Ile Ala Pro Val
1               5

<210> SEQ ID NO 23
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 23

Gln Leu Gly Gln Gly Asn Leu Lys Val
1               5

<210> SEQ ID NO 24
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 24

Leu Leu Leu Lys Tyr Thr Glu Lys Leu
1               5

<210> SEQ ID NO 25
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 25

Thr Met Leu Pro His His Ala Gly Leu
1               5

<210> SEQ ID NO 26
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 26

Leu Leu Arg Arg Ala Asp Phe His Val
1               5

<210> SEQ ID NO 27
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 27

Glu Leu Leu Asn Arg Tyr Leu Tyr Leu
1               5

<210> SEQ ID NO 28
<211> LENGTH: 9
```

```
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 28

Leu Leu Met Leu Gln Asn Ala Leu Thr
1               5

<210> SEQ ID NO 29
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 29

Tyr Gln Leu Pro Asp Trp Arg Leu Val
1               5

<210> SEQ ID NO 30
<211> LENGTH: 10
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 30

Leu Met Leu Gln Asn Ala Leu Thr Thr Met
1               5                   10

<210> SEQ ID NO 31
<211> LENGTH: 10
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 31

Leu Leu Met Leu Gln Asn Ala Leu Thr Thr
1               5                   10

<210> SEQ ID NO 32
<211> LENGTH: 10
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 32

Thr Gln Leu Ala Thr Tyr Ser Phe Glu Val
1               5                   10

<210> SEQ ID NO 33
<211> LENGTH: 10
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 33

Leu Glu Trp Tyr Asp Asp Phe Pro His Val
```

1               5                   10

<210> SEQ ID NO 34
<211> LENGTH: 10
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 34

Phe Ser Gly Asp Val Met Ile His Pro Val
1               5                   10

<210> SEQ ID NO 35
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 35

Trp Ala Gln Glu Asp Pro Asn Ala Val
1               5

<210> SEQ ID NO 36
<211> LENGTH: 10
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 36

Ala Val Leu Gly Arg His Lys Met His Val
1               5                   10

<210> SEQ ID NO 37
<211> LENGTH: 10
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 37

Arg Leu Trp Glu Val Ala Thr Ala Arg Cys
1               5                   10

<210> SEQ ID NO 38
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 38

Val Ala Trp Asn Pro Ser Pro Ala Val
1               5

<210> SEQ ID NO 39
<211> LENGTH: 9
<212> TYPE: PRT
<213> ORGANISM: Artificial
<220> FEATURE:
<223> OTHER INFORMATION: Designed peptide having an ability to activate HLA-A2 restricted Cytotoxic T lymphocytes

<400> SEQUENCE: 39

Asp Leu Leu Gln Asn Pro Leu Leu Val
1               5

<210> SEQ ID NO 40
<211> LENGTH: 10
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 40

Leu Leu Gln Asn Pro Leu Leu Val Pro Val
1               5                   10

<210> SEQ ID NO 41
<211> LENGTH: 10
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 41

Val Ile Phe His Pro Thr Gln Pro Trp Val
1               5                   10

<210> SEQ ID NO 42
<211> LENGTH: 10
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 42

Asn Leu Val Arg Asp Asp Gly Ser Ala Val
1               5                   10

<210> SEQ ID NO 43
<211> LENGTH: 9
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 43

Arg Leu Phe Ala Phe Val Arg Phe Thr
1               5

<210> SEQ ID NO 44
<211> LENGTH: 10
<212> TYPE: PRT
<213> ORGANISM: Artificial
<220> FEATURE:
<223> OTHER INFORMATION: Designed peptide having an ability to activate
      HLA-A2 restricted Cytotoxic T lymphocytes

<400> SEQUENCE: 44

Val Val Gln Asn Phe Ala Lys Glu Phe Val
1               5                   10

<210> SEQ ID NO 45

<211> LENGTH: 270
<212> TYPE: PRT
<213> ORGANISM: Homo sapiens

<400> SEQUENCE: 45

Met Ala Gly Ala Glu Asp Trp Pro Gly Gln Gln Leu Glu Leu Asp Glu
1               5                   10                  15

Asp Glu Ala Ser Cys Cys Arg Trp Gly Ala Gln His Ala Gly Ala Arg
            20                  25                  30

Glu Leu Ala Ala Leu Tyr Ser Pro Gly Lys Arg Leu Gln Glu Trp Cys
        35                  40                  45

Ser Val Ile Leu Cys Phe Ser Leu Ile Ala His Asn Leu Val His Leu
    50                  55                  60

Leu Leu Leu Ala Arg Trp Glu Asp Thr Pro Leu Val Ile Leu Gly Val
65                  70                  75                  80

Val Ala Gly Ala Leu Ile Ala Asp Phe Leu Ser Gly Leu Val His Trp
                85                  90                  95

Gly Ala Asp Thr Trp Gly Ser Val Glu Leu Pro Ile Val Gly Lys Ala
            100                 105                 110

Phe Ile Arg Pro Phe Arg Glu His His Ile Asp Pro Thr Ala Ile Thr
        115                 120                 125

Arg His Asp Phe Ile Glu Thr Asn Gly Asp Asn Cys Leu Val Thr Leu
    130                 135                 140

Leu Pro Leu Leu Asn Met Ala Tyr Lys Phe Arg Thr His Ser Pro Glu
145                 150                 155                 160

Ala Leu Glu Gln Leu Tyr Pro Trp Glu Cys Phe Val Phe Cys Leu Ile
                165                 170                 175

Ile Phe Gly Thr Phe Thr Asn Gln Ile His Lys Trp Ser His Thr Tyr
            180                 185                 190

Phe Gly Leu Pro Arg Trp Val Thr Leu Leu Gln Asp Trp His Val Ile
        195                 200                 205

Leu Pro Arg Lys His His Arg Ile His His Val Ser Pro His Glu Thr
    210                 215                 220

Tyr Phe Cys Ile Thr Thr Gly Trp Leu Asn Tyr Pro Leu Glu Lys Ile
225                 230                 235                 240

Gly Phe Trp Arg Arg Leu Glu Asp Leu Ile Gln Gly Leu Thr Gly Glu
                245                 250                 255

Lys Pro Arg Ala Asp Asp Met Lys Trp Ala Gln Lys Ile Lys
            260                 265                 270

<210> SEQ ID NO 46
<211> LENGTH: 589
<212> TYPE: PRT
<213> ORGANISM: Homo sapiens

<400> SEQUENCE: 46

Met Ser Arg Arg Leu Leu Pro Arg Ala Glu Lys Arg Arg Arg Arg Leu
1               5                   10                  15

Glu Gln Arg Gln Gln Pro Asp Glu Gln Arg Arg Ser Gly Ala Met
            20                  25                  30

Val Lys Met Ala Ala Ala Gly Gly Gly Gly Gly Arg Tyr Tyr
        35                  40                  45

Gly Gly Gly Ser Glu Gly Gly Arg Ala Pro Lys Arg Leu Lys Thr Asp
    50                  55                  60

Asn Ala Gly Asp Gln His Gly Gly Gly Gly Gly Gly Gly Ala
65                  70                  75                  80

-continued

Gly Ala Ala Gly Gly Gly Gly Gly Glu Asn Tyr Asp Asp Pro His
                85                  90                  95

Lys Thr Pro Ala Ser Pro Val Val His Ile Arg Gly Leu Ile Asp Gly
            100                 105                 110

Val Val Glu Ala Asp Leu Val Glu Ala Leu Gln Glu Phe Gly Pro Ile
        115                 120                 125

Ser Tyr Val Val Val Met Pro Lys Lys Arg Gln Ala Leu Val Glu Phe
    130                 135                 140

Glu Asp Val Leu Gly Ala Cys Asn Ala Val Asn Tyr Ala Ala Asp Asn
145                 150                 155                 160

Gln Ile Tyr Ile Ala Gly His Pro Ala Phe Val Asn Tyr Ser Thr Ser
                165                 170                 175

Gln Lys Ile Ser Arg Pro Gly Asp Ser Asp Asp Ser Arg Ser Val Asn
            180                 185                 190

Ser Val Leu Leu Phe Thr Ile Leu Asn Pro Ile Tyr Ser Ile Thr Thr
        195                 200                 205

Asp Val Leu Tyr Thr Ile Cys Asn Pro Cys Gly Pro Val Gln Arg Ile
    210                 215                 220

Val Ile Phe Arg Lys Asn Gly Val Gln Ala Met Val Glu Phe Asp Ser
225                 230                 235                 240

Val Gln Ser Ala Gln Arg Ala Lys Ala Ser Leu Asn Gly Ala Asp Ile
                245                 250                 255

Tyr Ser Gly Cys Cys Thr Leu Lys Ile Glu Tyr Ala Lys Pro Thr Arg
            260                 265                 270

Leu Asn Val Phe Lys Asn Asp Gln Asp Thr Trp Asp Tyr Thr Asn Pro
        275                 280                 285

Asn Leu Ser Gly Gln Gly Asp Pro Gly Ser Asn Pro Asn Lys Arg Gln
    290                 295                 300

Arg Gln Pro Pro Leu Leu Gly Asp His Pro Ala Glu Tyr Gly Gly Pro
305                 310                 315                 320

His Gly Gly Tyr His Ser His Tyr His Asp Glu Gly Tyr Gly Pro Pro
                325                 330                 335

Pro Pro His Tyr Glu Gly Arg Arg Met Gly Pro Pro Val Gly Gly His
            340                 345                 350

Arg Arg Gly Pro Ser Arg Tyr Gly Pro Gln Tyr Gly His Pro Pro Pro
        355                 360                 365

Pro Pro Pro Pro Pro Glu Tyr Gly Pro His Ala Asp Ser Pro Val Leu
    370                 375                 380

Met Val Tyr Gly Leu Asp Gln Ser Lys Met Asn Gly Asp Arg Val Phe
385                 390                 395                 400

Asn Val Phe Cys Leu Tyr Gly Asn Val Glu Lys Val Lys Phe Met Lys
                405                 410                 415

Ser Lys Pro Gly Ala Ala Met Val Glu Met Ala Asp Gly Tyr Ala Val
            420                 425                 430

Asp Arg Ala Ile Thr His Leu Asn Asn Asn Phe Met Phe Gly Gln Lys
        435                 440                 445

Leu Asn Val Cys Val Ser Lys Gln Pro Ala Ile Met Pro Gly Gln Ser
    450                 455                 460

Tyr Gly Leu Glu Asp Gly Ser Cys Ser Tyr Lys Asp Phe Ser Glu Ser
465                 470                 475                 480

Arg Asn Asn Arg Phe Ser Thr Pro Glu Gln Ala Ala Lys Asn Arg Ile
                485                 490                 495

-continued

```
Gln His Pro Ser Asn Val Leu His Phe Phe Asn Ala Pro Leu Glu Val
                500                 505                 510
Thr Glu Glu Asn Phe Phe Glu Ile Cys Asp Glu Leu Gly Val Lys Arg
            515                 520                 525
Pro Ser Ser Val Lys Val Phe Ser Gly Lys Ser Glu Arg Ser Ser Ser
        530                 535                 540
Gly Leu Glu Trp Glu Ser Lys Ser Asp Ala Leu Glu Thr Leu Gly
545                 550                 555                 560
Phe Leu Asn His Tyr Gln Met Lys Asn Pro Asn Gly Pro Tyr Pro Tyr
                565                 570                 575
Thr Leu Lys Leu Cys Phe Ser Thr Ala Gln His Ala Ser
            580                 585
```

<210> SEQ ID NO 47
<211> LENGTH: 549
<212> TYPE: PRT
<213> ORGANISM: Homo sapiens

<400> SEQUENCE: 47

```
Met Ala Ser Met Arg Glu Ser Asp Thr Gly Leu Trp Leu His Asn Lys
1               5                   10                  15
Leu Gly Ala Thr Asp Glu Leu Trp Ala Pro Pro Ser Ile Ala Ser Leu
            20                  25                  30
Leu Thr Ala Ala Ile Ile Asp Asn Ile Arg Leu Cys Phe His Gly Leu
        35                  40                  45
Ser Ser Ala Ser Leu Leu Thr Ala Ala Val Ile Asp Asn Ile Arg Leu
    50                  55                  60
Cys Phe His Gly Leu Ser Ser Ala Val Lys Leu Lys Leu Leu Leu Gly
65                  70                  75                  80
Thr Leu His Leu Pro Arg Arg Thr Val Asp Glu Met Lys Gly Ala Leu
                85                  90                  95
Met Glu Ile Ile Gln Leu Ala Ser Leu Asp Ser Asp Pro Trp Val Leu
            100                 105                 110
Met Val Ala Asp Ile Leu Lys Ser Phe Pro Asp Thr Gly Ser Leu Asn
        115                 120                 125
Leu Glu Leu Glu Glu Gln Asn Pro Asn Val Gln Asp Ile Leu Gly Glu
    130                 135                 140
Leu Arg Glu Lys Val Gly Glu Cys Glu Ala Ser Ala Met Leu Pro Leu
145                 150                 155                 160
Glu Cys Gln Tyr Leu Asn Lys Asn Ala Leu Thr Thr Leu Ala Gly Pro
                165                 170                 175
Leu Thr Pro Pro Val Lys His Phe Gln Leu Lys Arg Lys Pro Lys Ser
            180                 185                 190
Ala Thr Leu Arg Ala Glu Leu Leu Gln Lys Ser Thr Glu Thr Ala Gln
        195                 200                 205
Gln Leu Lys Arg Ser Ala Gly Val Pro Phe His Ala Lys Gly Arg Gly
    210                 215                 220
Leu Leu Arg Lys Met Asp Thr Thr Pro Leu Lys Gly Ile Pro Lys
225                 230                 235                 240
Gln Ala Pro Phe Arg Ser Pro Thr Ala Pro Ser Val Phe Ser Pro Thr
                245                 250                 255
Gly Asn Arg Thr Pro Ile Pro Pro Ser Arg Thr Leu Leu Arg Lys Glu
            260                 265                 270
Arg Gly Val Lys Leu Leu Asp Ile Ser Glu Leu Asp Met Val Gly Ala
        275                 280                 285
```

```
Gly Arg Glu Ala Lys Arg Arg Lys Thr Leu Asp Ala Glu Val Val
    290                 295                 300

Glu Lys Pro Ala Lys Glu Glu Thr Val Val Glu Asn Ala Thr Pro Asp
305                 310                 315                 320

Tyr Ala Ala Gly Leu Val Ser Thr Gln Lys Leu Gly Ser Leu Asn Asn
                325                 330                 335

Glu Pro Ala Leu Pro Ser Thr Ser Tyr Leu Pro Ser Thr Pro Ser Val
            340                 345                 350

Val Pro Ala Ser Ser Tyr Ile Pro Ser Ser Glu Thr Pro Ala Pro
        355                 360                 365

Ser Ser Arg Glu Ala Ser Arg Pro Glu Glu Pro Ser Ala Pro Ser
    370                 375                 380

Pro Thr Leu Pro Ala Gln Phe Lys Gln Arg Ala Pro Met Tyr Asn Ser
385                 390                 395                 400

Gly Leu Ser Pro Ala Thr Pro Thr Pro Ala Ala Pro Thr Ser Pro Leu
                405                 410                 415

Thr Pro Thr Thr Pro Pro Ala Val Ala Pro Thr Thr Gln Thr Pro Pro
            420                 425                 430

Val Ala Met Val Ala Pro Gln Thr Gln Ala Pro Ala Gln Gln Gln Pro
        435                 440                 445

Lys Lys Asn Leu Ser Leu Thr Arg Glu Gln Met Phe Ala Ala Gln Glu
    450                 455                 460

Met Phe Lys Thr Ala Asn Lys Val Thr Arg Pro Glu Lys Ala Leu Ile
465                 470                 475                 480

Leu Gly Phe Met Ala Gly Ser Arg Glu Asn Pro Cys Gln Glu Gln Gly
                485                 490                 495

Asp Val Ile Gln Ile Lys Leu Ser Glu His Thr Glu Asp Leu Pro Lys
            500                 505                 510

Ala Asp Gly Gln Gly Ser Thr Thr Met Leu Val Asp Thr Val Phe Glu
        515                 520                 525

Met Asn Tyr Ala Thr Gly Gln Trp Thr Arg Phe Lys Lys Tyr Lys Pro
    530                 535                 540

Met Thr Asn Val Ser
545

<210> SEQ ID NO 48
<211> LENGTH: 118
<212> TYPE: PRT
<213> ORGANISM: Homo sapiens

<400> SEQUENCE: 48

Met Ser Gly Gly Ser Ser Cys Ser Gln Thr Pro Ser Arg Ala Ile Pro
1               5                   10                  15

Ala Thr Arg Arg Val Val Leu Gly Asp Gly Val Gln Leu Pro Pro Gly
                20                  25                  30

Asp Tyr Ser Thr Thr Pro Gly Gly Thr Leu Phe Ser Thr Thr Pro Gly
            35                  40                  45

Gly Thr Arg Ile Ile Tyr Asp Arg Lys Phe Leu Met Glu Cys Arg Asn
        50                  55                  60

Ser Pro Val Thr Lys Thr Pro Arg Asp Leu Pro Thr Ile Pro Gly
65                  70                  75                  80

Val Thr Ser Pro Ser Ser Asp Glu Pro Pro Met Glu Ala Ser Gln Ser
                85                  90                  95

His Leu Arg Asn Ser Pro Glu Asp Lys Arg Ala Gly Gly Glu Glu Ser
```

```
                100                 105                 110

Gln Phe Glu Met Asp Ile
        115

<210> SEQ ID NO 49
<211> LENGTH: 779
<212> TYPE: PRT
<213> ORGANISM: Homo sapiens

<400> SEQUENCE: 49

Met Glu Pro Gly Arg Gly Ala Gly Pro Ala Gly Met Ala Glu Pro Arg
1               5                   10                  15

Ala Lys Ala Ala Arg Pro Gly Pro Gln Arg Phe Leu Arg Arg Ser Val
            20                  25                  30

Val Glu Ser Asp Gln Glu Glu Pro Gly Leu Glu Ala Ala Glu Ala
        35                  40                  45

Pro Gly Pro Gln Pro Pro Gln Pro Leu Gln Arg Arg Val Leu Leu Leu
    50                  55                  60

Cys Lys Thr Arg Arg Leu Ile Ala Glu Arg Ala Arg Gly Arg Pro Ala
65                  70                  75                  80

Ala Pro Ala Pro Ala Ala Leu Val Ala Gln Pro Gly Ala Pro Gly Ala
                85                  90                  95

Pro Ala Asp Ala Gly Pro Glu Pro Val Gly Thr Gln Glu Pro Gly Pro
            100                 105                 110

Asp Pro Ile Ala Ala Ala Val Glu Thr Ala Pro Ala Pro Asp Gly Gly
        115                 120                 125

Pro Arg Glu Glu Ala Ala Thr Val Arg Lys Glu Asp Glu Gly Ala
    130                 135                 140

Ala Glu Ala Lys Pro Glu Pro Gly Arg Thr Arg Arg Asp Glu Pro Glu
145                 150                 155                 160

Glu Glu Glu Asp Asp Glu Asp Asp Leu Lys Ala Val Ala Thr Ser Leu
                165                 170                 175

Asp Gly Arg Phe Leu Lys Phe Asp Ile Glu Leu Gly Arg Gly Ser Phe
            180                 185                 190

Lys Thr Val Tyr Lys Gly Leu Asp Thr Glu Thr Trp Val Glu Val Ala
        195                 200                 205

Trp Cys Glu Leu Gln Asp Arg Lys Leu Thr Lys Leu Glu Arg Gln Arg
    210                 215                 220

Phe Lys Glu Glu Ala Glu Met Leu Lys Gly Leu Gln His Pro Asn Ile
225                 230                 235                 240

Val Arg Phe Tyr Asp Phe Trp Glu Ser Ser Ala Lys Gly Lys Arg Cys
                245                 250                 255

Ile Val Leu Val Thr Glu Leu Met Thr Ser Gly Thr Leu Lys Thr Tyr
            260                 265                 270

Leu Lys Arg Phe Lys Val Met Lys Pro Lys Val Leu Arg Ser Trp Cys
        275                 280                 285

Arg Gln Ile Leu Lys Gly Leu Leu Phe Leu His Thr Arg Thr Pro Pro
    290                 295                 300

Ile Ile His Arg Asp Leu Lys Cys Asp Asn Ile Phe Ile Thr Gly Pro
305                 310                 315                 320

Thr Gly Ser Val Lys Ile Gly Asp Leu Gly Leu Ala Thr Leu Lys Arg
                325                 330                 335

Ala Ser Phe Ala Lys Ser Val Ile Gly Thr Pro Glu Phe Met Ala Pro
            340                 345                 350
```

-continued

```
Glu Met Tyr Glu Glu His Tyr Asp Glu Ser Val Asp Val Tyr Ala Phe
        355                 360                 365
Gly Met Cys Met Leu Glu Met Ala Thr Ser Glu Tyr Pro Tyr Ser Glu
    370                 375                 380
Cys Gln Asn Ala Ala Gln Ile Tyr Arg Lys Val Thr Cys Gly Ile Lys
385                 390                 395                 400
Pro Ala Ser Phe Glu Lys Val His Asp Pro Glu Ile Lys Glu Ile Ile
                405                 410                 415
Gly Glu Cys Ile Cys Lys Asn Lys Glu Glu Arg Tyr Glu Ile Lys Asp
                420                 425                 430
Leu Leu Ser His Ala Phe Phe Ala Glu Asp Thr Gly Val Arg Val Glu
        435                 440                 445
Leu Ala Glu Glu Asp His Gly Arg Lys Ser Thr Ile Ala Leu Arg Leu
    450                 455                 460
Trp Val Glu Asp Pro Lys Lys Leu Lys Gly Lys Pro Lys Asp Asn Gly
465                 470                 475                 480
Ala Ile Glu Phe Thr Phe Asp Leu Glu Lys Glu Thr Pro Asp Glu Val
                485                 490                 495
Ala Gln Glu Met Ile Glu Ser Gly Phe Phe His Glu Ser Asp Val Lys
                500                 505                 510
Ile Val Ala Lys Ser Ile Arg Asp Arg Val Ala Leu Ile Gln Trp Arg
        515                 520                 525
Arg Glu Arg Ile Trp Pro Ala Leu Gln Pro Lys Glu Gln Gln Asp Val
    530                 535                 540
Gly Ser Pro Asp Lys Ala Arg Gly Pro Pro Val Pro Leu Gln Val Gln
545                 550                 555                 560
Val Thr Tyr His Ala Gln Ala Gly Gln Pro Gly Pro Glu Pro Glu
                565                 570                 575
Glu Pro Glu Ala Asp Gln His Leu Leu Pro Thr Leu Pro Thr Ser
            580                 585                 590
Ala Thr Ser Leu Ala Ser Asp Ser Thr Phe Asp Ser Gly Gln Gly Ser
        595                 600                 605
Thr Val Tyr Ser Asp Ser Gln Ser Ser Gln Gln Ser Val Met Leu Gly
    610                 615                 620
Ser Leu Ala Asp Ala Ala Pro Ser Pro Ala Gln Cys Val Cys Ser Pro
625                 630                 635                 640
Pro Val Ser Glu Gly Pro Val Leu Pro Gln Ser Leu Pro Ser Leu Gly
                645                 650                 655
Ala Tyr Gln Gln Pro Thr Ala Ala Pro Pro Leu Ala Gln Pro Thr
                660                 665                 670
Pro Leu Pro Gln Val Leu Ala Pro Gln Pro Val Val Pro Leu Gln Pro
        675                 680                 685
Val Pro Pro His Leu Pro Pro Tyr Leu Ala Pro Ala Ser Gln Val Gly
    690                 695                 700
Ala Pro Ala Gln Leu Lys Pro Leu Gln Met Pro Gln Ala Pro Leu Gln
705                 710                 715                 720
Pro Leu Ala Gln Val Pro Gln Met Pro Ile Pro Val Val Pro
                725                 730                 735
Pro Ile Thr Pro Leu Ala Gly Ile Asp Gly Leu Pro Pro Ala Leu Pro
            740                 745                 750
Asp Leu Pro Thr Ala Thr Val Pro Val Pro Pro Gln Tyr Phe
        755                 760                 765
Ser Pro Ala Val Ile Leu Pro Ser Arg Thr Arg
```

```
<210> SEQ ID NO 50
<211> LENGTH: 1087
<212> TYPE: PRT
<213> ORGANISM: Homo sapiens

<400> SEQUENCE: 50

Met Asp Leu Tyr Ser Thr Pro Ala Ala Ala Leu Asp Arg Phe Val Ala
 1               5                  10                  15

Arg Lys Leu Gln Pro Arg Lys Glu Phe Val Glu Lys Ala Arg Arg Ala
                20                  25                  30

Leu Gly Ala Leu Ala Ala Leu Arg Glu Arg Gly Gly Arg Leu Gly
            35                  40                  45

Ala Ala Pro Arg Val Leu Lys Thr Val Lys Gly Gly Ser Ser Gly
 50                  55                  60

Arg Gly Thr Ala Leu Lys Gly Gly Cys Asp Ser Glu Leu Val Ile Phe
65                  70                  75                  80

Leu Asp Cys Phe Lys Ser Tyr Val Asp Gln Arg Ala Arg Arg Ala Glu
                85                  90                  95

Ile Leu Ser Glu Met Arg Ala Ser Leu Glu Ser Trp Trp Gln Asn Pro
            100                 105                 110

Val Pro Gly Leu Arg Leu Thr Phe Pro Glu Gln Ser Val Pro Gly Ala
        115                 120                 125

Leu Gln Phe Arg Leu Thr Ser Val Asp Leu Glu Asp Trp Met Asp Val
    130                 135                 140

Ser Leu Val Pro Ala Phe Asn Val Leu Gly Gln Ala Gly Ser Gly Val
145                 150                 155                 160

Lys Pro Lys Pro Gln Val Tyr Ser Thr Leu Asn Ser Gly Cys Gln
                165                 170                 175

Gly Gly Glu His Ala Ala Cys Phe Thr Glu Leu Arg Arg Asn Phe Val
            180                 185                 190

Asn Ile Arg Pro Ala Lys Leu Lys Asn Leu Ile Leu Val Lys His
        195                 200                 205

Trp Tyr His Gln Val Cys Leu Gln Gly Leu Trp Lys Glu Thr Leu Pro
    210                 215                 220

Pro Val Tyr Ala Leu Glu Leu Leu Thr Ile Phe Ala Trp Glu Gln Gly
225                 230                 235                 240

Cys Lys Lys Asp Ala Phe Ser Leu Ala Glu Gly Leu Arg Thr Val Leu
                245                 250                 255

Gly Leu Ile Gln Gln His Gln His Leu Cys Val Phe Trp Thr Val Asn
            260                 265                 270

Tyr Gly Phe Glu Asp Pro Ala Val Gly Gln Phe Leu Gln Arg Gln Leu
        275                 280                 285

Lys Arg Pro Arg Pro Val Ile Leu Asp Pro Ala Asp Pro Thr Trp Asp
    290                 295                 300

Leu Gly Asn Gly Ala Ala Trp His Trp Asp Leu Leu Ala Gln Glu Ala
305                 310                 315                 320

Ala Ser Cys Tyr Asp His Pro Cys Phe Leu Arg Gly Met Gly Asp Pro
                325                 330                 335

Val Gln Ser Trp Lys Gly Pro Gly Leu Pro Arg Ala Gly Cys Ser Gly
            340                 345                 350

Leu Gly His Pro Ile Gln Leu Asp Pro Asn Gln Lys Thr Pro Glu Asn
        355                 360                 365
```

```
Ser Lys Ser Leu Asn Ala Val Tyr Pro Arg Ala Gly Ser Lys Pro Pro
    370                 375                 380

Ser Cys Pro Ala Pro Gly Pro Thr Gly Ala Ala Ser Ile Val Pro Ser
385                 390                 395                 400

Val Pro Gly Met Ala Leu Asp Leu Ser Gln Ile Pro Thr Lys Glu Leu
                405                 410                 415

Asp Arg Phe Ile Gln Asp His Leu Lys Pro Ser Pro Gln Phe Gln Glu
            420                 425                 430

Gln Val Lys Lys Ala Ile Asp Ile Ile Leu Arg Cys Leu His Glu Asn
        435                 440                 445

Cys Val His Lys Ala Ser Arg Val Ser Lys Gly Gly Ser Phe Gly Arg
450                 455                 460

Gly Thr Asp Leu Arg Asp Gly Cys Asp Val Glu Leu Ile Ile Phe Leu
465                 470                 475                 480

Asn Cys Phe Thr Asp Tyr Lys Asp Gln Gly Pro Arg Arg Ala Glu Ile
                485                 490                 495

Leu Asp Glu Met Arg Ala His Val Glu Ser Trp Trp Gln Asp Gln Val
            500                 505                 510

Pro Ser Leu Ser Leu Gln Phe Pro Glu Gln Asn Val Pro Glu Ala Leu
        515                 520                 525

Gln Phe Gln Leu Val Ser Thr Ala Leu Lys Ser Trp Thr Asp Val Ser
530                 535                 540

Leu Leu Pro Ala Phe Asp Ala Val Gly Gln Leu Ser Ser Gly Thr Lys
545                 550                 555                 560

Pro Asn Pro Gln Val Tyr Ser Arg Leu Leu Thr Ser Gly Cys Gln Glu
                565                 570                 575

Gly Glu His Lys Ala Cys Phe Ala Glu Leu Arg Arg Asn Phe Met Asn
            580                 585                 590

Ile Arg Pro Val Lys Leu Lys Asn Leu Ile Leu Leu Val Lys His Trp
        595                 600                 605

Tyr Arg Gln Val Ala Ala Gln Asn Lys Gly Lys Gly Pro Ala Pro Ala
610                 615                 620

Ser Leu Pro Pro Ala Tyr Ala Leu Glu Leu Leu Thr Ile Phe Ala Trp
625                 630                 635                 640

Glu Gln Gly Cys Arg Gln Asp Cys Phe Asn Met Ala Gln Gly Phe Arg
                645                 650                 655

Thr Val Leu Gly Leu Val Gln Gln His Gln Gln Leu Cys Val Tyr Trp
            660                 665                 670

Thr Val Asn Tyr Ser Thr Glu Asp Pro Ala Met Arg Met His Leu Leu
        675                 680                 685

Gly Gln Leu Arg Lys Pro Arg Pro Leu Val Leu Asp Pro Ala Asp Pro
690                 695                 700

Thr Trp Asn Val Gly His Gly Ser Trp Glu Leu Leu Ala Gln Glu Ala
705                 710                 715                 720

Ala Ala Leu Gly Met Gln Ala Cys Phe Leu Ser Arg Asp Gly Thr Ser
                725                 730                 735

Val Gln Pro Trp Asp Val Met Pro Ala Leu Leu Tyr Gln Thr Pro Ala
            740                 745                 750

Gly Asp Leu Asp Lys Phe Ile Ser Glu Phe Leu Gln Pro Asn Arg Gln
        755                 760                 765

Phe Leu Ala Gln Val Asn Lys Ala Val Asp Thr Ile Cys Ser Phe Leu
770                 775                 780

Lys Glu Asn Cys Phe Arg Asn Ser Pro Ile Lys Val Ile Lys Val Val
```

```
                785                 790                 795                 800
Lys Gly Gly Ser Ser Ala Lys Gly Thr Ala Leu Arg Gly Arg Ser Asp
                805                 810                 815

Ala Asp Leu Val Val Phe Leu Ser Cys Phe Ser Gln Phe Thr Glu Gln
                820                 825                 830

Gly Asn Lys Arg Ala Glu Ile Ile Ser Glu Ile Arg Ala Gln Leu Glu
                835                 840                 845

Ala Cys Gln Gln Glu Arg Gln Phe Glu Val Lys Phe Glu Val Ser Lys
        850                 855                 860

Trp Glu Asn Pro Arg Val Leu Ser Phe Ser Leu Thr Ser Gln Thr Met
865                 870                 875                 880

Leu Asp Gln Ser Val Asp Phe Asp Val Leu Pro Ala Phe Asp Ala Leu
                885                 890                 895

Gly Gln Leu Val Ser Gly Ser Arg Pro Ser Ser Gln Val Tyr Val Asp
            900                 905                 910

Leu Ile His Ser Tyr Ser Asn Ala Gly Glu Tyr Ser Thr Cys Phe Thr
            915                 920                 925

Glu Leu Gln Arg Asp Phe Ile Ile Ser Arg Pro Thr Lys Leu Lys Ser
        930                 935                 940

Leu Ile Arg Leu Val Lys His Trp Tyr Gln Gln Cys Thr Lys Ile Ser
945                 950                 955                 960

Lys Gly Arg Gly Ser Leu Pro Pro Gln His Gly Leu Glu Leu Leu Thr
                965                 970                 975

Val Tyr Ala Trp Glu Gln Gly Lys Asp Ser Gln Phe Asn Met Ala
            980                 985                 990

Glu Gly Phe Arg Thr Val Leu Glu  Leu Val Thr Gln Tyr  Arg Gln Leu
            995                 1000                1005

Cys Ile  Tyr Trp Thr Ile Asn  Tyr Asn Ala Lys Asp  Lys Thr Val
    1010                1015                1020

Gly Asp  Phe Leu Lys Gln Gln  Leu Gln Lys Pro Arg  Pro Ile Ile
    1025                1030                1035

Leu Asp  Pro Ala Asp Pro Thr  Gly Asn Leu Gly His  Asn Ala Arg
    1040                1045                1050

Trp Asp  Leu Leu Ala Lys Glu  Ala Ala Ala Cys Thr  Ser Ala Leu
    1055                1060                1065

Cys Cys  Met Gly Arg Asn Gly  Ile Pro Ile Gln Pro  Trp Pro Val
    1070                1075                1080

Lys Ala  Ala Val
    1085

<210> SEQ ID NO 51
<211> LENGTH: 216
<212> TYPE: PRT
<213> ORGANISM: Homo sapiens

<400> SEQUENCE: 51

Met Lys Ser Ile Ser Leu Leu Arg Tyr Gln Glu Glu Ser Lys Thr Leu
1               5                   10                  15

Ser Leu Val Ser Arg Asp Ala Lys Pro Leu Glu Val Tyr Ser Val Asp
                20                  25                  30

Phe Met Val Asp Asn Ala Gln Leu Gly Phe Leu Val Ser Asp Arg Asp
            35                  40                  45

Arg Asn Leu Met Val Tyr Met Tyr Leu Pro Glu Ala Lys Glu Ser Phe
        50                  55                  60
```

```
Gly Gly Met Arg Leu Leu Arg Arg Ala Asp Phe His Val Gly Ala His
 65                  70                  75                  80

Val Asn Thr Phe Trp Arg Thr Pro Cys Arg Gly Ala Thr Glu Gly Leu
                 85                  90                  95

Ser Lys Lys Ser Val Val Trp Glu Asn Lys His Ile Thr Trp Phe Ala
            100                 105                 110

Thr Leu Asp Gly Gly Ile Gly Leu Leu Pro Met Gln Glu Lys Thr
        115                 120                 125

Tyr Arg Arg Leu Leu Met Leu Gln Asn Ala Leu Thr Thr Met Leu Pro
    130                 135                 140

His His Ala Gly Leu Asn Pro Arg Ala Phe Arg Met Leu His Val Asp
145                 150                 155                 160

Arg Arg Thr Leu Gln Asn Ala Val Arg Asn Val Leu Asp Gly Glu Leu
                165                 170                 175

Leu Asn Arg Tyr Leu Tyr Leu Ser Thr Met Glu Arg Ser Glu Leu Ala
            180                 185                 190

Lys Lys Ile Gly Thr Thr Pro Asp Ile Ile Leu Asp Asp Leu Leu Glu
        195                 200                 205

Thr Asp Arg Val Thr Ala His Phe
    210                 215

<210> SEQ ID NO 52
<211> LENGTH: 634
<212> TYPE: PRT
<213> ORGANISM: Homo sapiens

<400> SEQUENCE: 52

Met Ala Ser Ala Arg Ile Gly Asp Glu Tyr Ala Glu Asp Ser Ser Asp
1               5                   10                  15

Glu Glu Asp Ile Arg Asn Thr Val Gly Asn Val Pro Leu Glu Trp Tyr
                20                  25                  30

Asp Asp Phe Pro His Val Gly Tyr Asp Leu Asp Gly Arg Arg Ile Tyr
            35                  40                  45

Lys Pro Leu Arg Thr Arg Asp Glu Leu Asp Gln Phe Leu Asp Lys Met
        50                  55                  60

Asp Asp Pro Asp Tyr Trp Arg Thr Val Gln Asp Pro Met Thr Gly Arg
 65                 70                  75                  80

Asp Leu Arg Leu Thr Asp Glu Gln Val Ala Leu Val Arg Arg Leu Gln
                85                  90                  95

Ser Gly Gln Phe Gly Asp Val Gly Phe Asn Pro Tyr Glu Pro Ala Val
            100                 105                 110

Asp Phe Phe Ser Gly Asp Val Met Ile His Pro Val Thr Asn Arg Pro
        115                 120                 125

Ala Asp Lys Arg Ser Phe Ile Pro Ser Leu Val Glu Lys Glu Lys Val
    130                 135                 140

Ser Arg Met Val His Ala Ile Lys Met Gly Trp Ile Gln Pro Arg Arg
145                 150                 155                 160

Pro Arg Asp Pro Thr Pro Ser Phe Tyr Asp Leu Trp Ala Gln Glu Asp
                165                 170                 175

Pro Asn Ala Val Leu Gly Arg His Lys Met His Val Pro Ala Pro Lys
            180                 185                 190

Leu Ala Leu Pro Gly His Ala Glu Ser Tyr Asn Pro Pro Glu Tyr
        195                 200                 205

Leu Leu Ser Glu Glu Glu Arg Leu Ala Trp Glu Gln Gln Glu Pro Gly
    210                 215                 220
```

-continued

```
Glu Arg Lys Leu Ser Phe Leu Pro Arg Lys Phe Pro Ser Leu Arg Ala
225                 230                 235                 240

Val Pro Ala Tyr Gly Arg Phe Ile Gln Glu Arg Phe Glu Arg Cys Leu
                245                 250                 255

Asp Leu Tyr Leu Cys Pro Arg Gln Arg Lys Met Arg Val Asn Val Asp
            260                 265                 270

Pro Glu Asp Leu Ile Pro Lys Leu Pro Arg Pro Arg Asp Leu Gln Pro
        275                 280                 285

Phe Pro Thr Cys Gln Ala Leu Val Tyr Arg Gly His Ser Asp Leu Val
    290                 295                 300

Arg Cys Leu Ser Val Ser Pro Gly Gly Gln Trp Leu Val Ser Gly Ser
305                 310                 315                 320

Asp Asp Gly Ser Leu Arg Leu Trp Glu Val Ala Thr Ala Arg Cys Val
                325                 330                 335

Arg Thr Val Pro Val Gly Gly Val Val Lys Ser Val Ala Trp Asn Pro
                340                 345                 350

Ser Pro Ala Val Cys Leu Val Ala Ala Val Glu Asp Ser Val Leu
                355                 360                 365

Leu Leu Asn Pro Ala Leu Gly Asp Arg Leu Val Ala Gly Ser Thr Asp
370                 375                 380

Gln Leu Leu Ser Ala Phe Val Pro Pro Glu Pro Pro Leu Gln Pro
385                 390                 395                 400

Ala Arg Trp Leu Glu Ala Ser Glu Glu Glu Arg Gln Val Gly Leu Arg
                405                 410                 415

Leu Arg Ile Cys His Gly Lys Pro Val Thr Gln Val Thr Trp His Gly
                420                 425                 430

Arg Gly Asp Tyr Leu Ala Val Val Leu Ala Thr Gln Gly His Thr Gln
                435                 440                 445

Val Leu Ile His Gln Leu Ser Arg Arg Ser Gln Ser Pro Phe Arg
450                 455                 460

Arg Ser His Gly Gln Val Gln Arg Val Ala Phe His Pro Ala Arg Pro
465                 470                 475                 480

Phe Leu Leu Val Ala Ser Gln Arg Ser Val Arg Leu Tyr His Leu Leu
                485                 490                 495

Arg Gln Glu Leu Thr Lys Lys Leu Met Pro Asn Cys Lys Trp Val Ser
                500                 505                 510

Ser Leu Ala Val His Pro Ala Gly Asp Asn Val Ile Cys Gly Ser Tyr
            515                 520                 525

Asp Ser Lys Leu Val Trp Phe Asp Leu Asp Leu Ser Thr Lys Pro Tyr
        530                 535                 540

Arg Met Leu Arg His His Lys Lys Ala Leu Arg Ala Val Ala Phe His
545                 550                 555                 560

Pro Arg Tyr Pro Leu Phe Ala Ser Gly Ser Asp Asp Gly Ser Val Ile
                565                 570                 575

Val Cys His Gly Met Val Tyr Asn Asp Leu Leu Gln Asn Pro Leu Leu
            580                 585                 590

Val Pro Val Lys Val Leu Lys Gly His Val Leu Thr Arg Asp Leu Gly
            595                 600                 605

Val Leu Asp Val Ile Phe His Pro Thr Gln Pro Trp Val Phe Ser Ser
610                 615                 620

Gly Ala Asp Gly Thr Val Arg Leu Phe Thr
625                 630
```

<210> SEQ ID NO 53
<211> LENGTH: 142
<212> TYPE: PRT
<213> ORGANISM: Homo sapiens

<400> SEQUENCE: 53

```
Met Ala Thr Lys Ile Asp Lys Glu Ala Cys Arg Ala Ala Tyr Asn Leu
1               5                   10                  15

Val Arg Asp Asp Gly Ser Ala Val Ile Trp Val Thr Phe Lys Tyr Asp
            20                  25                  30

Gly Ser Thr Ile Val Pro Gly Glu Gln Gly Ala Glu Tyr Gln His Phe
        35                  40                  45

Ile Gln Gln Cys Thr Asp Asp Val Arg Leu Phe Ala Phe Val Arg Phe
    50                  55                  60

Thr Thr Gly Asp Ala Met Ser Lys Arg Ser Lys Phe Ala Leu Ile Thr
65                  70                  75                  80

Trp Ile Gly Glu Asn Val Ser Gly Leu Gln Arg Ala Lys Thr Gly Thr
                85                  90                  95

Asp Lys Thr Leu Val Lys Glu Val Val Gln Asn Phe Ala Lys Glu Phe
            100                 105                 110

Val Ile Ser Asp Arg Lys Glu Leu Glu Glu Asp Phe Ile Lys Ser Glu
        115                 120                 125

Leu Lys Lys Ala Gly Gly Ala Asn Tyr Asp Ala Gln Thr Glu
    130                 135                 140
```

<210> SEQ ID NO 54
<211> LENGTH: 1775
<212> TYPE: DNA
<213> ORGANISM: Homo sapiens
<220> FEATURE:
<221> NAME/KEY: polyA_site
<222> LOCATION: (1775)..(1775)
<223> OTHER INFORMATION:

<400> SEQUENCE: 54

| | | | | | |
|---|---|---|---|---|---|
| atctcgccgc | ggttccgcgg | ccctgccgcc | gccgccnttt | ngcagagcgc | accgggccga | 60 |
| tcgggcgagt | ggccatggcg | ggcgccgagg | actggccggg | ccagcagctg | gagctggacg | 120 |
| aggacgagga | gtcttgttgc | cgctggggcg | cgcagcacgc | cggggcccgc | gagctggctg | 180 |
| cgctctactc | gccaggcaag | cgcctccagg | agtggtgctc | tgtgatcctg | tgcttcagcc | 240 |
| tcatcgccca | caacctggtc | catctcctgc | tgctggcccg | ctgggaggac | acacccctcg | 300 |
| tcatactcgg | tgttgttgca | ggggctctca | ttgctgactt | cttgtctggc | ctggtacact | 360 |
| ggggtgctga | cacatggggc | tctgtggagc | tgcccattgt | ggggaaggct | ttcatccgac | 420 |
| ccttccggga | gcaccacatt | gacccgacag | ctatcacacg | gcacgacttc | atcgagacca | 480 |
| acggggacaa | ctgcctggtg | acactgctgc | cgctgctaaa | catggcctac | aagttccgca | 540 |
| cccacagccc | tgaagccctg | gagcagctat | acccctggga | gtgcttcgtc | ttctgcctga | 600 |
| tcatcttcgg | caccttcacc | aaccagatcc | acaagtggtc | gcacacgtac | tttgggctgc | 660 |
| cacgctgggt | cacccttctg | caggactggc | atgtcatcct | gccacgtaaa | caccatcgca | 720 |
| tccaccacgt | ctcaccccac | gagacctact | tctgcatcac | cacaggctgg | ctcaactacc | 780 |
| ctctggagaa | gataggcttc | tggcgacgcc | tggaggacct | catccagggc | ctgacgggcg | 840 |
| agaagcctcg | ggcagatgac | atgaaatggg | cccagaagat | caaataactt | ctccgagcct | 900 |
| gctacctggt | tgccaacctt | ccctagcccc | caaaccgaag | ccatctgcca | aattccagcc | 960 |

-continued

| | |
|---|---|
| tctttgagct ggcccctcca gatggagagg acatctcctg ggctgggccc aggtacccca | 1020 |
| gcccacccct catgacacag aatacttgag ccactgattt ttcatttctt tttttttttt | 1080 |
| tcctcggccc ctcctcagcc acctgagttg ctctatctgc aagcctgact ctgccagcct | 1140 |
| cccctggtag agaggaggtt tacccactcc ctgcacgcct gccgtccctg ccccgctggg | 1200 |
| caagcccttc agtgtggctg gcgttggggc cagtgagttg cctctttccc tccttgtctg | 1260 |
| gccccagtgg tctggggagc ccccaggcac acctaagcgt cgtggagcat tgttctgcca | 1320 |
| cagccctgca tactgacccc gggaggctgg gcaggtggac agccccagcc accaccttca | 1380 |
| gcctagcctg tcccccaagg atggtgaagc tcagcagggg tctgagggta gccggccaga | 1440 |
| agaggctgga acctcctgct caagtctaga cccctacttc tctgctgccc ccaccctgcc | 1500 |
| agagctgatg tttccaatac caagatgtct tcacagggca cagcccctgc agagcatctt | 1560 |
| ggtcatttgg aagaggacac ggtatcccct ctggccagag tatgtcagag aaggaagagt | 1620 |
| agggcttttt tgtttgttt tttttaaag gtgcttgctt gtttaatgta aataatagaa | 1680 |
| agccttaata tcttttctgt aacacggagt aatatttaa tgtcatgttt tggatgtaca | 1740 |
| taatatattt ataacaaagc agcaagagtc tactt | 1775 |

<210> SEQ ID NO 55
<211> LENGTH: 2097
<212> TYPE: DNA
<213> ORGANISM: Homo sapiens
<220> FEATURE:
<221> NAME/KEY: polyA_site
<222> LOCATION: (2097)..(2097)
<223> OTHER INFORMATION:

<400> SEQUENCE: 55

| | |
|---|---|
| gccgccatgt cgcggaggct gctgccccgg gcggagaagc ggcgtcggcg gctggagcag | 60 |
| aggcagcagc cggacgagca gcggaggcgg tcgggagcga tggtgaagat ggcggcggcg | 120 |
| ggcggcggag gcggcggtgg ccgctactac ggcggcggca gtgagggcgg ccgggcccct | 180 |
| aagcggctca agactgacaa cgccggcgac cagcacggag gcggcggcgg tggcggtgga | 240 |
| ggagccgggg cggcgggcgg cggcggcggt ggggagaact acgatgaccc gcacaaaacc | 300 |
| cctgcctccc cagttgtcca catcaggggc ctgattgacg gtgtggtgga agcagacctt | 360 |
| gtggaggcct tgcaggagtt tggacccatc agctatgtgg tggtaatgcc taaaaagaga | 420 |
| caagcactgg tggagtttga agatgtgttg ggggcttgca acgcagtgaa ctacgcagcc | 480 |
| gacaaccaaa tatacattgc tggtcaccca gcttttgtca actactctac cagccagaag | 540 |
| atctcccgcc ctggggactc ggatgactcc cggagcgtga acagtgtgct tctctttacc | 600 |
| atcctgaacc ccatttattc gatcaccacg gatgttcttt acactatctg taatccttgt | 660 |
| ggccctgtcc agagaattgt cattttcagg aagaatggag ttcaggcgat ggtggaattt | 720 |
| gactcagttc aaagtgccca gcgggccaag gcctctctca tggggctga tatctattct | 780 |
| ggctgttgca ctctgaagat cgaatacgca aagcctacac gcttgaatgt gttcaagaat | 840 |
| gatcaggata cttgggacta cacaaacccc aatctcagtg acaaggtga ccctggcagc | 900 |
| aaccccaaca acgccagag gcagccccct ctcctgggag atcacccgc agaatatgga | 960 |
| gggcccacg tgggtacca cagccattac catgatgagg gctacgggcc cccccacct | 1020 |
| cactacgaag ggagaaggat gggtccacca gtgggggtc accgtcgggg cccaagtcgc | 1080 |
| tacgcccccc agtatgggca ccccccaccc cctcccccac cacccgagta tggccctcac | 1140 |
| gccgacagcc ctgtgctcat ggtctatggc ttggatcaat ctaagatgaa cggtgaccga | 1200 |

-continued

```
gtcttcaatg tcttctgctt atatggcaat gtggagaagg tgaaattcat gaaaagcaag    1260 ccggggggccg ccatggtgga gatggctgat ggctacgctg tagaccgggc cattacccac    1320
ctcaacaaca acttcatgtt tgggcagaag ctgaatgtct gtgtctccaa gcagccagcc    1380
atcatgcctg gtcagtcata cgggttggaa gacgggtctt gcagttacaa agacttcagt    1440
gaatcccgga acaatcggtt ctccacccca gagcaggcag ccaagaaccg catccagcac    1500
cccagcaacg tgctgcactt cttcaacgcc ccgctggagg tgaccgagga aacttctttg    1560
gagatctgcg atgagctggg agtgaagcgg ccatcttctg tgaaagtatt ctcaggcaaa    1620
agtgagcgca gctcctctgg actgctggag tgggaatcca agagcgatgc cctggagact    1680
ctgggcttcc tgaaccatta ccagatgaaa aacccaaatg gtccataccc ttacactctg    1740
aagttgtgtt tctccactgc tcagcacgcc tcctaattag gtgcctagga agagtcccat    1800
ctgagcagga agacatttct cttctcctta tgccattttt tgtttttgtt atttgcaaaa    1860
gatcttgtat tcctttttttt tttttttttt ttttttaaat gctaggtttg tagaggctta    1920 cttaaccttta atggaaacgc tggaaatctg caggggagg gaaaggggaa ctgttatctc    1980
ccaagattaa ccttcacttt taaaaaatta ttggacatgt gaattttttt tttcctggtc    2040
atacatttgg gctgcccatg tactcttggc ccatttcaat aaaattgttt ggaaaat       2097
```

```
<210> SEQ ID NO 56
<211> LENGTH: 2243
<212> TYPE: DNA
<213> ORGANISM: Homo sapiens
<220> FEATURE:
<221> NAME/KEY: polyA_site
<222> LOCATION: (2243)..(2243)
<223> OTHER INFORMATION:

<400> SEQUENCE: 56
```

```
atggcgtcca tgcgggagag cgacacgggc ctgtggctgc acaacaagct gggggccacg      60
gacgagctgt angcgccgcc cagcatcgcg tccctgctca cggccgcaat catcgacaac     120
atccgtctct gcttccatgg cctctcgtcg gcgtccctgc tcacggccgc ggtcatcgac     180
aacatccgtc tctgcttcca tggcctctcg tcggcagtga agctcaagtt gctactcggg     240
acgctgcacc tcccgcgccg cacggtggac gagatgaagg gcgccctaat ggagatcatc     300
cagctcgcca gcctcgactc ggacccctgg gtgctcatgg tcgccgacat cttgaagtcc     360
tttccggaca caggctcgct taacctggag ctggaggagc agaatcccaa cgttcaggat     420
attttgggag aacttagaga aaaggtgggt gagtgtgaag cgtctgccat gctgccactg     480
gagtgccagt acttgaacaa aaacgccctg acgaccctcg cgggacccct cactcccccg     540
gtgaagcatt ttcagttaaa gcggaaaccc aagagcgcca cgctgcgggc ggagctgctg     600
cagaagtcca cggagaccgc ccagcagttg aagcggagcg ccggggtgcc cttccacgcc     660
aagggccggg ggctgctgcg gaagatggac accaccaccc cactcaaagg catcccgaag     720
caggcgccct tcagaagccc cacgcgcgcc agcgtcttca gccccacagg gaaccggacc     780
cccatcccgc cttccaggac gctgctgcgg aaggaacgag gtgtgaagct gctggacatc     840
tctgagctgg atatggttgg cgctggccga gaggcgaagc ggagaaggaa gactctcgat     900
gcggaggtgg tggagaagcc ggccaaggag gaaacggtgg tggagaacgc cacccccggac    960 tacgcagccg gctggtgtc cacgcagaaa cttgggtccc tgaacaatga gcctgcgctg    1020
ccctccacga gctaccttcc ctccacgccc agcgtggttc ccgcctcctc ctacatcccc    1080
```

-continued

```
agctccgaga cgcccccagc cccatcttcc cgggaagcca gccgcccacc agaggagccc    1140
agcgccccga gccccacgtt gccagcgcag ttcaagcagc gggcgcccat gtacaacagc    1200
ggcctgagcc ctgccacacc cacgcctgcg gcgcccacct cgcctctgac acccaccaca    1260
cctccggctg tcgcccctac cactcagaca cccccggttg ccatggtggc cccgcagacc    1320
caggcccctg ctcagcagca gcctaagaag aacctgtccc tcacgagaga gcagatgttc    1380
gctgcccagg agatgttcaa gacggccaac aaagtcacgc ggcccgagaa ggccctcatc    1440
ctgggcttca tggccggctc ccgagagaac ccgtgccagg agcaggggga cgtgatccag    1500
atcaagctga gcgagcacac ggaggacctg cccaaggcgg acggccaggg tagcacaacc    1560
atgctggtgg acacagtgtt tgagatgaac tatgccacgg gccagtggac gcgcttcaag    1620
aagtacaagc ccatgaccaa tgtgtcctag aaccacctgc ctcacagctg gccgtcactt    1680 gtggggtcc acgggacgat ggctttgcca gcttaaagta accggatggc ggacacctgg    1740
cccccgaggt cccccggccg ccgccctgct gctgacccag cctgttttaa gttctggatg    1800
catttctctg gggtatttgg ggcttatttt taaaatttta atatgggttc ttttttgtgt    1860
gatttaagac acttttggaa ctcaacgtta cattttgaa tgtagtaagt aaattaacca    1920
aaaaagttac aacttcctaa ttttagtgac agctctgcct gttagactct actttttaa    1980 aatcttttct attttccctc gctggggcag tgccctccta cccccagggt tgaggggacc    2040
aaggtggcac ggtggtactg ggggtgcggc agggacaccc gaccacacca gagcgtggga    2100
gacggtgggc cttgtcccct gcctgtgcct gcctgggagt tttgtattca tcttttgtat    2160
agttgtggac atttaagaca gtctttgggt acctatttc attgtaaaac tatctgaacc    2220
attaaagtcg agcttttcta aag    2243
```

<210> SEQ ID NO 57
<211> LENGTH: 831
<212> TYPE: DNA
<213> ORGANISM: Homo sapiens
<220> FEATURE:
<221> NAME/KEY: polyA_site
<222> LOCATION: (831)..(831)
<223> OTHER INFORMATION:

<400> SEQUENCE: 57

```
gcgggagggc agcgagaggt tcgcgggtgc agcgcacagg agaccatgtc cgggggcagc      60
agctgcagcc agaccccaag ccgggccatc cccgccactc gccgggtggt gctcggcgac     120
ggcgtgcagc tcccgcccgg ggactacagc acgaccccg gcgcacgct cttcagcacc      180 accccgggag gtaccaggat catctatgac cggaaattcc tgatggagtg tcggaactca     240
cctgtgacca aaacacccc aagggatctg ccaccattc gggggtcac cagcccttcc       300 agtgatgagc ccccatgga agccagccag agccacctgc gcaatagccc agaagataag     360
cgggcgggcg gtgaagagtc acagtttgag atggacattt aaagcaccag ccatcgtgtg    420
gagcactacc aaggggcccc tcagggcctt cctgggagga gtcccaccag ccaggcctta    480
tgaaagtgat catactgggc aggcgttggc gtggggtcgg acaccccagc cctttctccc    540
tcactcaggg cacctgcccc ctcctcttcg tgaacaccag cagatacctc cttgtgcctc    600
cactgatgca ggagctgcca ccccaagggg agtgaccct gccagcacac cctgcagcca    660
agggccagga agtggacaag aacgaaccct tccttccgaa tgatcagcag ttccagcccc    720
tcgctgctgg gggcgcaacc accccttcct taggttgatg tgcttgggaa agctccctcc    780
ccctccttcc ccaagagagg aaataaaagc caccttcgcc ctagggccaa g             831
```

<210> SEQ ID NO 58
<211> LENGTH: 2404
<212> TYPE: DNA
<213> ORGANISM: Homo sapiens

<400> SEQUENCE: 58

| | | | | | |
|---|---|---|---|---|---|
| cacgcgtaag | cttgggcccc | tcgagggatc | ctctagagcg | gccgccgaga | cgtccccggc | 60 |
| acgctgatgg | agcccgggcg | cggcgcgggg | cccgcgggca | tggcggagcc | tcgggcgaag | 120 |
| gcggcgcggc | cggggcccca | gcgctttctg | cggcgcagcg | tggtagagtc | ggaccaggag | 180 |
| gagccgccgg | gcttggaggc | agccgaggcg | ccgggcccgc | agccccgca | gcccctgcag | 240 |
| cgccgggtgc | ttctgctctg | caagacgcgc | cgcctcatcg | cggagcgcgc | ccgcggacgc | 300 |
| cccgccgccc | ccgcgcccgc | agcgctggta | gcgcagccgg | gagccccgg | agccccgcg | 360 |
| gacgccggcc | ccgagcccgt | gggcacgcag | gagcccggcc | cggaccccat | cgcagccgct | 420 |
| gtcgaaaccg | cgcctgcccc | cgacggcggc | cccagggagg | aggcggcggc | taccgtgagg | 480 |
| aaggaggatg | aggggggcggc | cgaggcgaag | cctgagcccg | ggcgcactcg | ccgggacgag | 540 |
| cccgaagagg | aggaggacga | cgaggacgac | ctcaaggccg | tggccacctc | tctggacggc | 600 |
| cgcttcctca | gttcgacat | cgagctgggc | cgcggttcct | tcaagacggt | ctacaagggg | 660 |
| ctggacacgg | agacctgggt | ggaggtggcc | tggtgtgagc | tgcaggaccg | gaagctcacc | 720 |
| aagctggagc | ggcagcggtt | caaggaagag | gctgagatgc | tgaaaggcct | gcagcacccc | 780 |
| aacatcgtgc | gcttctacga | cttctgggag | tccagcgcca | agggcaagcg | gtgcattgtg | 840 |
| ctggtgacgg | agcttatgac | ctcagggacg | ctgaagacat | acctgaagcg | gttcaaggtg | 900 |
| atgaagccca | aggttctccg | cagctggtgc | cggcagatcc | tgaagggcct | gctgttcctg | 960 |
| cacacaagga | cgccacccat | catccaccga | gacctgaaat | gtgacaatat | tttcatcacc | 1020 |
| ggaccaactg | gtctgtgaa | gattggcgac | ttgggcctgg | ccactctgaa | aagagcgtca | 1080 |
| tttgccaaaa | gtgtgatagg | tactcccgag | ttcatggcgc | ccgagatgta | cgaggagcac | 1140 |
| tacgatgagt | ccgtggacgt | ctatgccttt | gggatgtgca | tgctggagat | ggccacctcg | 1200 |
| gagtacccct | actcggagtg | ccagaatgcg | gcccagatct | accgcaaggt | cacctgtggt | 1260 |
| atcaagccgg | ccagctttga | gaaagtgcac | gatcctgaaa | tcaaggagat | tattggggag | 1320 |
| tgtatctgca | aaaacaagga | ggaaaggtac | gagatcaaag | acctgctgag | ccacgccttc | 1380 |
| ttcgcagagg | acacaggcgt | gagggtggag | ctcgcggagg | aggaccacgg | caggaagtcc | 1440 |
| accatcgccc | tgaggctctg | ggtggaagac | cccaagaaac | tgaagggaaa | gcccaaggac | 1500 |
| aatggagcca | tagagttcac | cttcgacctg | gagaaggaga | cgccggatga | agtggcccaa | 1560 |
| gagatgattg | agtctggatt | cttccacgag | agtgacgtca | gatcgtggc | caagtccatc | 1620 |
| cgtgaccgcg | tggccttgat | ccagtggcgg | cgggagagga | tctggcccgc | gctgcagccc | 1680 |
| aaggagcagc | aggatgtggg | cagcccggac | aaggccaggg | gtccgccggt | gcccctgcag | 1740 |
| gtccaggtga | cctaccatgc | acaggctggg | cagcccgggc | caccagagcc | cgaggagccg | 1800 |
| gaggccgacc | agcacctcct | gccacctacg | ttgccgacca | gcgccacctc | cctggcctcg | 1860 |
| gacagcacct | tcgacagcgg | ccagggctct | accgtgtact | cagactcgca | gagcagccag | 1920 |
| cagagcgtga | tgcttggctc | ccttgccgac | gcagcgccgt | ccccggccca | gtgtgtgtgc | 1980 |
| agccccctg | tgagcgaggg | gcccgtcctg | ccgcagagcc | tgcccctcgct | gggggcctac | 2040 |
| cagcagccca | cggctgcacc | tcctccgctg | gcccagccga | caccctgcc | gcaggtcctg | 2100 |

-continued

| | |
|---|---|
| gccccacagc ccgtggtccc cctccagccg gttccccccc acctgccacc gtacctggct | 2160 |
| ccagcctccc aggtgggggc ccccgctcag ctgaagcccc tccagatgcc acaggcgccc | 2220 |
| ctgcagccgc ttgctcaagt ccctccgcag atgcccccga ttcctgttgt gccccccatc | 2280 |
| acgccctgg cgggaatcga cggcctccct ccggccctcc cagacctgcc gaccgcgact | 2340 |
| gtgcctcccg tgccaccacc tcagtatttc tctccagccg tgatcttgcc gagccggacg | 2400 |
| cgtg | 2404 |

<210> SEQ ID NO 59
<211> LENGTH: 6707
<212> TYPE: DNA
<213> ORGANISM: Homo sapiens
<220> FEATURE:
<221> NAME/KEY: polyA_site
<222> LOCATION: (6707)..(6707)
<223> OTHER INFORMATION:

<400> SEQUENCE: 59

| | |
|---|---|
| cccaagtttg gggaagacag gaactgcagc gcccctcccc gtttcacgcc acgcgcggga | 60 |
| ccgaggacct aggacctggc cagctgggcg tggttcggag agccgggcgg gaaaacgaaa | 120 |
| ccagaaatcc gaaggccgcg ccagagccct gcttcccctt gcatctgcgc cgggaggcca | 180 |
| tggacttgta cagcaccccg gccgctgcgc tggacaggtt cgtggccaga aagctgcagc | 240 |
| cgcggaagga gttcgtagag aaggcgcggc gcgctctggg cgccctggcc gctgctctga | 300 |
| gggagcgcgg gggccgcctc ggtgctgctg cccgcgggt gctgaaaact gtcaagggag | 360 |
| gctcctcggg ccggggcaca gctctcaagg gtggctgtga ttctgaactt gtcatcttcc | 420 |
| tcgactgctt caagagctat gtggaccaga ggggcccgccg tgcagagatc ctcagtgaga | 480 |
| tgcgggcatc gctggaatcc tggtggcaga acccagtccc tggtctgaga ctcacgtttc | 540 |
| ctgagcagag cgtgcctggg gccctgcagt tccgcctgac atccgtagat cttgaggact | 600 |
| ggatggatgt tagcctggtg cctgccttca atgtcctggg tcaggccggc tccggcgtca | 660 |
| aacccaagcc acaagtctac tctaccctcc tcaacagtgg ctgccaaggg ggcgagcatg | 720 |
| cggcctgctt cacagagctg cggaggaact ttgtgaacat tcgcccagcc aagttgaaga | 780 |
| acctaatctt gctggtgaag cactggtacc accaggtgtg cctacagggg ttgtggaagg | 840 |
| agacgctgcc cccggtctat gccctggaat tgctgaccat cttcgcctgg gagcagggct | 900 |
| gtaagaagga tgcttttcagc ctagccgaag gcctccgaac tgtcctgggc ctgatccaac | 960 |
| agcatcagca cctgtgtgtt ttctggactg tcaactatgg cttcgaggac cctgcagttg | 1020 |
| ggcagttctt gcagcggcag cttaagagac ccaggcctgt gatcctggac ccagctgacc | 1080 |
| ccacatggga cctggggaat ggggcagcct ggcactggga tttgctagcc caggaggcag | 1140 |
| catcctgcta tgaccaccca tgcttctga gggggatggg ggaccagtg cagtcttgga | 1200 |
| aggggccggg ccttccacgt gctggatgct caggtttggg ccaccccatc cagctagacc | 1260 |
| ctaaccagaa gaccctgaa aacagcaaga gcctcaatgc tgtgtaccca agagcaggga | 1320 |
| gcaaacctcc ctcatgccca gctcctggcc ccactgggc agccagcatc gtcccctctg | 1380 |
| tgccgggaat ggccttggac ctgtctcaga tccccaccaa ggagctggac cgcttcatcc | 1440 |
| aggaccacct gaagccgagc ccccagttcc aggagcaggt gaaaaaggcc atcgacatca | 1500 |
| tcttgcgctg cctccatgag aactgtgttc acaaggcctc aagagtcagt aaaggggct | 1560 |
| catttggccg gggcacagac ctaagggatg gctgtgatgt tgaactcatc atcttcctca | 1620 |
| actgcttcac ggactacaag gaccaggggc cccgccgcgc agagatcctt gatgagatgc | 1680 |

```
gagcgcacgt agaatcctgg tggcaggacc aggtgcccag cctgagcctt cagtttcctg   1740
agcagaatgt gcctgaggct ctgcagttcc agctggtgtc cacagccctg aagagctgga   1800
cggatgttag cctgctgcct gccttcgatg ctgtggggca gctcagttct ggcaccaaac   1860
caaatcccca ggtctactca aggctcctca ccagtggctg ccaggagggc gagcataagg   1920
cctgcttcgc agagctgcgg aggaacttca tgaacattcg ccctgtcaag ctgaagaacc   1980
tgattctgct ggtgaagcac tggtaccgcc aggttgcggc tcagaacaaa ggaaaaggac   2040
cagcccctgc ctctctgccc ccagcctatg ccctggagct cctcaccatc tttgcctggg   2100
agcagggctg caggcaggat tgtttcaaca tggcccaagg cttccggacg tgctggggc    2160 tcgtgcaaca gcatcagcag ctctgtgtct actggacggt caactatagc actgaggacc   2220
cagccatgag aatgcacctt cttggccagc ttcgaaaacc cagacccctg gtcctggacc   2280
ccgctgatcc cacctggaac gtgggccacg gtagctggga gctgttggcc caggaagcag   2340
cagcgctggg gatgcaggcc tgcttttctga gtagagacgg gacatctgtg cagccctggg   2400
atgtgatgcc agccctcctt taccaaaccc cagctgggga ccttgacaag ttcatcagtg   2460
aatttctcca gcccaaccgc cagttcctgg cccaggtgaa caaggccgtt gataccatct   2520
gttcattttt gaaggaaaac tgcttccgga attctcccat caaagtgatc aaggtggtca   2580
agggtggctc ttcagccaaa ggcacagctc tgcgaggccg ctcagatgcc gacctcgtgg   2640
tgttcctcag ctgcttcagc cagttcactg agcagggcaa caagcgggcc gagatcatct   2700
ccgagatccg agcccagctg gaggcatgtc aacaggagcg gcagttcgag gtcaagtttg   2760
aagtctccaa atgggagaat ccccgcgtgc tgagcttctc actgacatcc cagacgatgc   2820
tggaccagag tgtggacttt gatgtgctgc agcctttga cgccctaggc cagctggtct   2880
ctggctccag gcccagctct caagtctacg tcgacctcat ccacagctac agcaatgcgg   2940
gcgagtactc cacctgcttc acagagctac aacgggactt catcatctct cgccctacca   3000
agctgaagag cctgatccgg ctggtgaagc actggtacca gcagtgtacc aagatctcca   3060
aggggagagg ctccctaccc ccacagcacg ggctggaact cctgactgtg tatgcctggg   3120
agcagggccg gaaggactcc cagttcaaca tggctgaggg cttccgcacg gtcctggagc   3180
tggtcaccca gtaccgccag ctctgtatct actggaccat caactacaac gccaaggaca   3240
agactgttgg agacttcctg aaacagcagc ttcagaagcc caggcctatc atcctggatc   3300
cggctgaccc gacaggcaac ctgggccaca atgcccgctg ggacctgctg gccaaggaag   3360
ctgcagcctg cacatctgcc ctgtgctgca tgggacggaa tggcatcccc atccagccat   3420
ggccagtgaa ggctgctgtg tgaagttgag aaaatcagcg gtcctactgg atgaagagaa   3480
gatggacacc agccctcagc atgaggaaat tcagggtccc ctaccagatg agagagattg   3540
tgtacatgtg tgtgtgagca catgtgtgca tgtgtgtgca cacgtgtgca tgtgtgtgtt   3600
ttagtgaatc tgctctccca gctcacacac tcccctgcct cccatggctt acacactagg   3660
atccagactc catggtttga caccagcctg cgtttcagc ttctctgtca cttccatgac    3720
tctatcctca taccaccact gctgcttccc acccagctga gaatgccccc tcctccctga   3780
ctcctctctg cccatgcaaa ttagctcaca tctttcctcc tgctgcaatc catcccttcc   3840
tcccattggc ctctccttgc caaatctaaa tactttatat agggatggca gagagttccc   3900
atctcatctg tcagccacag tcatttggta ctggctacct ggagcctat cttctgaagg    3960 gttttaaaga atggccaatt agctgagaag aattatctaa tcaattagtg atgtctgcca   4020
```

```
tggatgcagt agaggaaagt ggtggtacaa gtgccatgat tgattagcaa tgtctgcact    4080
ggatatggaa aaaagaaggt gcttgcaggt ttacagtgta tatgtgggct attgaagagc    4140
cctctgagct cggttgctag caggagagca tgcccatatt ggcttacttt gtctgccaca    4200
gacacagaca gagggagttg ggacatgcat gctatgggga ccctcttgtt ggacacctaa    4260
ttggatgcct cttcatgaga ggcctccttt tcttcacctt ttatgctgca ctcctcccct    4320
agtttacaca tcttgatgct gtggctcagt ttgccttcct gaattttat tgggtccctg    4380 tttctctcc taacatgctg agattctgca tccccacagc ctaaactgag ccagtggcca    4440
aacaaccgtg ctcagcctgt ttctctctgc cctctagag aaggcccacc aggtccatcc    4500
aggaggctct cctgacctca gtccaacaa cagtgtccac actagtcaag gttcagccca    4560
gaaaacagaa agcactctag gaatcttagg cagaaaggga ttttatctaa atcactggaa    4620
aggctggagg agcagaaggc agaggccacc actggactat tggtttcaat attagaccac    4680
tgtagccgaa tcagaggcca gagagcagcc actgctactg ctaatgccac cactacccct    4740
gccatcactg ccccacatgg acaaaactgg agtcgagacc taggttagat tcctgcaacc    4800
acaaacatcc atcagggatg gccagctgcc agagctgcgg gaagacggat cccacctccc    4860
tttcttagca gaatctaaat tacagccaga cctctggctg cagaggagtc tgagacatgt    4920
atgattgaat gggtgccaag tgccaggggg cggagtcccc agcagatgca tcctggccat    4980
ctgttgcgtg gatgagggag tgggtctatc tcagaggaag gaacaggaaa caaagaaagg    5040
aagccactga acatcccttc tctgctccac aggagtgtct tagacagcct gactctccac    5100
aaaccactgt taaaacttac ctgctaggaa tgctagattg aatgggatgg gaagagcctt    5160
ccctcattat tgtcattctt ggagagaggt gagcaaccaa gggaagctcc tctgattcac    5220
ctagaacctg ttctctgccg tctttggctc agcctacaga gactagagta ggtgaaggga    5280
cagaggacag ggcttctaat acctgtgcca tattgacagc ctccatccct gtccccatc    5340 ttggtgctga accaacgcta agggcacctt cttagactca cctcatcgat actgcctggt    5400
aatccaaagc tagaactctc aggaccccaa actccacctc ttggattggc cctggctgct    5460
gccacacaca tatccaagag ctcagggcca gttctggtgg gcagcagaga cctgctctgc    5520
caagttgtcc agcagcagag tggccctggc ctgggcatca caagccagtg atgctcctgg    5580
gaagaccagg tggcaggtcg cagttgggta ccttccattc ccaccacaca gactctgggc    5640
ctccccgcaa aatggctcca gaattagagt aattatgaga tggtgggaac cagagcaact    5700
caggtgcatg atacaaggag aggttgtcat ctgggtaggg cagagaggag ggcttgctca    5760
tctgaacagg ggtgtatttc attccaggcc ctcagtcttt ggcaatggcc accctggtgt    5820
tggcatattg gccccactgt aacttttggg ggcttcccgg tctagccaca ccctcggatg    5880
gaaagacttg actgcataaa gatgtcagtt ctccctgagt tgattgatag cttaatggt    5940 cacccctaaaa acacccacat atgcttttcg atggaaccag ataagttgac gctaaagttc    6000
ttatggaaaa atacacacgc aatagctagg aaaacacagg gaaagaagag ttctgagcag    6060
ggcctagtct tagccaatat taaaacatac tatgaagcct ctgatactta aacagcatgg    6120
cgctggtacg taaatagacc aatgcagtta ggtggctctt tccaagactc tggggaaaaa    6180
agtagtaaaa agctaaatgc aatcaatcag caattgaaag ctaagtgaga gagccagagg    6240
gcctccttgg tggtaaaaga gggttgcatt tcttgcagcc agaaggcaga gaaagtgaag    6300
accaagtcca gaactgaatc ctaagaaatg caggactgca aagaaattgg tgtgtgtgtg    6360
tgtgtgtgtg tgtttaattt ttaaaaagtt tttattgaga tacaagtcaa taccataaag    6420
```

```
ctctcaccct tctaaagtgt acaattcagt ggtgtgagta tattcataag atttatactt    6480
ggtgtctatt cataagactt atatccagca tattcataac tagagccata tcacagatgc    6540
attcatcata ataattccag acattttcat caccctaaaa ggaaaccctg aaacccatta    6600
gcagtcattc cccattcctc aacccattc tctccctaat ccctagaaac caccaatctg    6660
ctgtgtattt catctattgc caacatttca tataaatggc atcatac                  6707

<210> SEQ ID NO 60
<211> LENGTH: 769
<212> TYPE: DNA
<213> ORGANISM: Homo sapiens
<220> FEATURE:
<221> NAME/KEY: polyA_site
<222> LOCATION: (769)..(769)
<223> OTHER INFORMATION:

<400> SEQUENCE: 60
gcgtcaagaa cttcatcctg cagccgacg tcatgaagag catttcgctg ctgcgctacc      60
aggaggaaag caagacgctg agcctggtgt cgcgggatgc caagcccctg gaggtgtaca   120
gcgtggactt catggtggac aatgcccagc tgggttttct ggtgtctgac cgcgaccgca   180
acctcatggt gtacatgtac ctgccccgaag ccaaggagag tttcggggggc atgcgcctgc   240 tgcgtcgggc agacttccac gtgggtgccc acgtgaacac gttctggagg accccgtgcc   300 gggggggccac tgaagggctc agcaaaaagt cggtcgtgtg ggagaataag cacatcacgt   360
ggtttgccac cctggacggc ggcatcgggc tgctgctgcc catgcaggag aagacctacc   420
ggcggctgct gatgctgcag aacgcgctga ccaccatgct gccacaccac gccggcctca   480
acccccgcgc cttccggatg ctgcacgtgg accgccgcac cctccagaat gccgtgcgca   540
acgtgctgga tggggagctg ctcaaccgct acctgtacct gagcaccatg gagcgcagcg   600
agctagccaa gaagatcggc accacaccag acataatcct ggacgacttg ctggagacgg   660
accgcgtcac cgcccacttc tagccccgtg gatgccgtca ccaccagcac acggaactac   720
ctcccacccc cttttttgtac aaaacacaag gaaaaacatt ttttgcttg               769

<210> SEQ ID NO 61
<211> LENGTH: 2039
<212> TYPE: DNA
<213> ORGANISM: Homo sapiens
<220> FEATURE:
<221> NAME/KEY: polyA_site
<222> LOCATION: (2039)..(2039)
<223> OTHER INFORMATION:

<400> SEQUENCE: 61
gagggccaca gtgggattaa aaagaccact gaggagcagg tgcaggccag cactccttgc      60
ccgaggacag agatggcgag cgcccggatt ggggatgagt atgcggagga cagctctgat   120
gaggaggaca tccggaacac ggtgggcaac gtgcccttgg agtggtacga tgacttcccc   180
cacgtgggct acgacctgga tgcaggcgc atctacaagc ccctgcggac ccgggatgag   240
ctggaccagt tcctggacaa gatggacgat cctgactact ggcgcaccgt gcaggacccg   300
atgacagggc gggacctgag actgacggat gagcaggtgg ccctggtgcg gcggctgcag   360
agtggccagt ttggggatgt gggcttcaac ccctatgagc cggctgtcga cttcttcagc   420
ggggacgtca tgatccaccc ggtgaccaac cgcccggccg acaagcgcag cttcatcccc   480
tccctggtgg agaaggagaa ggtctctcgc atggtgcacg ccatcaagat gggctggatc   540
```

| | |
|---|---:|
| cagcctcgcc ggccccgaga ccccacccce agcttctatg acctgtgggc ccaggaggac | 600 |
| cccaacgccg tgctcgggcg ccacaagatg cacgtacctg ctcccaagct ggccctgcca | 660 |
| ggccacgccg agtcgtacaa cccacccccct gaatacctgc tcagcgagga ggagcgcttg | 720 |
| gcgtgggaac agcaggagcc aggcgagagg aagctgagct ttttgccacg caagttcccg | 780 |
| agcctgcggg ccgtgcctgc ctacggacgc ttcatccagg aacgcttcga gcgctgcctt | 840 |
| gacctgtacc tgtgcccacg gcagcgcaag atgagggtga atgtagaccc tgaggacctc | 900 |
| atccccaagc tgcctcggcc gagggacctg cagcccttcc ccacgtgcca ggccctggtc | 960 |
| tacagggcc acagtgacct tgtccggtgc ctcagtgtct ctcctggggg ccagtggctg | 1020 |
| gtttcaggct ctgacgacgg ctccctgcgg ctctgggagg tggccactgc ccgctgtgtg | 1080 |
| aggactgttc ccgtgggggg cgtggtgaag agtgtggcct ggaacccag cccgctgtc | 1140 |
| tgcctggtgg ctgcagccgt ggaggactcg gtgctgctgc tgaacccagc tctggggac | 1200 |
| cggctggtgg cgggcagcac agatcagctg ttgagcgcct tcgtcccgcc tgaggagccc | 1260 |
| cccttgcagc cggcccgctg gctggaggcc tcagaggagg agcgccaagt gggcctgcgg | 1320 |
| ctgcgcatct gccacgggaa gccagtgacg caggtgacct ggcacgggcg tggggactac | 1380 |
| ctggccgtgg tgctggccac ccaaggccac acccaggtgc tgattcacca gctgagccgt | 1440 |
| cgccgcagcc agagtccgtt ccgccgcagc acggacagg tgcagcgagt ggccttccac | 1500 |
| cctgcccggc ccttcctgtt ggtggcgtcc cagcgcagcg tccgcctcta ccacctgctg | 1560 |
| cgccaggagc tcaccaagaa gctgatgccc aactgcaagt gggtgtccag cctggcggtg | 1620 |
| caccctgcag gtgacaacgt catctgtggg agctacgata caagctggt gtggtttgac | 1680 |
| ctggatcttt ccaccaagcc atacaggatg ctgagacacc acaagaaggc tctgcgggct | 1740 |
| gtggccttcc acccgcggta cccactcttt gcgtcaggct cggacgacgg cagtgtcatc | 1800 |
| gtctgccatg gcatggtgta caatgacctt ctgcagaacc ccttgctggt gcccgtcaag | 1860 |
| gtgctgaagg gacacgtgct gacccgagat ctgggagtgc tggacgtcat cttccaccc | 1920 |
| acccagccgt gggtcttctc ctcggggggca gacgggactg tccgcctctt cacctagctg | 1980 |
| ttctgcctgc ctggggctgg ggtggtcgtg ctgaagtcaa cagagccttt accctgtgc | 2039 |

<210> SEQ ID NO 62
<211> LENGTH: 1822
<212> TYPE: DNA
<213> ORGANISM: Homo sapiens
<220> FEATURE:
<221> NAME/KEY: polyA_site
<222> LOCATION: (1822)..(1822)
<223> OTHER INFORMATION:

<400> SEQUENCE: 62

| | |
|---|---:|
| cggcctgcag ctcgcaggcg ccgcgtagcc gtcgccaccg ccgccagccc gtgcgccctc | 60 |
| ggcggtaccc gccgcgctcc catccccgcc gccggccagg ggcgcgctcg gccgccccgg | 120 |
| acagtgtccc gctgcggctc cgcggcgatg gccaccaaga tcgacaaaga ggcttgccgg | 180 |
| gcggcgtaca acctggtgcg cgacgacggc tcggccgtca tctgggtgac ttttaaatat | 240 |
| gacggctcca ccatcgtccc cggcgagcag ggagcggagt accagcactt catccagcag | 300 |
| tgcacagatg acgtccggtt gtttgccttc gtgcgcttca ccaccgggga tgccatgagc | 360 |
| aagaggtcca agtttgccct catcacgtgg atcggtgaga acgtcagcgg gctgcagcgc | 420 |
| gccaaaaccg ggacgacaa gaccctggtg aaggaggtcg tacagaattt cgctaaggag | 480 |
| tttgtgatca gtgatcggaa ggagctggag gaagatttca tcaagagcga gctgaagaag | 540 |

-continued

```
gcgggggag   ccaattacga   cgcccagacg   gagtaacccc   agcccccgcc   acaccacccc    600
ttgccaaagt   catctgcctg   ctccccgggg   gagaggaccg   ccggcctcag   ctactagccc    660
accagcccac   cagggagaag   agaagccatg   agaggcagcg   cccgccaccc   tgtgtccaca    720
gcccccacct   tcccgcttcc   cttagaaccc   tgccgtgtcc   tatctcatga   cgctcatgga    780
acctcttcct   ttgatcttct   ttttcttttc   tccccctctt   ttttgttcta   aagaaaagtc    840
attttgatgc   aaggtcctgc   ctgccatcag   atccgaggtg   cctcctgcag   tgacccctt    900
tcctggcatt   tctcttccac   gcgacgaggt   ctgcctagtg   agatctgcat   gacctcacgt    960
tgctttccag   agcccgggcc   tattttgcca   tctcagtttt   cctgggccct   gcttcctgtg   1020
taccactgag   gggcagctgg   gccaggagct   gtgcccggtg   cctgcagcct   tcataagcac   1080
acacgtccat   tccctactaa   ggcccagacc   tcctggtatc   tgccccgggc   tccctcatcc   1140
cacctccatc   cggagttgcc   caagatgcat   gtccagcata   ggcaggattg   ctcggtggtg   1200
agaaggttag   gtccggctca   gactgaataa   gaagagataa   aatttgcctt   aaaacttacc   1260
tggcagtggc   tttgctgcac   ggtctgaaac   cacctgttcc   caccctcttg   accgaaattt   1320
ccttgtgaca   cagagaaggg   caaaggtctt   gagcccagag   ttgacggagg   gagtatttca   1380
gggttcactt   caggggctcc   caaagcgaca   agatcgttag   ggagagaggc   ccagggtggg   1440
gactgggaat   taaggagag    ctgggaacgg   atcccttagg   ttcaggaagc   ttctgtgcaa   1500
gctgcgagga   tggcttgggc   cgaagggttg   ctctgcccgc   cgcgctagct   gtgagctgag   1560
caaagccctg   ggctcacagc   accccaaaag   cctgtggctt   cagtcctgcg   tctgcaccac   1620
acaatcaaaa   ggatcgtttt   gttttgtttt   taaagaaagg   tgagattggc   ttggttcttc   1680
atgagcacat   ttgatatagc   tcttttctg    tttttccttg   ctcatttcgt   tttggggaag   1740
aaatctgtac   tgtattggga   ttgtaaagaa   catctctgca   ctcagacagt   ttacagaaat   1800
aaatgttttt   tttgttttc    ag                                                   1822
```

```
<210> SEQ ID NO 63
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:45

<400> SEQUENCE: 63

Ala Leu Tyr Ser Pro Gly Lys Arg Leu
1               5

<210> SEQ ID NO 64
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:45

<400> SEQUENCE: 64

Ser Leu Ile Ala His Asn Leu Val His Leu
1               5                   10

<210> SEQ ID NO 65
<211> LENGTH: 9
<212> TYPE: PRT
<213> ORGANISM: Artificial
<220> FEATURE:
```

<223> OTHER INFORMATION: Designed peptide based on the amino acid
      sequence of SEQ ID NO:45

<400> SEQUENCE: 65

Leu Leu Leu Ala Arg Trp Glu Asp Thr
1               5

<210> SEQ ID NO 66
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:45

<400> SEQUENCE: 66

Leu Leu Ala Arg Trp Glu Asp Thr Pro Leu
1               5                   10

<210> SEQ ID NO 67
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:45

<400> SEQUENCE: 67

Ile Leu Gly Val Val Ala Gly Ala Leu Ile
1               5                   10

<210> SEQ ID NO 68
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:45

<400> SEQUENCE: 68

Ala Leu Ile Ala Asp Phe Leu Ser Gly Leu
1               5                   10

<210> SEQ ID NO 69
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:45

<400> SEQUENCE: 69

Phe Leu Ser Gly Leu Val His Trp Gly Ala
1               5                   10

<210> SEQ ID NO 70
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:45

<400> SEQUENCE: 70

Cys Leu Val Thr Leu Leu Pro Leu Leu
1               5

```
<210> SEQ ID NO 71
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:45

<400> SEQUENCE: 71

Thr Leu Leu Pro Leu Leu Asn Met Ala
1               5

<210> SEQ ID NO 72
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:45

<400> SEQUENCE: 72

Leu Leu Asn Met Ala Tyr Lys Phe Arg Thr
1               5                   10

<210> SEQ ID NO 73
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:45

<400> SEQUENCE: 73

Gln Leu Tyr Pro Trp Glu Cys Phe Val
1               5

<210> SEQ ID NO 74
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:45

<400> SEQUENCE: 74

Tyr Pro Trp Glu Cys Phe Val Phe Cys
1               5

<210> SEQ ID NO 75
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:45

<400> SEQUENCE: 75

Phe Val Phe Cys Leu Ile Ile Phe Gly Thr
1               5                   10

<210> SEQ ID NO 76
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:45

<400> SEQUENCE: 76
```

```
Phe Cys Leu Ile Ile Phe Gly Thr Phe Thr
1               5                   10
```

<210> SEQ ID NO 77
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:45

<400> SEQUENCE: 77

```
Cys Leu Ile Ile Phe Gly Thr Phe Thr
1               5
```

<210> SEQ ID NO 78
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:45

<400> SEQUENCE: 78

```
Ile Ile Phe Gly Thr Phe Thr Asn Gln Ile
1               5                   10
```

<210> SEQ ID NO 79
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:45

<400> SEQUENCE: 79

```
Gly Leu Pro Arg Trp Val Thr Leu Leu
1               5
```

<210> SEQ ID NO 80
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:45

<400> SEQUENCE: 80

```
Trp Val Thr Leu Leu Gln Asp Trp His Val
1               5                   10
```

<210> SEQ ID NO 81
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:45

<400> SEQUENCE: 81

```
Val Thr Leu Leu Gln Asp Trp His Val
1               5
```

<210> SEQ ID NO 82
<211> LENGTH: 9
<212> TYPE: PRT
<213> ORGANISM: Artificial

```
<220> FEATURE:
<223> OTHER INFORMATION: Designed peptide based on the amino acid
      sequence of SEQ ID NO:45

<400> SEQUENCE: 82

Thr Leu Leu Gln Asp Trp His Val Ile
1               5

<210> SEQ ID NO 83
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:45

<400> SEQUENCE: 83

Trp Leu Asn Tyr Pro Leu Glu Lys Ile
1               5

<210> SEQ ID NO 84
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:45

<400> SEQUENCE: 84

Arg Leu Glu Asp Leu Ile Gln Gly Leu
1               5

<210> SEQ ID NO 85
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:46

<400> SEQUENCE: 85

Gly Leu Ile Asp Gly Val Val Glu Ala
1               5

<210> SEQ ID NO 86
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:46

<400> SEQUENCE: 86

Gln Glu Phe Gly Pro Ile Ser Tyr Val
1               5

<210> SEQ ID NO 87
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:46

<400> SEQUENCE: 87

Val Met Pro Lys Lys Arg Gln Ala Leu
1               5
```

<210> SEQ ID NO 88
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:46

<400> SEQUENCE: 88

Tyr Ile Ala Gly His Pro Ala Phe Val
1               5

<210> SEQ ID NO 89
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:46

<400> SEQUENCE: 89

Val Leu Leu Phe Thr Ile Leu Asn Pro Ile
1               5                   10

<210> SEQ ID NO 90
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:46

<400> SEQUENCE: 90

Leu Leu Phe Thr Ile Leu Asn Pro Ile
1               5

<210> SEQ ID NO 91
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:46

<400> SEQUENCE: 91

Val Leu Tyr Thr Ile Cys Asn Pro Cys
1               5

<210> SEQ ID NO 92
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:46

<400> SEQUENCE: 92

Ile Val Ile Phe Arg Lys Asn Gly Val
1               5

<210> SEQ ID NO 93
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:46

```
<400> SEQUENCE: 93

Lys Met Asn Cys Asp Arg Val Phe Asn Val
1               5                   10

<210> SEQ ID NO 94
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:46

<400> SEQUENCE: 94

Met Asn Cys Asp Arg Val Phe Asn Val
1               5

<210> SEQ ID NO 95
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:46

<400> SEQUENCE: 95

Ile Met Pro Gly Gln Ser Tyr Gly Leu
1               5

<210> SEQ ID NO 96
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:46

<400> SEQUENCE: 96

Val Leu His Phe Phe Asn Ala Pro Leu
1               5

<210> SEQ ID NO 97
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:46

<400> SEQUENCE: 97

Lys Leu Cys Phe Ser Thr Ala Gln His Ala
1               5                   10

<210> SEQ ID NO 98
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:47

<400> SEQUENCE: 98

Ala Leu Met Glu Ile Ile Gln Leu Ala
1               5

<210> SEQ ID NO 99
<211> LENGTH: 9
<212> TYPE: PRT
```

```
<213> ORGANISM: Artificial
<220> FEATURE:
<223> OTHER INFORMATION: Designed peptide based on the amino acid
      sequence of SEQ ID NO:47

<400> SEQUENCE: 99

Ser Leu Asp Ser Asp Pro Trp Val Leu
1               5

<210> SEQ ID NO 100
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:47

<400> SEQUENCE: 100

Leu Glu Leu Glu Glu Gln Asn Pro Asn Val
1               5                   10

<210> SEQ ID NO 101
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:47

<400> SEQUENCE: 101

Ala Met Leu Pro Leu Glu Cys Gln Tyr Leu
1               5                   10

<210> SEQ ID NO 102
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:47

<400> SEQUENCE: 102

Tyr Leu Asn Lys Asn Ala Leu Thr Thr
1               5

<210> SEQ ID NO 103
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:47

<400> SEQUENCE: 103

Thr Leu Ala Gly Pro Leu Thr Pro Pro Val
1               5                   10

<210> SEQ ID NO 104
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:47

<400> SEQUENCE: 104

Gln Gln Leu Lys Arg Ser Ala Gly Val
1               5
```

```
<210> SEQ ID NO 105
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:47

<400> SEQUENCE: 105

Gly Leu Leu Arg Lys Met Asp Thr Thr
1               5

<210> SEQ ID NO 106
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:47

<400> SEQUENCE: 106

Lys Leu Leu Asp Ile Ser Glu Leu Asp Met
1               5                   10

<210> SEQ ID NO 107
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:47

<400> SEQUENCE: 107

Leu Leu Asp Ile Ser Glu Leu Asp Met Val
1               5                   10

<210> SEQ ID NO 108
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:47

<400> SEQUENCE: 108

Tyr Leu Pro Ser Thr Pro Ser Val Val
1               5

<210> SEQ ID NO 109
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:47

<400> SEQUENCE: 109

Thr Gln Thr Pro Pro Val Ala Met Val
1               5

<210> SEQ ID NO 110
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:47
```

<400> SEQUENCE: 110

Ser Leu Thr Arg Glu Gln Met Phe Ala
1               5

<210> SEQ ID NO 111
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:47

<400> SEQUENCE: 111

Glu Met Phe Lys Thr Ala Asn Lys Val
1               5

<210> SEQ ID NO 112
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:47

<400> SEQUENCE: 112

Lys Leu Ser Glu His Thr Glu Asp Leu
1               5

<210> SEQ ID NO 113
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:47

<400> SEQUENCE: 113

Thr Met Leu Val Asp Thr Val Phe Glu Met
1               5                   10

<210> SEQ ID NO 114
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:47

<400> SEQUENCE: 114

Met Leu Val Asp Thr Val Phe Glu Met
1               5

<210> SEQ ID NO 115
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:48

<400> SEQUENCE: 115

Val Val Leu Gly Asp Gly Val Gln Leu
1               5

<210> SEQ ID NO 116
<211> LENGTH: 10

```
<212> TYPE: PRT
<213> ORGANISM: Artificial
<220> FEATURE:
<223> OTHER INFORMATION: Designed peptide based on the amino acid
      sequence of SEQ ID NO:48

<400> SEQUENCE: 116

Gln Leu Pro Pro Gly Asp Tyr Ser Thr Thr
1               5                   10

<210> SEQ ID NO 117
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:48

<400> SEQUENCE: 117

Phe Leu Met Glu Cys Arg Asn Ser Pro Val
1               5                   10

<210> SEQ ID NO 118
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:49

<400> SEQUENCE: 118

Gly Met Ala Glu Pro Arg Ala Lys Ala
1               5

<210> SEQ ID NO 119
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:49

<400> SEQUENCE: 119

Val Leu Leu Leu Cys Lys Thr Arg Arg Leu
1               5                   10

<210> SEQ ID NO 120
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:49

<400> SEQUENCE: 120

Leu Leu Leu Cys Lys Thr Arg Arg Leu
1               5

<210> SEQ ID NO 121
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:49

<400> SEQUENCE: 121

Lys Gly Leu Asp Thr Glu Thr Trp Val
```

-continued

```
1               5

<210> SEQ ID NO 122
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:49

<400> SEQUENCE: 122

Gly Leu Asp Thr Glu Thr Trp Val Glu Val
1               5                   10

<210> SEQ ID NO 123
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:49

<400> SEQUENCE: 123

Glu Leu Gln Asp Arg Lys Leu Thr Lys Leu
1               5                   10

<210> SEQ ID NO 124
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:49

<400> SEQUENCE: 124

Lys Thr Tyr Leu Lys Arg Phe Lys Val
1               5

<210> SEQ ID NO 125
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:49

<400> SEQUENCE: 125

Arg Gln Ile Leu Lys Gly Leu Leu Phe Leu
1               5                   10

<210> SEQ ID NO 126
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:49

<400> SEQUENCE: 126

Phe Leu His Thr Arg Thr Pro Pro Ile
1               5

<210> SEQ ID NO 127
<211> LENGTH: 10
<212> TYPE: PRT
<213> ORGANISM: Artificial
<220> FEATURE:
<223> OTHER INFORMATION: Designed peptide based on the amino acid
``` sequence of SEQ ID NO:49

<400> SEQUENCE: 127

Phe Leu His Thr Arg Thr Pro Pro Ile Ile
1               5                   10

<210> SEQ ID NO 128
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:49

<400> SEQUENCE: 128

Lys Ile Gly Asp Leu Gly Leu Ala Thr Leu
1               5                   10

<210> SEQ ID NO 129
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:49

<400> SEQUENCE: 129

Ser Val Ile Gly Thr Pro Glu Phe Met Val
1               5                   10

<210> SEQ ID NO 130
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:49

<400> SEQUENCE: 130

Val Ile Gly Thr Pro Glu Phe Met Val
1               5

<210> SEQ ID NO 131
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:49

<400> SEQUENCE: 131

Lys Val His Asp Pro Glu Ile Lys Glu Ile
1               5                   10

<210> SEQ ID NO 132
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:49

<400> SEQUENCE: 132

Arg Leu Trp Val Glu Asp Pro Lys Lys Leu
1               5                   10

<210> SEQ ID NO 133

```
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:49

<400> SEQUENCE: 133

Gly Ala Thr Glu Phe Thr Phe Asp Leu
1               5

<210> SEQ ID NO 134
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 134

Lys Leu Gln Pro Arg Lys Glu Phe Val
1               5

<210> SEQ ID NO 135
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 135

Ala Leu Gly Ala Leu Ala Ala Ala Leu
1               5

<210> SEQ ID NO 136
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 136

Arg Leu Gly Ala Ala Ala Pro Arg Val
1               5

<210> SEQ ID NO 137
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 137

Phe Leu Asp Cys Phe Lys Ser Tyr Val
1               5

<210> SEQ ID NO 138
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 138
```

Ile Leu Ser Glu Met Arg Ala Ser Leu
1               5

<210> SEQ ID NO 139
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 139

Arg Leu Thr Phe Pro Glu Gln Ser Val
1               5

<210> SEQ ID NO 140
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 140

Ala Leu Gln Phe Arg Leu Thr Ser Val
1               5

<210> SEQ ID NO 141
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 141

Val Leu Gly Gln Ala Gly Ser Gly Val
1               5

<210> SEQ ID NO 142
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 142

Leu Leu Val Lys His Trp Tyr His Gln Val
1               5                   10

<210> SEQ ID NO 143
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 143

Gly Leu Trp Lys Glu Thr Leu Pro Pro Val
1               5                   10

<210> SEQ ID NO 144
<211> LENGTH: 10
<212> TYPE: PRT
<213> ORGANISM: Artificial
<220> FEATURE:

-continued

<223> OTHER INFORMATION: Designed peptide based on the amino acid
      sequence of SEQ ID NO:50

<400> SEQUENCE: 144

Thr Leu Pro Pro Val Tyr Ala Leu Glu Leu
1               5                   10

<210> SEQ ID NO 145
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 145

Ser Leu Ala Glu Gly Leu Arg Thr Val
1               5

<210> SEQ ID NO 146
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 146

Gly Leu Ile Gln Gln His Gln His Leu
1               5

<210> SEQ ID NO 147
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 147

Gly Leu Pro Arg Ala Gly Cys Ser Gly Leu
1               5                   10

<210> SEQ ID NO 148
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 148

Cys Leu His Glu Asn Cys Val His Lys Ala
1               5                   10

<210> SEQ ID NO 149
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 149

Ile Leu Asp Glu Met Arg Ala Gln Leu
1               5

<210> SEQ ID NO 150
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 150

Ser Leu Gln Phe Pro Glu Gln Asn Val
1               5

<210> SEQ ID NO 151
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 151

Asn Val Pro Glu Ala Leu Gln Phe Gln Leu
1               5                   10

<210> SEQ ID NO 152
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 152

Ser Leu Leu Pro Ala Phe Asp Ala Val
1               5

<210> SEQ ID NO 153
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 153

Phe Met Asn Ile Arg Pro Val Lys Leu
1               5

<210> SEQ ID NO 154
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 154

Leu Leu Val Lys His Trp Tyr Arg Gln Val
1               5                   10

<210> SEQ ID NO 155
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 155

```
Ser Leu Pro Pro Ala Tyr Ala Leu Glu Leu
1               5                   10

<210> SEQ ID NO 156
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 156

Gly Leu Val Gln Gln His Gln Gln Leu
1               5

<210> SEQ ID NO 157
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 157

Leu Leu Ala Gln Glu Ala Ala Ala Leu
1               5

<210> SEQ ID NO 158
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 158

Ala Leu Gly Met Gln Ala Cys Phe Leu
1               5

<210> SEQ ID NO 159
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 159

Phe Leu Ser Arg Asp Gly Thr Ser Val
1               5

<210> SEQ ID NO 160
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 160

Phe Leu Gln Pro Asn Arg Gln Phe Leu
1               5

<210> SEQ ID NO 161
<211> LENGTH: 9
<212> TYPE: PRT
<213> ORGANISM: Artificial
```

```
<220> FEATURE:
<223> OTHER INFORMATION: Designed peptide based on the amino acid
      sequence of SEQ ID NO:50

<400> SEQUENCE: 161

Phe Leu Ala Gln Val Asn Lys Ala Val
1               5

<210> SEQ ID NO 162
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 162

Phe Leu Ser Cys Phe Ser Gln Phe Thr
1               5

<210> SEQ ID NO 163
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 163

Cys Gln Gln Glu Arg Gln Phe Glu Val
1               5

<210> SEQ ID NO 164
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 164

Arg Gln Phe Glu Val Lys Phe Glu Val
1               5

<210> SEQ ID NO 165
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 165

Met Leu Asp Gln Ser Val Asp Phe Asp Val
1               5                   10

<210> SEQ ID NO 166
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 166

Ser Leu Pro Pro Gln His Gly Leu Glu Leu
1               5                   10
```

```
<210> SEQ ID NO 167
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 167

Asn Met Ala Glu Gly Phe Arg Thr Val Leu
1               5                   10

<210> SEQ ID NO 168
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 168

Asn Met Ala Glu Gly Phe Arg Thr Val
1               5

<210> SEQ ID NO 169
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 169

Arg Gln Leu Cys Ile Tyr Trp Thr Ile
1               5

<210> SEQ ID NO 170
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 170

Asn Leu Gly His Asn Ala Arg Trp Asp Leu
1               5                   10

<210> SEQ ID NO 171
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:50

<400> SEQUENCE: 171

Gly Ile Pro Ile Gln Pro Trp Pro Val
1               5

<210> SEQ ID NO 172
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:52
```

```
<400> SEQUENCE: 172

Lys Met Asp Asp Pro Asp Tyr Trp Arg Thr
1               5                   10

<210> SEQ ID NO 173
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:52

<400> SEQUENCE: 173

Arg Leu Thr Asp Glu Gln Val Ala Leu
1               5

<210> SEQ ID NO 174
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:52

<400> SEQUENCE: 174

Arg Leu Gln Ser Gly Gln Phe Gly Asp Val
1               5                   10

<210> SEQ ID NO 175
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:52

<400> SEQUENCE: 175

Val Leu Gly Arg His Lys Met His Val
1               5

<210> SEQ ID NO 176
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:52

<400> SEQUENCE: 176

Lys Met His Val Pro Ala Pro Lys Leu
1               5

<210> SEQ ID NO 177
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:52

<400> SEQUENCE: 177

Tyr Leu Leu Ser Glu Glu Glu Arg Leu
1               5

<210> SEQ ID NO 178
<211> LENGTH: 9
<212> TYPE: PRT
```

```
<213> ORGANISM: Artificial
<220> FEATURE:
<223> OTHER INFORMATION: Designed peptide based on the amino acid
      sequence of SEQ ID NO:52

<400> SEQUENCE: 178

Phe Leu Pro Arg Lys Phe Pro Ser Leu
1               5

<210> SEQ ID NO 179
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:52

<400> SEQUENCE: 179

Phe Ile Gln Glu Arg Phe Glu Arg Cys
1               5

<210> SEQ ID NO 180
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:52

<400> SEQUENCE: 180

Ala Leu Val Tyr Arg Gly His Ser Asp Leu
1               5                   10

<210> SEQ ID NO 181
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:52

<400> SEQUENCE: 181

Leu Val Tyr Arg Gly His Ser Asp Leu
1               5

<210> SEQ ID NO 182
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:52

<400> SEQUENCE: 182

Ser Val Ser Pro Gly Gly Gln Trp Leu
1               5

<210> SEQ ID NO 183
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:52

<400> SEQUENCE: 183

Leu Leu Asn Pro Ala Leu Gly Asp Arg Leu
1               5                   10
```

<210> SEQ ID NO 184
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:52

<400> SEQUENCE: 184

Val Leu Ala Thr Gln Gly His Thr Gln Val
1               5                   10

<210> SEQ ID NO 185
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:52

<400> SEQUENCE: 185

Phe Leu Leu Val Ala Ser Gln Arg Ser Val
1               5                   10

<210> SEQ ID NO 186
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:52

<400> SEQUENCE: 186

Leu Leu Val Ala Ser Gln Arg Ser Val
1               5

<210> SEQ ID NO 187
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:52

<400> SEQUENCE: 187

Arg Leu Tyr His Leu Leu Arg Gln Glu Leu
1               5                   10

<210> SEQ ID NO 188
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:52

<400> SEQUENCE: 188

Lys Leu Met Pro Asn Cys Lys Trp Val
1               5

<210> SEQ ID NO 189
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:52

```
<400> SEQUENCE: 189

Lys Leu Val Trp Phe Asp Leu Asp Leu
1               5

<210> SEQ ID NO 190
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:52

<400> SEQUENCE: 190

Arg Met Leu Arg His His Lys Lys Ala
1               5

<210> SEQ ID NO 191
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:52

<400> SEQUENCE: 191

Leu Gln Asn Pro Leu Leu Val Pro Val
1               5

<210> SEQ ID NO 192
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:52

<400> SEQUENCE: 192

Gly Val Leu Asp Val Ile Phe His Pro Thr
1               5                   10

<210> SEQ ID NO 193
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:53

<400> SEQUENCE: 193

Phe Ile Gln Gln Cys Thr Asp Asp Val
1               5

<210> SEQ ID NO 194
<211> LENGTH: 10
<212> TYPE: PRT
<213> ORGANISM: Artificial
<220> FEATURE:
<223> OTHER INFORMATION: Designed peptide based on the amino acid
      sequence of SEQ ID NO:53

<400> SEQUENCE: 194

Ala Met Ser Lys Arg Ser Lys Phe Ala Leu
1               5                   10

<210> SEQ ID NO 195
<211> LENGTH: 10
```

```
<212> TYPE: PRT
<213> ORGANISM: Artificial
<220> FEATURE:
<223> OTHER INFORMATION: Designed peptide based on the amino acid
      sequence of SEQ ID NO:53

<400> SEQUENCE: 195

Ala Leu Ile Thr Trp Ile Gly Glu Asn Val
1               5                   10

<210> SEQ ID NO 196
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:53

<400> SEQUENCE: 196

Trp Ile Gly Glu Asn Val Ser Gly Leu
1               5

<210> SEQ ID NO 197
<211> LENGTH: 9
<212> TYPE: PRT
<213> ORGANISM: Artificial
<220> FEATURE:
<223> OTHER INFORMATION: Designed peptide based on the amino acid
      sequence of SEQ ID NO:53

<400> SEQUENCE: 197

Val Gln Asn Phe Ala Lys Glu Phe Val
1               5
```